US012391755B2

(12) United States Patent
Mandel et al.

(10) Patent No.: US 12,391,755 B2
(45) **Date of Patent: *Aug. 19, 2025**

(54) METHODS OF USE FOR ANTI-ILT2 ANTIBODIES

(71) Applicant: Biond Biologics Ltd., Misgav (IL)

(72) Inventors: Ilana Mandel, Karmiel (IL); Tsuri Peretz, Kiryat Tivon (IL); Dana Haves Ziv, Karmiel (IL); Ilana Goldshtein, Misgav (IL); Dror Alishekevitz, Kiryat Tivon (IL); Anna Fridman-Dror, Kibbutz Dalia (IL); Motti Hakim, Kibbutz Gazit (IL); Avidor Shulman, Rakefet (IL); Yair Sapir, Manof (IL); Tehila Ben-Moshe, Tel Aviv (IL)

(73) Assignee: Biond Biologics Ltd., Misgav (IL)

( * ) Notice: Subject to any disclaimer, the term of this patent is extended or adjusted under 35 U.S.C. 154(b) by 678 days.

This patent is subject to a terminal disclaimer.

(21) Appl. No.: 17/533,945

(22) Filed: Nov. 23, 2021

(65) Prior Publication Data

US 2022/0153836 A1 May 19, 2022

Related U.S. Application Data

(60) Division of application No. 17/224,016, filed on Apr. 6, 2021, now Pat. No. 11,236,162, which is a continuation of application No. PCT/IL2020/050889, filed on Aug. 12, 2020.

(60) Provisional application No. 63/034,569, filed on Jun. 4, 2020, provisional application No. 62/885,374, filed on Aug. 12, 2019.

(51) Int. Cl.

| | |
|---|---|
| ***C07K 16/28*** | (2006.01) |
| ***A61K 39/00*** | (2006.01) |
| ***A61K 45/06*** | (2006.01) |
| ***A61P 35/00*** | (2006.01) |

(52) U.S. Cl.

CPC .......... *C07K 16/2803* (2013.01); *A61K 45/06* (2013.01); *A61P 35/00* (2018.01); *C07K 16/2863* (2013.01); *A61K 2039/505* (2013.01); *C07K 2317/565* (2013.01); *C07K 2317/76* (2013.01)

(58) Field of Classification Search

CPC ............ C07K 16/2863; C07K 16/2803; C07K 2317/565; C07K 2317/76; A61P 35/00

See application file for complete search history.

(56) References Cited

U.S. PATENT DOCUMENTS

| | | | |
|---|---|---|---|
| 10,316,094 | B2 | 6/2019 | Maute et al. |
| 11,236,162 | B2 | 2/2022 | Mandel et al. |
| 12,071,479 | B2 | 8/2024 | Mandel et al. |
| 2018/0298096 | A1 | 10/2018 | Joyce-Shaikh et al. |
| 2022/0153836 | A1 | 5/2022 | Mandel et al. |

FOREIGN PATENT DOCUMENTS

| | | | |
|---|---|---|---|
| CN | 101379089 | A | 4/2009 |
| RU | 2447449 | C2 | 4/2012 |
| WO | 2005/009465 | A1 | 2/2005 |
| WO | 2008/061019 | A2 | 5/2008 |
| WO | 2016/065329 | A1 | 4/2016 |
| WO | 2017/125532 | A1 | 7/2017 |
| WO | 2018/091580 | A1 | 5/2018 |
| WO | 2018/187518 | A1 | 10/2018 |
| WO | 2019/144052 | A1 | 7/2019 |
| WO | 2020/023268 | A1 | 1/2020 |
| WO | 2020006347 | A1 | 1/2020 |
| WO | 2020/136145 | A2 | 7/2020 |
| WO | 2020/136147 | A1 | 7/2020 |
| WO | 2021/074157 | A1 | 4/2021 |
| WO | 2021/133036 | A1 | 7/2021 |
| WO | 2021/222544 | A1 | 11/2021 |

OTHER PUBLICATIONS

Saverino et al., "The CD85/LIR-1/ILT2 Inhibitory Receptor Is Expressed by All Human T Lymphocytes and Down-Regulates Their Functions," J Immun. (2000) 165(7):3742-55.
Barkal et al., "Engagement of MHC class I by the inhibitory receptor LILRB1 suppresses macrophages and is a target of cancer immunotherapy," Nat Immunol. (2018) 19(1):76-84.
Chapman et al., "Crystal structure and ligand binding properties of the D1D2 region of the inhibitory receptor L1R-1 (ILT2)," Immunity (2000) 13(5):727-36.
Dumont et al., "CD8+PD-1-ILT2+ T cells are an intratumoral cytotoxic population selectively inhibited by the immune checkpoint HLA-G," Cancer Immunol Res. (2019) 1-33.
Favier et al., "ILT2/HLA-G interaction impairs NK-cell functions through the inhibition of the late but not the early events of the NK-cell activating synapse," The FASEB Journal, Federation of American Societies for Experimental Biology (2010) 24(3):689-99.
Kim et al., "LILRB1 blockade enhances bispecific T cell engager antibody-induced tumor cell killing by effector CD8+ T cells," J Immunol. (2019) 203(4):1076-87.
Kuroki et al., "Structural and functional basis for LILRB immune checkpoint receptor recognition of HLA-G isoforms," J Immunol. (2019) 203(12):3386-94.
Lesport et al., "Inhibition of human Vγ9Vδ2 T-cell antitumoral activity through HLA-G: implications for immunotherapy of cancer," Cellular and Molecular Life Sciences (2011) 68(3):3385-399.
Lin et al., "Human Leukocyte Antigen-G (HLA-G) expression in cancers: roles in immune evasion, metastasis and target for therapy," Molecular Medicine (2015) 21(1):782-91.

(Continued)

*Primary Examiner* — Elly-Gerald Stoica
(74) *Attorney, Agent, or Firm* — The Roy Gross Law Firm, LLC; Roy D. Gross

(57) ABSTRACT

The present invention provides monoclonal antibodies, or antigen-binding portions thereof, against ILT2, as well as pharmaceutical compositions comprising same and methods of producing same. Also provided are methods of treating cancer comprising administering the antibodies or compositions of the invention. Methods of treating cancer, combination treatments, and patient selection are also provided.

20 Claims, 50 Drawing Sheets

Specification includes a Sequence Listing.

(56) References Cited

OTHER PUBLICATIONS

Mandel et al., "BND-22, a first-in-class, anti-ILT2 monoclonal antibody inhibits the immunosuppressive effects of HLA-G and enhances anti-tumor activity of immune cells in preclinical in vitro, ex vivo, and in vivo models," Proceedings of the Annual Meeting of the American Association for Cancer Research 2020; Apr. 27-28, 2020 and Jun. 22-24. Philadelphia (PA): AACR; Cancer Res (2020) 80(16 Suppl): Poster for Abstract 3266 (first made public Jun. 22, 2020).
Mandel et al., "BND-22, a first-in-class, anti-ILT2 monoclonal antibody inhibits the immunosuppressive effects of HLA-G and enhances anti-tumor activity of immune cells in preclinical in vitro, ex vivo, and in vivo models," Proceedings of the Annual Meeting of the American Association for Cancer Research 2020; Apr. 27-28, 2020 and Jun. 22-24. Philadelphia (PA): AACR; Cancer Res (2020) 80(16 Suppl): Abstract 3266 (first made public May 15, 2020).
Steevels et al., "Immune inhibitory receptors: essential regulators of phagocyte function," Eur J Immunol. (2011). 41:575-87.
Wang et al., "Structures of the four Ig-like domain LILRB2 and the four-domain LILRB1 and HLA-G1 complex," Cell Mol Immunol. (2020) 17(9):966-75 (e-published Jul. 4, 2019).
Jul. 22, 2021 Search Report for Korean Patent Application No. 10-2021-7012249.
Godal et al., "Natural Killer Cell Killing of Acute Myelogenous Leukemia and Acute Lymphoblastic Leukemia Blasts by Killer Cell Immunoglobulin-Like Receptor-Negative Natural Killer Cells after NKG2A and LIR-1 Blockade," Biology of Blood and Marrow Transplantation (2010) 16(5): 612-21.
Naji et al., "Soluble HLA-G and HLA-G1 Expressing Antigen-Presenting Cells Inhibit T-Cell Alloproliferation through ILT-2/ILT-4/FasL-Mediated Pathways," Hum Immunol. (2007) 68(4):233-9.
Yan, "HLA-G Expression in Cancers: Potential Role in Diagnosis, Prognosis and Therapy," Endocr Metab Immune Disord.—Drug Targets (2011) 11:76-89.
Schlothauer et al., "Novel Human IgG1 and IgG4 Fc-engineered antibodies with completely abolished immune effector functions," Protein Engineering, Design and Selection (2016) 29(10):457-66.
Janeway et al., "The interaction of the antibody molecule with specific antigen." Immunobiology: The Immune System in Health and Disease, 5th Ed. (2001): 5 pages. https://www.ncbi.nlm.nih.gov/books/NBK27160.
Anonymous, "The central role of excipients in drug formulation." (2013): 13 pages. https://www.europeanpharmaceuticalreview.com/article/18434/the-central-role-of-excipients-in-drug-formulation-2/.
McCarthy et al., "Altering the fine specificity of an anti-Legionella single chain antibody by a single amino acid insertion," J Immunol. Methods (2001) 251(1-2):137-49.
Lin et al., "Improved affinity of a chicken single-chain antibody to avian infectious bronchitis virus by site-directed mutagenesis of complementarity-determining region H3," African Journal of Biotechnology (2011) 10(79):18294-302.
Dumet et al., "Insights into the IgG heavy chain engineering patent landscape as applied to IgG4 antibody development," Mabs (2019) 11(8):1341-50.
U.S. Appl. No. 17/224,016, filed Apr. 6, 2021 / U.S. Pat. No. 11,236,262, Feb. 1, 2022, Ilana Mandel.
U.S. Appl. No. 17/399,971, filed Aug. 11, 2021/ U.S. Pat. No. 12,071,479, Aug. 27, 2024, Ilana Mandel.
U.S. Appl. No. 18/770,474, filed Jul. 11, 2024, Dana Haves Ziv.

Figure 1
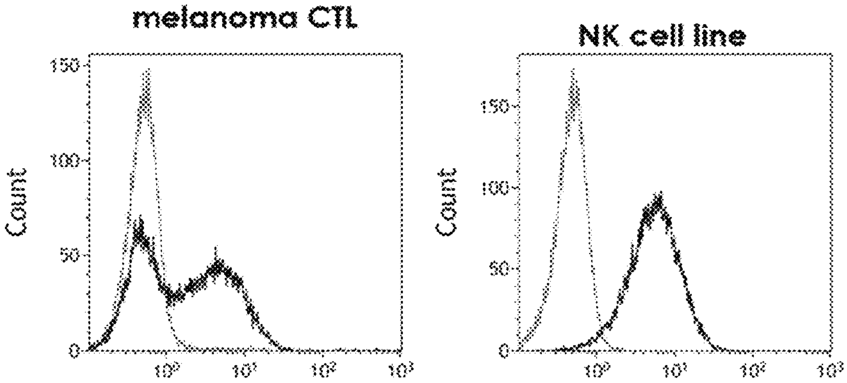
Figure 2
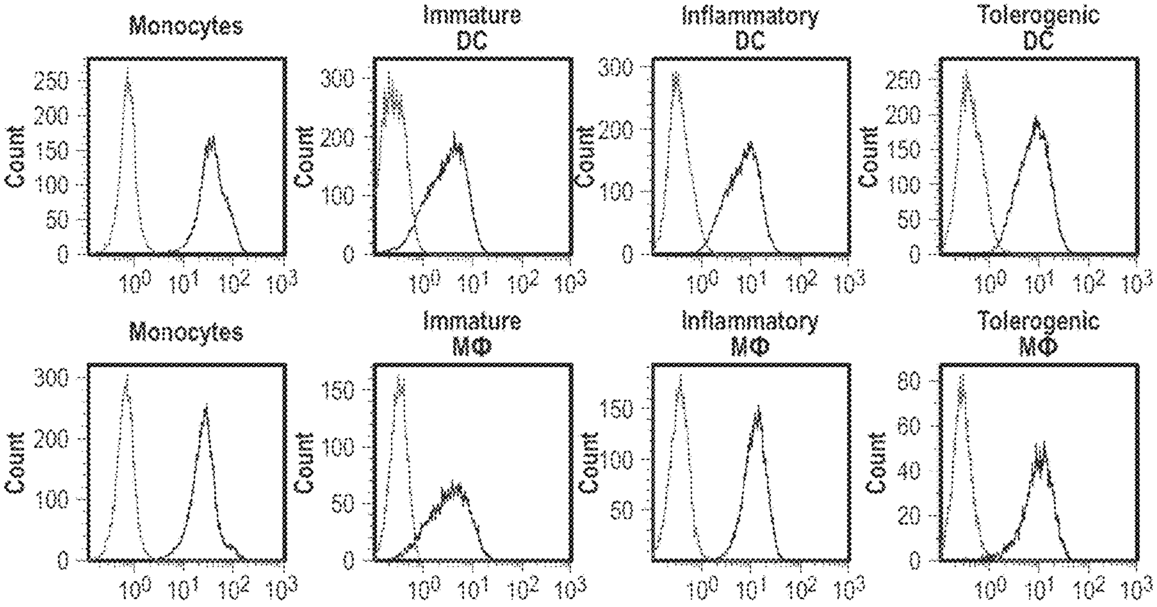
Figure 3A
| TCGA Cancer Type | Cancer name | Fold Over Expression (vs Normal) | N samples |
|---|---|---|---|
| KIRC | Kidney renal clear cell carcinoma | 10.4 | 534 |
| KIPAN | Pan kidney cohort (KIRC, KIRP, KICH) | 7.74 | 891 |
| SARC | Sarcoma | 3.03 | 263 |
| GBM | Glioblastoma multiform | 2.67 | 166 |
| UCEC | Uterine Corpus Endometrial Carcinoma | 2.33 | 546 |
| HNSC | Head and Neck squamous cell carcinoma | 2.2 | 522 |

Figure 3B
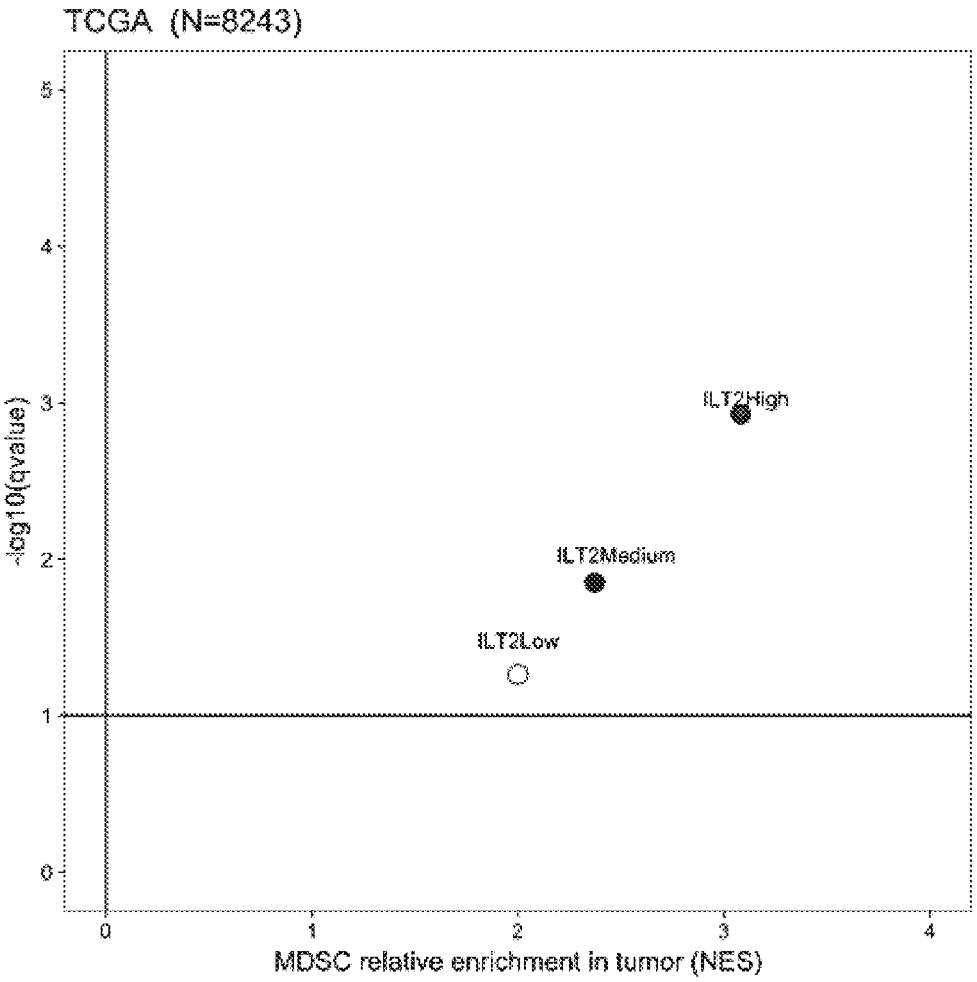
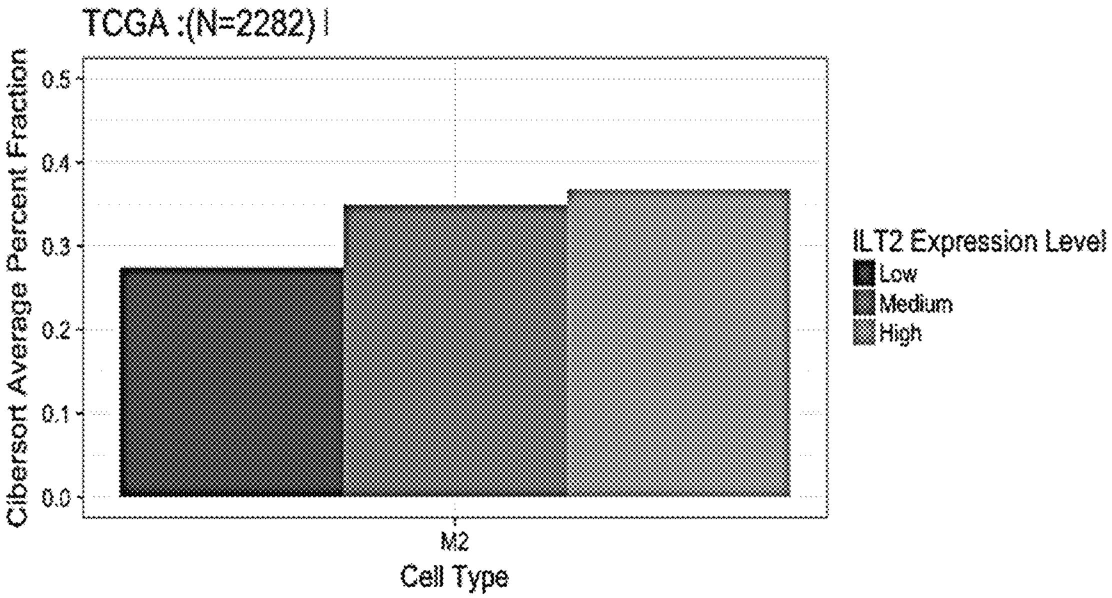

19E3 heavy chain variable region (Murine)

```
          10        20        30        40        50        60        70        80        90
CAGGTTCAGCTGCAGCAGTCTGGAGCTGAGCTGGCGAGGCCTGGGGCTTCAGTGAAGCTGTCCTGCAAGGCTTCTGGCTACACCTTCACAAGCTATGGTA  100
Q  V  Q  L  Q  Q  S  G  A  E  L  A  R  P  G  A  S  V  K  L  S  C  K  A  S  G  Y  T  F  T  S  Y  G  I   33

TAAGCTGGGTGAAGCAGAGAACTGGACAGGGCCTTGAGTGGGTTGGAGAGATTTATCCTGGAAGTGGTAATTCTTACTACAATGAGAAGTTCAAGGGCAA  200
 S  W  V  K  Q  R  T  G  Q  G  L  E  W  V  G  E  I  Y  P  G  S  G  N  S  Y  Y  N  E  K  F  K  G  K   66

GGCCACACTGACTGCAGACAAATCCTCCAGCACAGCGTACATGGAGCTCCGCAGCCTGACATCTGAGGACTCTGCGGTCTATTTCTGTGCAAGATCGAAT  300
 A  T  L  T  A  D  K  S  S  S  T  A  Y  M  E  L  R  S  L  T  S  E  D  S  A  V  Y  F  C  A  R  S  N   99

GATGGTTACCCTGACTACTGGGGCCAAGGCACCACTCTCACAGTCTCCTCA  351  SEQ ID NO: 32
D  G  Y  P  D  Y  W  G  Q  G  T  T  L  T  V  S  S    117  SEQ ID NO: 21
```

19E3 light chain variable region (Murine)

```
          10        20        30        40        50        60        70        80        90
GACATCCAGATGACACAATCTTCATCCTACTTGTCTGTATCTCTAGGAGGCAGAGTCACCATTACTTGCAAGGCAAGTGACCACATTAATAATTGGTTAG  100
D  I  Q  M  T  Q  S  S  S  Y  L  S  V  S  L  G  G  R  V  T  I  T  C  K  A  S  D  H  I  N  N  W  L  A   33

CCTGGTATCAGCAGAAACCAGGAAATGCTCCTAGGCTCTTAATATCTGGTGCAACCAGTTTGGAAACTGGGGTTCCTTCAAGATTCAGTGGCAGTGGATC  200
 W  Y  Q  Q  K  P  G  N  A  P  R  L  L  I  S  G  A  T  S  L  E  T  G  V  P  S  R  F  S  G  S  G  S   66

TGGAAAGGATTACACTCTCAGCATTACCAGTCTTCAGACTGAAGATGTTGCTACTTATTACTGTCAACAGTATTGGAGTACTCCGTGGACGTTCGGTGGA  300
 G  K  D  Y  T  L  S  I  T  S  L  Q  T  E  D  V  A  T  Y  Y  C  Q  Q  Y  W  S  T  P  W  T  F  G  G   99

GGCACCAAGCTGGAAATCAAA  321  SEQ ID NO: 39
G  T  K  L  E  I  K    107  SEQ ID NO: 22
```

Figure 6

15G8 heavy chain variable region (Murine)

10 20 30 40 50 60 70 80 90

GATGTACAGCTTCAGGGGTCAGGACCTGGCCTCGTGAAACCTTCTCAGTCTCTGTCTCTCACCTGCTCTGTCACTGGCTACTCCATCACCAGTGGTTATT 100
D V Q L Q G S G P G L V K P S Q S L S L T C S V T G Y S I T S G Y Y 33

ACTGGAACTGGATCCGGCAGTTTCCAGGAAACAAACTGGAATGGATGGGCTACATAAGCTACGATGGTAGCAATAACTACAACCCATCTCTCAAAAATCG 200
W N W I R Q F P G N K L E W M G Y I S Y D G S N N Y N P S L K N R 66

AATCTCCATCACTCGTGACACATCTAAGAACCAGTTTTTCCTGAAGTTGAATTCTGTGACTTCTGAGGACACAGCCACATATTACTGTGCCCATGGTTAC 300
I S I T R D T S K N Q F F L K L N S V T S E D T A T Y Y C A H G Y 99

TCATATTACTATGCTATGGACTGCTGGGGTCAAGGAACCTCAGTCACCGTCTCCTCA 357 SEQ ID NO: 33
S Y Y Y A M D C W G Q G T S V T V S S 119 SEQ ID NO: 30

15G8 light chain variable region (Murine)

10 20 30 40 50 60 70 80 90

GATATCCAGATGACACAGACTACATCCTCCCTGTCTGCCTCTCTGGGAGACAGAGTCACCATCAGTTGCAGGACAAGTCAGGACATTAGCAATTATTTAA 100
D I Q M T Q T T S S L S A S L G D R V T I S C R T S Q D I S N Y L N 33

ACTGGTATCAGCAGAAACCAGATGGAACTGTTAAACTCCTGATCTCCTACACATCAAGATTGCACTCAGGAGTCCCATCAAGGTTCAGTGGCAGTGGGTC 200
W Y Q Q K P D G T V K L L I S Y T S R L H S G V P S R F S G S G S 66

TGGAACAGATTATTCTCTCACCATTAGCAACCTGGAGCAAGAAGATATTGCCACTTACTTTTGCCAACAGGGTAATACGCTTCCCACGTTCGGCTCGGGG 300
G T D Y S L T I S N L E Q E D I A T Y F C Q Q G N T L P T F G S G 99

ACAAAGTTGGAAATAAAA 318 SEQ ID NO: 37
T K L E I K 106 SEQ ID NO: 45

Figure 6 continued

15G8 heavy chain variable region (Human)

```
         10        20        30        40        50        60        70        80        90
GATGTCCAGCTGCAAGGCTCTGGCCCTGGACTGGTTAAGCCTTCCGAGACACTGTCCCTGACCTGCTCTGTGACCGGCTACTCTATCACCTCCGGCTACT 100
 D  V  Q  L  Q  G  S  G  P  G  L  V  K  P  S  E  T  L  S  L  T  C  S  V  T  G  Y  S  I  T  S  G  Y  Y 33

ACTGGAACTGGATCAGACAGTTCCCCGGCAAGAAACTGGAATGGATGGGCTACATCTCCTACGACGGCTCCAACAACTACAACCCCAGCCTGAAGAACCG 200
  W  N  W  I  R  Q  F  P  G  K  K  L  E  W  M  G  Y  I  S  Y  D  G  S  N  N  Y  N  P  S  L  K  N  R 66

GATCACCATCTCTCGGGACACCTCCAAGAACCAGTTCTCCCTGAAGCTGAACTCCGTGACCGCTGCCGATACCGCTACCTACTACTGTGCTCACGGCTAC 300
  I  T  I  S  R  D  T  S  K  N  Q  F  S  L  K  L  N  S  V  T  A  A  D  T  A  T  Y  Y  C  A  H  G  Y 99

TCCTACTACTACGCCATGGATGCTTGGGGCCAGGGCACATCTGTGACAGTGTCCTCT 357   SEQ ID NO: 34
 S  Y  Y  Y  A  M  D  A  W  G  Q  G  T  S  V  T  V  S  S  119   SEQ ID NO: 28
```

15G8 light chain variable region (Human)

```
         10        20        30        40        50        60        70        80        90
GACATCCAGATGACCCAGTCTCCATCCTCTCTGTCTGCCTCTGTGGGCGACAGAGTGACCATCACCTGTCGGACCTCTCAGGACATCTCCAACTACCTGA 100
 D  I  Q  M  T  Q  S  P  S  S  L  S  A  S  V  G  D  R  V  T  I  T  C  R  T  S  Q  D  I  S  N  Y  L  N 33

ACTGGTATCAGCAGAAACCCGGCAAGGCCGTGAAGCTGCTGATCTCCTACACCTCCAGACTGCACTCTGGCGTGCCCTCCAGATTTTCTGGCTCTGGATC 200
  W  Y  Q  Q  K  P  G  K  A  V  K  L  L  I  S  Y  T  S  R  L  H  S  G  V  P  S  R  F  S  G  S  G  S 66

TGGCACCGACTACACCCTGACCATCAGTTCTCTGCAGCCTGAGGACTTCGCCACCTACTACTGTCAGCAGGGCAACACCCTGCCTACCTTTGGCCAGGGC 300
  G  T  D  Y  T  L  T  I  S  S  L  Q  P  E  D  F  A  T  Y  Y  C  Q  Q  G  N  T  L  P  T  F  G  Q  G 99

ACCAAGCTGGAAATCAAG 318   SEQ ID NO: 38
 T  K  L  E  I  K  106   SEQ ID NO: 24
```

Figure 6 continued_1

17F2 heavy chain variable region (Murine)

```
         10        20        30        40        50        60        70        80        90       100
CAGGTTCAGCTGCAACAGTCTGACGCTGAGTTGGTGAAACCTGGAGCTTCAGTGAAGATATCCTGCAAGGTTTCTGGCTACACCTTCACTGACCATACTA
 Q  V  Q  L  Q  Q  S  D  A  E  L  V  K  P  G  A  S  V  K  I  S  C  K  V  S  G  Y  T  F  T  D  H  T
                            10                            20                            30

        110       120       130       140       150       160       170       180       190       200
TTCACTGGATGAAGCAGAGGCCTGAACAGGGCCTGGAATGGATTGGATATATTTATCCTAGAGATGGTAGTACTAAGTACAATGAGAAGTTCAAGGGCAA
I  H  W  M  K  Q  R  P  E  Q  G  L  E  W  I  G  Y  I  Y  P  R  D  G  S  T  K  Y  N  E  K  F  K  G  K
                  40                            50    52 A                          60

        210       220       230       240       250       260       270       280       290       300
GGCCACATTGACTGCAGACAAATCCTCCAGCACAGCCTACATGCAGCTCAACAGCCTGACATCTGAGGACTCTGCAGTCTATTTCTGTGCAAGAACCTGG
  A  T  L  T  A  D  K  S  S  S  T  A  Y  M  Q  L  N  S  L  T  S  E  D  S  A  V  Y  F  C  A  R  T  W
        70                            80    82 A  B  C                       90

        310       320       330       340
GACTACTTTGACTACTGGGGCCAAGGCACCACTCTCACAGTCTCCTCA   SEQ ID NO: 35
 D  Y  F  D  Y  W  G  Q  G  T  T  L  T  V  S  S    SEQ ID NO: 19
    99101                     110
```

17F2 light chain variable region (Murine)

```
         10        20        30        40        50        60        70        80        90       100
GACATTGTGCTGACCCAATCTCCAGCTTCTTTGGCTGTGTCTCTAGGGCAGAGGGCCACCATATCCTGCAGAGCCAGTGAAAGTGTTGATAGTTATGGCA
 D  I  V  L  T  Q  S  P  A  S  L  A  V  S  L  G  Q  R  A  T  I  S  C  R  A  S  E  S  V  D  S  Y  G
                            10                            20                   27  A  B  C  D 28

        110       120       130       140       150       160       170       180       190       200
ATAGTTTTATGCACTGGTACCAGCAGAAACCAGGACAGCCACCCAAACTCCTCATCTATCGTGCATCCAACCTAGAATCTGGGATCCCTGCCAGGTTCAG
N  S  F  M  H  W  Y  Q  Q  K  P  G  Q  P  P  K  L  L  I  Y  R  A  S  N  L  E  S  G  I  P  A  R  F  S
30                            40                            50                            60

        210       220       230       240       250       260       270       280       290       300
TGGCAGTGGGTCTAGGACAGACTTCACCCTCACCATTAATCCTGTGGAGGCTGATGATGTTGCAACCTATTACTGTCAGCAAAGTAATGAGGATCCGTAC
  G  S  G  S  R  T  D  F  T  L  T  I  N  P  V  E  A  D  D  V  A  T  Y  Y  C  Q  Q  S  N  E  D  P  Y
                    70                            80                            90

        310       320       330
ACGTTCGGAGGGGGGACCAAGCTGGAAATAAAA   SEQ ID NO: 36
 T  F  G  G  G  T  K  L  E  I  K    SEQ ID NO: 20
       100                  108  A
```

Figure 6 continued_2

Figure 7A

| Clone# | ELISA (OD) | | | |
|---|---|---|---|---|
| | | | | |
| | hILT2-Fc | PIRB | hILT6-His | hLILRA1-His |
| 17F2 | 1.89 | 0.06 | 0.06 | 0.08 |
| 19E3 | 2.61 | 0.14 | 0.13 | 0.11 |
| 15G8 | 1.11 | 0.08 | 0.07 | 0.14 |
| Positive | 2.45 | 4.73 | 4.86 | 4.39 |
| Negative | 0.05 | 0.0575 | 0.071 | 0.13 |

Figure 11A
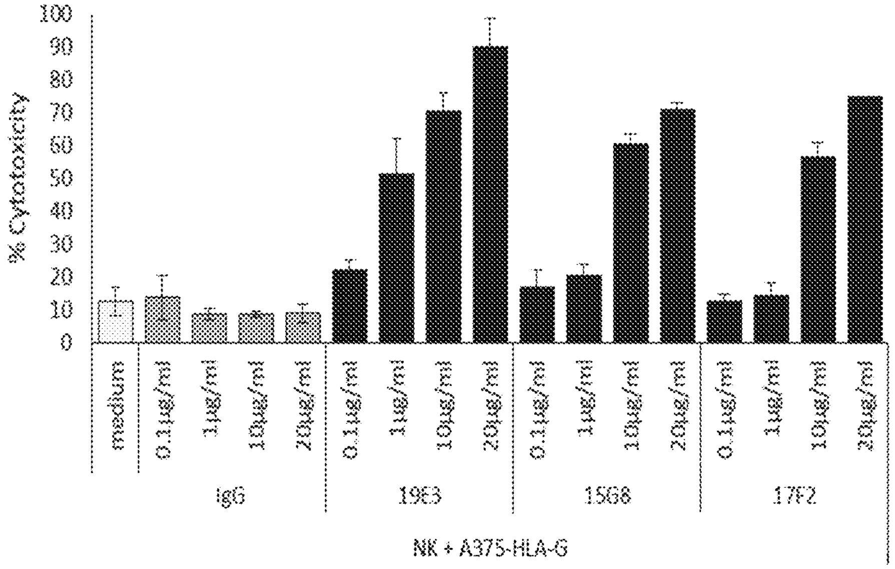
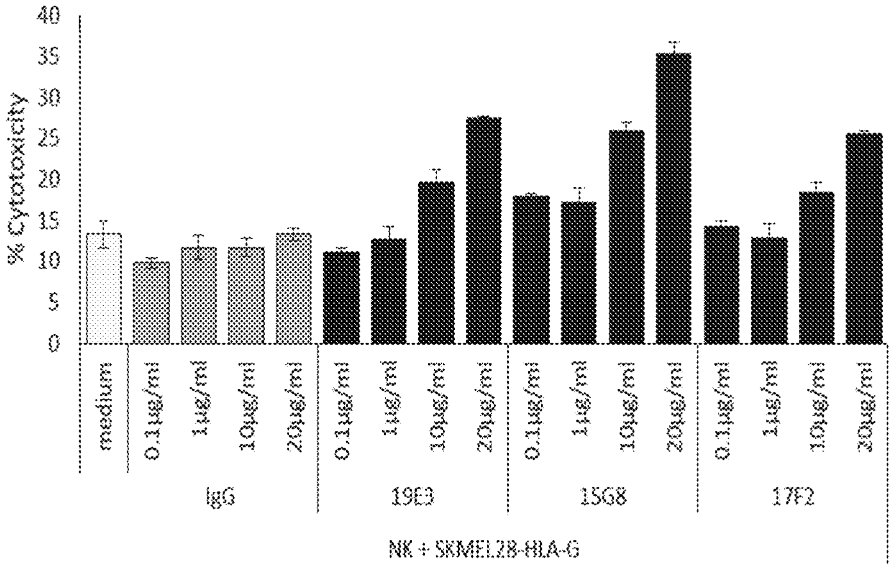

```
1-   HLPKPTLWAE PGSVITQGSP VTLRCQGGQE TQEYRLYREK KTALWITRIP QELVKKGQFP
61-  IPSITWEHAG RYRCYYGSDT AGRSESSDPL ELVVTGAYIK PTLSAQPSPV VNSGGNVILQ
121- CDSQVAFDGF SLCKEGEDEH PQCLNSQPHA RGSSRAIFSV GPVSPSRRWW YRCYAYDSNS
181- PYEWSLPSDL LELLVLGVSK KPSLSVQPGP IVAPEETLTL QCGSDAGYNR FVLYKDGERD
241- FLQLAGAQPQ AGLSQANFTL GPVSRSYGGQ YRCYGAHNLS SEWSAPSDPL DILIAGQFYD
301- RVSLSVQPGP TVASGENVTL LCQSQGWMQT FLLTKEGAAD DPWRLRSTYQ SQKYQAEFPM
361- GPVTSAHAGT YRCYGSQSSK PYLLTHPSDP LEL
```

SEQ ID NO: 40

Interaction regions
- Region 1
- Region 2
- Region 3
- Region 4

Epitope residues
- Very highly probable
- Highly probable
- Probable
- Possible

Figure 18A

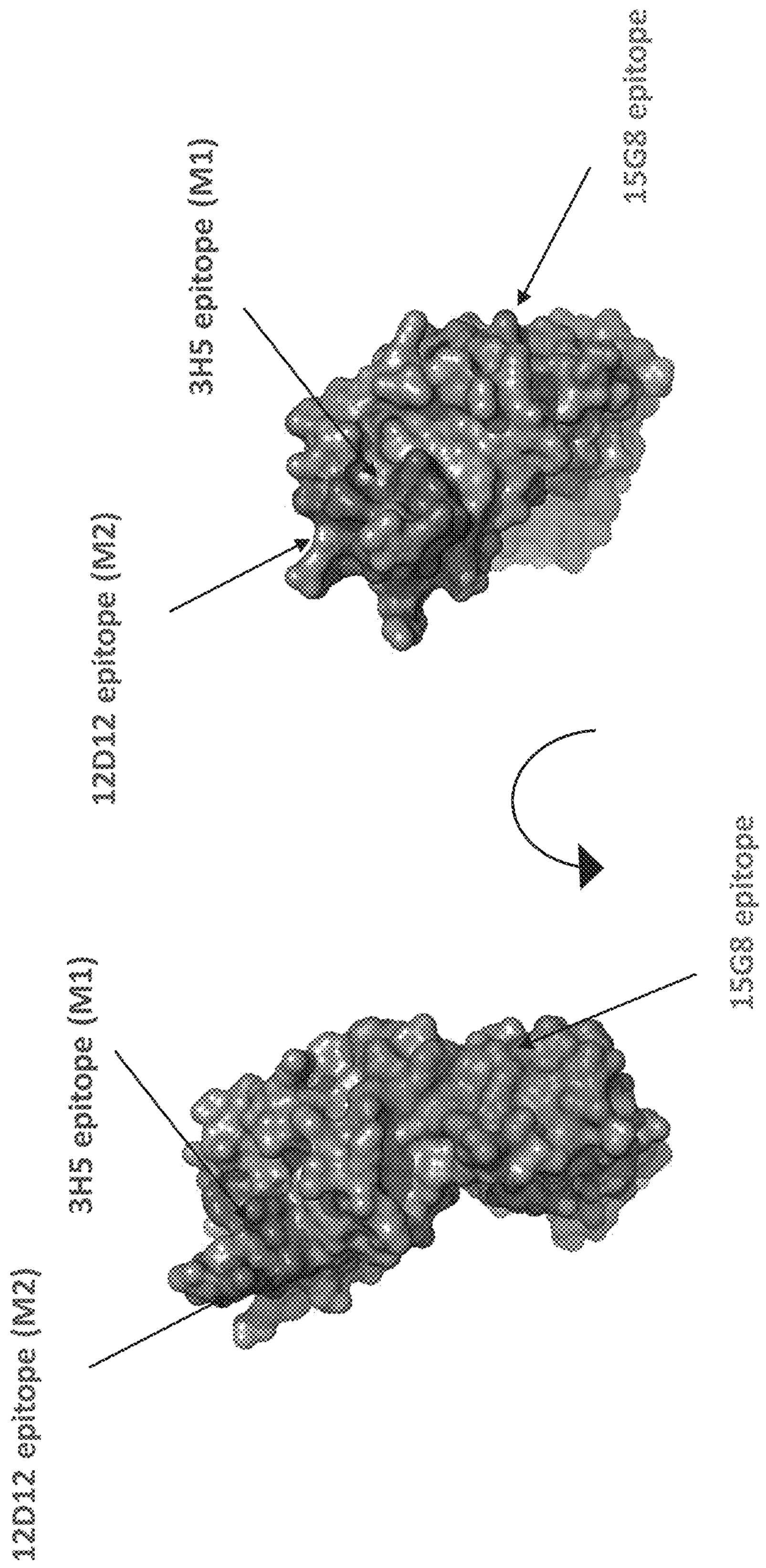
Figure 18D_continued

METHODS OF USE FOR ANTI-ILT2 ANTIBODIES

CROSS REFERENCE TO RELATED APPLICATIONS

This application is a division of U.S. application Ser. No. 17/224,016, filed Apr. 6, 2021, which is a continuation of International Application No. PCT/IL2020/050889, filed Aug. 12, 2020, which claims the benefit of priority of U.S. Provisional Patent Application No. 63/034,569, filed Jun. 4, 2020, and U.S. Provisional Patent Application No. 62/885,374, filed Aug. 12, 2019. The disclosures of the aforementioned priority applications are all incorporated herein by reference in their entirety.

SEQUENCE LISTING

The instant application contains a Sequence Listing which has been submitted electronically in ASCII format and is hereby incorporated by reference in its entirety. The electronic copy of the Sequence Listing, created on Apr. 6, 2021, is named 022548_C1090_SL.txt and is 31,158 bytes in size.

FIELD OF INVENTION

The present invention is in the field of monoclonal antibodies and modulating the immune response to cancer.

BACKGROUND OF THE INVENTION

ILT2, also known as LILRB1, LIR1 and CD85j is a cell surface protein expressed on immune cells that has a known function in inhibiting the immune response. The protein contains 4 IgC domains in the extracellular region and 4 intracellular ITIM domains. It is a member of the ILT family, which is made up of ILT1, ILT2, ILT3 and ILT4. ILT2 is most similar to ILT4, having ~80% homology. Known ligands of ILT2 include MHC-1 as well as non-classical MHC molecules such as HLA-F, HLA-G, HLA-B27 and UL18 (human CMV). The strongest known interactor of ILT2 in the human genome is HLA-G1.

HLA-G1 is widely expressed on the surface of various malignancies including breast, cervical, CRC, lung, gastric, pancreatic, thyroid and ovarian cancer cells as well as glioblastoma multiform, melanoma cells. Its expression is associated with poor clinical outcomes. Further, ILT2 expression in the tumor microenvironment has been associated with poor clinical response to oncolytic immune therapy, even when HLA-G1 is not present. Harnessing the immune response as a weapon against cancer and for cancer surveillance is a promising avenue for cancer prevention and treatment. However, ILT2 presents a roadblock to effective immune therapy. Treatment modalities that can circumvent the ILT2-HLA-G1 axis, as well as HLA-G1-independent functions of ILT2, are greatly needed.

SUMMARY OF THE INVENTION

The present invention provides monoclonal antibodies that bind to ILT2 and inhibit ILT2-mediated immune cell suppression; as well as pharmaceutical compositions comprising same. There is also provided methods of treating cancer comprising administering the compositions of the invention, methods of producing the antibodies, binding fragments and compositions of the invention, as well as methods of increasing the efficacy of PD-1/PD-L1 based therapy.

According to a first aspect, there is provided a monoclonal antibody or antigen-binding fragment comprising three heavy chain CDRs (CDR-H) and three light chain CDRs (CDR-L), wherein:

a. CDR-H1 comprises the amino acid sequence set forth in SEQ ID NO: 13 (SGYYWN), CDR-H2 comprises the amino acid sequence as set forth in SEQ ID NO: 14 (YISYDGSNNYNPSLKN), CDR-H3 comprises the amino acid sequence as set forth in SEQ ID NO: 15 (GYSYYYAMDX), CDR-L1 comprises the amino acid sequence as set forth in SEQ ID NO: 16 (RTSQDISNYLN), CDR-L2 comprises the amino acid sequence as set forth in SEQ ID NO: 17 (YTSRLHS), and CDR-L3 comprises the amino acid sequence as set forth in SEQ ID NO: 18 (QQGNTLPT), wherein the X is selected from A, C and S;
b. CDR-H1 comprises the amino acid sequence set forth in SEQ ID NO: 1 (DHTIH), CDR-H2 comprises the amino acid sequence as set forth in SEQ ID NO: 2 (YIYPRDGSTKYNEKFKG), CDR-H3 comprises the amino acid sequence as set forth in SEQ ID NO: 3 (TWDYFDY), CDR-L1 comprises the amino acid sequence as set forth in SEQ ID NO: 4 (RASESVDSYGNSFMH), CDR-L2 comprises the amino acid sequence as set forth in SEQ ID NO: 5 (RASNLES), and CDR-L3 comprises the amino acid sequence as set forth in SEQ ID NO: 6 (QQSNEDPYT); or
c. CDR-H1 comprises the amino acid sequence set forth in SEQ ID NO: 7 (GYTFTSYGIS), CDR-H2 comprises the amino acid sequence as set forth in SEQ ID NO: 8 (EIYPGSGNSYYNEKFKG), CDR-H3 comprises the amino acid sequence as set forth in SEQ ID NO: 9 (SNDGYPDY), CDR-L1 comprises the amino acid sequence as set forth in SEQ ID NO: 10 (KASDHINNWLA), CDR-L2 comprises the amino acid sequence as set forth in SEQ ID NO: 11 (GATSLET), and CDR-L3 comprises the amino acid sequence as set forth in SEQ ID NO: 12 (QQYWSTPWT).

According to some embodiments, the antibody or antigen-binding fragment of the invention comprises a heavy chain comprising an amino acid sequence selected from:

```
                                           SEQ ID NO: 19
(QVQLQQSDAELVKPGASVKISCKVSGYTFTDHTIHWMKQRPEQGLEWI
GYIYPRDGSTKYNEKFKGKATLTADKSSSTAYMQLNSLTSEDSAVYFCA
RTWDYFDYWGQGTTLTVSS),

                                           SEQ ID NO: 21
(QVQLQQSGAELARPGASVKLSCKASGYTFTSYGISWVKQRTGGLEWVG
EIYPGSGNSYYNEKFKGKATLTADKSSSTAYMELRSLTSEDSAVYCARS
NDGYPDYWGQGTTLTVSS)
and

                                           SEQ ID NO: 23
(DVQLQGSGPGLVKPSETLSLTCSVTGYSITSGYYWNWIRQFPGKKLEW

MGYISYDGSNNYNPSLKNRITISRDTSKNQFSLKLNSVTAADTATYYCA

HGYSYYYAMDXWGQGTSVTVSS), wherein the X is selected

from A, C and S.
```

According to some embodiments, the antibody or antigen-binding fragment of the invention comprises a light chain comprising an amino acid sequence selected from:

```
                                        SEQ ID NO: 20
(DIVLTQSPASLAVSLGQRATISCRASESVDSYGNSFMHWYQQKPGQPP
KLLIYRASNLESGIPARFSGSGSRTDFTLTINPVEADDVATYYCQQSNE
DPYTFGGGTKLEIK),

                                        SEQ ID NO: 22
(DIQMTQSSSYLSVSLGGRVTITCKASDHINNWLAWYQQKPGNAPRLIL
ISGATSLETGVPSRFSGSGSGKDYTLSITSLQTEDVATYYCQQYWSTPW
TFGGGTKLEIK),

                                        SEQ ID NO: 24
(DIQMTQSPSSLSASVGDRVTITCRTSQDISNYLNWYQQKPGKAVKLLI
SYTSRLHSGVPSRFSGSGSGTDYTLTISSLQPEDFATYYCQQGNTLPTF
GQGTKLEIK)
and

                                        SEQ ID NO: 45
(DIQMTQTTSSLSASLGDRVTISCRTSQDISNYLNWYQQKPDGFVKLLI
SYTSRLHSGVPSRFSGSGSGTDYSLTISNLEQEDIATYFCQQGNTLPTF
GSGTKLEIK).
```

According to some embodiments, the antibody or antigen-binding fragment is humanized, and the X is selected from A and S.

According to some embodiments, the X is A, SEQ ID NO: 15 is GYSYYYAMDA (SEQ ID NO: 25) and SEQ ID NO: 23 is DVQLQGSGPGLVKPSETLSLTCSVTGYSITS-GYYWNWIRQFPGKKLEWMGYISYDG SNNYNPSLK-NRITISRDTSKNQFSLKLNSVTAADTATYYCAHGYS-YYYAMDAWGQ GTSVTVSS (SEQ ID NO: 28).

According to another aspect, there is provided a monoclonal antibody or antigen-binding fragment that binds a human leukocyte immunoglobulin-like receptor subfamily B member 1 (ILT2) epitope within a sequence of human ILT2 selected from

```
                    (SEQ ID NO: 41)
VKKGQFPIPSITWEH,

                    (SEQ ID NO: 42)
LELVVTGAYIKPTLS,

                    (SEQ ID NO: 43)
VILQCDSQVAPDGFS
and

                    (SEQ ID NO: 44)
WYRCYAYDSNSPYEW.
```

According to some embodiments, the epitope is a 3-dimensional epitope comprising SEQ ID NO: 41, 42, 43 and 44.

According to another aspect, there is provided a monoclonal antibody or antigen-binding fragment that binds ILT2 and inhibits direct interaction between the ILT2 and beta-2-microglobulin (B2M).

According to some embodiments, the antibody or antigen-binding fragment inhibits interaction of the ILT2 and an HLA protein or MHC-I protein via the inhibition of ILT2 direct interaction with B2M.

According to some embodiments, the HLA is HLA-G.

According to another aspect, there is provided a monoclonal antibody or antigen-binding fragment that binds ILT2 and induces in a subject suffering from cancer at least three of:

a. increased natural killer (NK) cell cytotoxicity;
b. increased T cell cytotoxicity, proliferation, or both;
c. increased macrophage phagocytosis, increased generation of M1 inflammatory macrophages, decreased generation of M2 suppressor macrophages or a combination thereof; and
d. increased dendritic cell homing to a tumor of the cancer, increased dendritic cell activation or a combination thereof.

According to some embodiments, the cancer is a HLA-G or MHC-1 expressing cancer.

According to some embodiments, the antibody or antigen-binding fragment of the invention is for use in at least one of binding ILT2, inducing/enhancing an anti-tumor T-cell response, increasing T-cell proliferation, reducing cancer-induced suppressor myeloid activity, increasing natural killer cell cytotoxicity, increasing macrophage phagocytosis, increasing generation of M1 inflammatory macrophages, decreasing generation of M2 suppressor macrophages, increasing dendritic cell number in a tumor microenvironment, increasing dendritic cell activation, treating an HLA-G expressing cancer, and treating a MHC-I expressing cancer.

According to some embodiments, the antibody or antigen-binding fragment of the invention is for use in combination with an opsonizing agent for treating an HLA-G or MHC-I expressing cancer.

According to some embodiments, the antibody or antigen-binding fragment of the invention is for use in combination with an anti-PD-L1/PD-1 based therapy for treating an HLA-G or MHC-I expressing cancer.

According to another aspect, there is provided a method of treating an HLA-G or MHC-I expressing cancer in a subject in need thereof, the method comprising administering to the subject a pharmaceutical composition comprising an antibody or antigen-binding fragment of the invention.

According to some embodiments, the method of the invention further comprises administering to the subject an opsonizing agent.

According to some embodiments, the opsonizing agent is an EGFR inhibitor, optionally wherein the EGFR inhibitor is cetuximab.

According to some embodiments, the method of the invention further comprises administering to the subject an anti-PD-L1/PD-1 based immunotherapy.

According to another aspect, there is provided a method of treating an HLA-G or MHC-I expressing cancer in a subject in need thereof, the method comprising:

a. confirming expression of ILT2 or soluble HLA-G in the subject is above a predetermined threshold; and
b. administering to the subject an agent that inhibits ILT2 based immune suppression; thereby treating a cancer in a subject.

According to some embodiments, the confirming comprises measuring expression of the ILT2 or soluble HLA-G in the subject before the administering.

According to some embodiments, the method of the invention comprises confirming expression of ILT2 and wherein the expression of ILT2 is in an immune cell of the subject.

According to some embodiments, the immune cell is selected from a peripheral blood immune cell and an intra-tumor immune cell.

According to some embodiments, the immune cell is selected from a CD8 positive T cell, a macrophage, an NK cell and a TEMRA cell.

According to some embodiments, the immune cell is a peripheral blood CD8 positive T cell.

According to some embodiments, the method of the invention comprises confirming expression of soluble HLA-G.

According to some embodiments, the method of the invention further comprises administering to the subject an anti-PD-L1/PD-1 based therapy.

According to another aspect, there is provided a method of treating an HLA-G or MHC-I expressing cancer in a subject in need thereof, the method comprising:

a. administering to the subject an agent that inhibits ILT2 based immune suppression; and
b. administering to the subject an anti-PD-L1/PD-1 based therapy; thereby treating a cancer in a subject.

According to another aspect, there is provided a method of increasing efficacy of an anti-PD-L1/PD-1 based therapy against a cancer cell expressing HLA-G, MHC-I or both, the method comprising contacting the cancer cell with an ILT2 antagonist.

According to some embodiments, the agent that inhibits ILT2 based immune suppression is an ILT2 antagonist.

According to some embodiments, the ILT2 antagonist is an antibody or antigen-binding fragment that specifically binds to ILT2 and inhibits ILT2-mediated immune cell suppression.

According to some embodiments, the antibody or antigen-binding fragment of the method is the antibody or antigen-binding fragment as described herein.

According to some embodiments, the anti-PD-L1/PD-1 based immunotherapy is an anti-PD-1 blocking antibody.

According to some embodiments, the cancer is refractory to anti-PD-L1/PD-1 based therapy.

According to some embodiments, the method of the invention further comprises administering to the subject an opsonizing agent.

According to some embodiments, the opsonizing agent is an EGFR inhibitor, optionally wherein the EGFR inhibitor is cetuximab.

According to another aspect, there is provided a pharmaceutical composition comprising an agent that binds to ILT2 and inhibits ILT2-mediated immune cell suppression, for use in combination with an anti-PD-L1/PD-1 based therapy to treat a subject suffering from cancer.

According to another aspect, there is provided a pharmaceutical composition comprising an antibody or antigen-binding fragment of the invention.

According to another aspect, there is provided a method for producing an agent, the method comprising:

obtaining an agent that binds to an ILT2 extracellular domain or fragment thereof, testing an ability of the agent to induce at least two of: increased phagocytosis of a cancer cell by macrophages, increased T cell activity against a cancer cell, increased generation of M1 macrophages, reduced generation of M2 macrophages, increased recruitment of dendritic cells to a tumor microenvironment, increased dendritic cell activation and increased natural killer (NK) cell cytotoxicity against a cancer cell and selecting at least one agent that induces at least two of the increased phagocytosis, the increased activity, the increased generation, the reduced generation, the recruitment, the increased activation, the decreased activity and the increased cytotoxicity; or culturing a host cell comprising one or more vectors comprising a nucleic acid sequence encoding an agent, wherein the nucleic acid sequence is that of an agent that was selected by:

i. obtaining an agent that binds to an ILT2 extracellular domain or fragment thereof;
ii. testing an ability of the agent to induce at least two of: increased phagocytosis of a cancer cell by macrophages, increased T cell activity against a cancer cell, increased generation of M1 macrophages, reduced generation of M2 macrophages, increased recruitment of dendritic cells to a tumor microenvironment, increased dendritic cell activation and increased natural killer (NK) cell cytotoxicity against a cancer cell; and
iii. selecting at least one agent that increases at least two of the increased phagocytosis, the increased activity, the increased generation, the reduced generation, the recruitment, the increased activation, the decreased activity and the increased cytotoxicity;

thereby producing an agent.

According to some embodiments, the method of the invention comprises testing an ability of the agent to induce at least three of: increased phagocytosis of a cancer cell by macrophages, increased T cell activity against a cancer cell, increased generation of M1 macrophages, reduced generation of M2 macrophages, increased recruitment of dendritic cells to a tumor microenvironment, increased dendritic cell activation and increased natural killer (NK) cell cytotoxicity against and selecting at least one agent that induces at least three.

According to another aspect, there is provided a method for producing an agent, the method comprising:

obtaining an agent that binds to an ILT2 extracellular domain or fragment thereof, testing an ability of the agent to increase efficacy of an anti-PD-L1/PD-1 based therapy against a cancer cell and selecting at least one agent that increases the efficacy of an anti-PD-L1/PD-1 based therapy; or culturing a host cell comprising one or more vectors comprising a nucleic acid sequence encoding an agent, wherein the nucleic acid sequence is that of an agent that was selected by:

i. obtaining an agent that binds to an ILT2 extracellular domain or fragment thereof;
ii. testing an ability of the agent to increase efficacy of an anti-PD-L1/PD-1 based therapy against a cancer cell; and
iii. selecting at least one agent that increases efficacy of an anti-PD-L1/PD-1 based therapy against a cancer cell;

thereby producing an agent.

According to some embodiments, the increasing efficacy comprises a synergistic increase in pro-inflammatory cytokine secretion or wherein the increased cytotoxicity comprises an increase in pro-inflammatory cytokine secretion.

According to some embodiments, the pro-inflammatory cytokine is selected from GM-CSF, TNFα and IFNγ.

According to some embodiments, the increasing efficacy comprises a synergistic increase in T cell activation, cytotoxicity or both.

According to some embodiments, the increase in T cell activation, cytotoxicity or both comprises increased membranal CD107a expression.

According to some embodiments, the increasing efficacy comprises converting a cancer refractory to anti-PD-L1/PD-1 based therapy to a cancer that responds to anti-PD-L1/PD-1 based therapy.

According to some embodiments, the cancer cell is an HLA-G or MHC-I expressing cancer.

According to another aspect, there is provided a method for producing an agent, the method comprising:

obtaining an agent that binds to an ILT2 extracellular domain or fragment thereof, testing an ability of the agent to inhibit interaction between ILT2 and B2M and selecting at least one agent that inhibits interaction between ILT2 and B2M: or culturing a host cell comprising one or more vectors comprising a nucleic acid sequence encoding an agent, wherein the nucleic acid sequence is that of an agent that was selected by.

i. obtaining an agent that binds to an ILT2 extracellular domain or fragment thereof;
ii. testing an ability of the agent to inhibit interaction between ILT2 and B2M; and
iii. selecting at least one agent that inhibits interaction between ILT2 and B2M;

thereby producing an agent.

According to another aspect, there is provided a method for producing an agent, the method comprising:

obtaining an agent that binds to an ILT2 epitope within a sequence of human ILT2 selected from SEQ ID NO: 41, 42, 43 and 44, or culturing a host cell comprising one or more vectors comprising a nucleic acid sequence encoding an agent, wherein the nucleic acid sequence is that of an agent that was selected by obtaining an agent that binds to an ILT2 epitope within a sequence of human ILT2 selected from SEQ ID NO: 41, 42, 43 and 44; thereby producing an agent.

According to another aspect, there is provided a nucleic acid molecule encoding an antibody or antigen-binding fragment of the invention.

According to some embodiments, the nucleic acid molecule is an expression vector.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1. Histograms depicting the expression of ILT2 on lymphocytes. Commercial antibody #1 at a 5 μg/mL final concentration was used. Binding is depicted as black histogram while isotype control staining is shown with a light grey histogram.

FIG. 2. Histograms depicting expression of ILT2 on various immune cells. Commercial antibody #1 at a 5 μg/mL final concentration was used. Binding is depicted as black histogram while isotype control staining is shown with light grey histogram.

FIGS. 3A-3C. (3A) Table of cancer indications from the TCGA database in which ILT2 RNA is over-expressed (3B) Dot plot of correlation between MDSC enrichment in tumors and ILT2 expression. A bar graph depicting the correlation between M2 enrichment and ILT2 expression is also presented. (3C). Scatter plot of the percent of various immune cells which express ILT2 in different tumors.

FIG. 6. Sequences of the heavy and light chains of three anti-ILT2 antibodies. CDRs as determined by the KABAT system are underlined or shown in red.

FIGS. 7A-7E. (7A) Table of antibody binding values to ILT2 and ILT2 family members. (7B) Histograms of antibody binding to ILT2 on the cell surface of BW cells transfected with human ILT2. (7C) Line graph of the binding of chimeric and humanized 19E3 (left panel) and of chimeric and humanized 15G8 (right panel) to ILT2 expressed on the surface of BW cells transfected with human ILT2. (7D) Immunostaining on gastric cancer samples with the 19E3 antibody. (7E) Scatter plot of percent of various immune cells which express ILT2 in PBMC samples from healthy controls and cancer patients using the 15G8 humanized antibody.

FIGS. 11A-11H. (11A-11B) Bar graphs of percent cytotoxicity from NK cell line cells cocultured with various cancer cell lines expressing (11A) HLA-G and (11B) MHC-I in the presence of ILT2 antibodies. (11C-11D) Bar graphs of (11C) Granzyme B and (11D) IFNγ secretion from NK cell line cells co-cultured with H&N cancer and melanoma cells respectively in the presence of the 15G8 ILT2 antibodies. (11E-11F) Bar graphs of (11E) IFNγ expression and (11F) CD107A expression in ILT2 positive primary NK cells incubated with target cancer cells in the presence of ILT2 antibodies. (11G-11H) Scatter plots of individual expression showing correlation of ILT2 positive cells and (11G) IFNγ expression and (11H) CD107A expression in response to ILT2 antibodies.

FIGS. 18A-18F. (18A) Partial sequence of ILT2 showing residues with significant predicted binding. These residues are divided in four categories as a function of their raw probability to belong to the epitope, from violet for the highest probability, to light cyan for the lowest probability (but still significant). Stars indicate locations of selected mutations. (18B-18C) 3D renderings of ILT2 surface structure showing (18B) the location of the residues from 18A and (18C) the four main interaction regions on ILT2. (18D-18F) 3D ribbon or surface diagrams of ILT2 showing (18D) the epitope of the 15G8 antibody (yellow/pink) and the epitope of the 3H5, 12D12 and 27H5 antibodies from WO2020/136145 (red), as well as a secondary epitope of the 3H5 antibody (dark blue) (18E-18F) and interaction of the 15G8 epitope on ILT2 (pink) with B2M (lilac) in complex with (ISE) HLA-A (blue) or (18F) HLA-G (blue).

DETAILED DESCRIPTION OF THE INVENTION

Figure 3C:
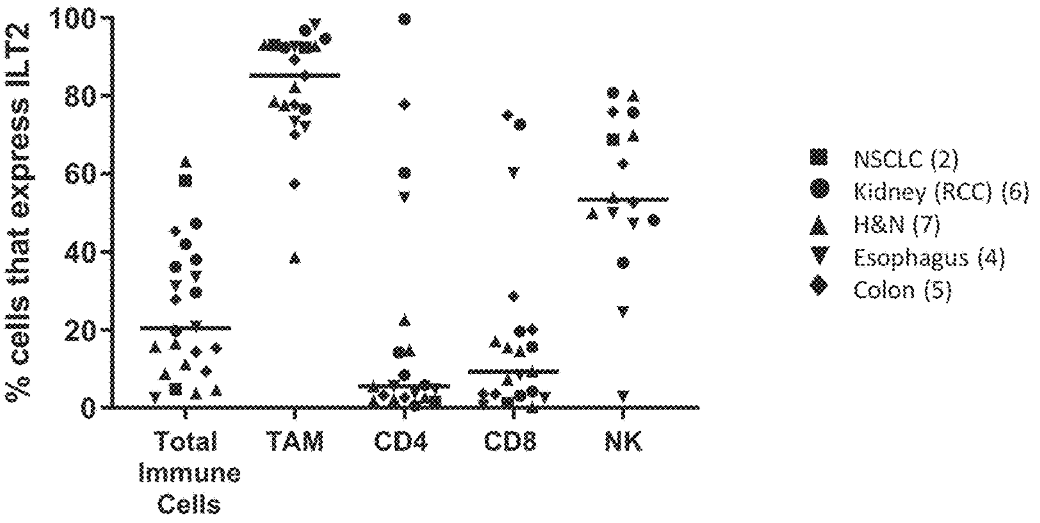

The present invention is directed to a monoclonal antibody or antigen-binding fragments and pharmaceutical compositions that bind ILT2 and inhibit ILT2-mediated immune suppression. Methods of treating cancer and enhancing PD-1/PD-L1 immunotherapy are also provided.

The invention is at least partially based on the surprising finding that ILT2 antagonism acts synergistically with PD-1 and PD-L1-based immunotherapies to combat cancer cells. Specifically, it was found that ILT2 blocking antibodies in combination with anti-PD-1 antibodies increased pro-inflammatory cytokine secretion by immune cells. This increase was not merely additive, but rather greater than the sum of the effects of each agent individually. Indeed, for at least one cytokine a de novo increase was observed, where neither agent alone had had any effect. This combined treatment allows for conversion of PD-1/PD-L1 refractory cancers to be made responsive.

It was further surprisingly found that the level of ILT2 expression in the immune cells of patients was correlated to the effectiveness of the ILT2 blocking therapy. Responders to the therapy had high ILT2 levels, while non-responders had low ILT2 levels. In particular, circulating CD8 positive T cells were predictive of treatment outcome.

Lastly, the antibodies of the invention were found to bind a unique epitope within the ILT2 interdomain between the D1 and D2 domains. This region is known to be the interaction domain between ILT2 and B2M and the antibodies of the invention are the first known antibodies to directly block this interaction. Further, the antibodies of the invention were found to have immuno-stimulating effects not reported for other anti-ILT2 antibodies. The antibodies were able to modulate the immunosurveillance of T cells, NK cells, dendritic cells and macrophages against HLA-G and MHC-I expressing cancer cells. In particular, for the first time an anti-ILT2 antibody used as a monotherapy was able to enhance phagocytosis of cancer cells.

Antibodies

In a first aspect, there is provided an antibody or antigen-binding fragment comprising three heavy chain CDRs (CDR-H) and three light chain CDRs (CDR-L), wherein: CDR-H1 comprises the amino acid sequence set forth in SEQ ID NO: 1 (DHTIH), CDR-H2 comprises the amino acid sequence as set forth in SEQ ID NO: 2 (YIYPRDGSTKYNEKFKG), CDR-H3 comprises the amino acid sequence as set forth in SEQ ID NO: 3 (TWDYFDY), CDR-L1 comprises the amino acid sequence as set forth in SEQ ID NO: 4 (RASESVDSYGNSFMH), CDR-L2 comprises the amino acid sequence as set forth in SEQ ID NO: 5 (RASNLES), and CDR-L3 comprises the amino acid sequence as set forth in SEQ ID NO: 6 (QQSNEDPYT).

In another aspect, there is provided an antibody or antigen-binding fragment comprising three heavy chain CDRs (CDR-H) and three light chain CDRs (CDR-L), wherein: CDR-H1 comprises the amino acid sequence set forth in SEQ ID NO: 7 (GYTFTSYGIS), CDR-H2 comprises the amino acid sequence as set forth in SEQ ID NO: 8 (EIYPGSGNSYYNEKFKG), CDR-H3 comprises the amino acid sequence as set forth in SEQ ID NO: 9 (SNDGYPDY), CDR-L1 comprises the amino acid sequence as set forth in SEQ ID NO: 10 (KASDHINNWLA), CDR-L2 comprises the amino acid sequence as set forth in SEQ ID NO: 11 (GATSLET), and CDR-L3 comprises the amino acid sequence as set forth in SEQ ID NO: 12 (QQYWSTPWT).

In another aspect, there is provided an antibody or antigen-binding fragment comprising three heavy chain CDRs (CDR-H) and three light chain CDRs (CDR-L), wherein: CDR-H1 comprises the amino acid sequence set forth in SEQ ID NO: 13 (SGYYWN), CDR-H2 comprises the amino acid sequence as set forth in SEQ ID NO: 14 (YISYDGSNNYNPSLKN), CDR-H3 comprises the amino acid sequence as set forth in SEQ ID NO: 15 (GYSYYYAMDX), CDR-L1 comprises the amino acid sequence as set forth in SEQ ID NO: 16 (RTSQDISNYLN), CDR-L2 comprises the amino acid sequence as set forth in SEQ ID NO: 17 (YTSRLHS), and CDR-L3 comprises the amino acid sequence as set forth in SEQ ID NO: 18 (QQGNTLPT), wherein X is selected from and A, C and S.

In some embodiments, SEQ ID NO: 15 is GYSYYYAMDA (SEQ ID NO: 25). In some embodiments, SEQ ID NO: 15 is SEQ ID NO: 25 and the antibody or antigen-binding fragment is a humanized antibody. In some embodiments, SEQ ID NO: 15 is GYSYYYAMDS (SEQ ID NO: 26). In some embodiments, SEQ ID NO: 15 is SEQ ID NO: 26 and the antibody or antigen-binding fragment is a humanized antibody. In some embodiments, SEQ ID NO: 15 is GYSYYYAMDC (SEQ ID NO: 27). In some embodiments. SEQ ID NO: 15 is SEQ ID NO: 27 and the antibody or antigen-binding fragment is a murine antibody.

In another aspect, there is provided an antibody or antigen-binding fragment that binds a human leukocyte immunoglobulin-like receptor subfamily B member 1 (ILT2) interdomain between domains D1 and D2.

In another aspect, there is provided an antibody or antigen-binding fragment that binds an ILT2 epitope within a sequence of ILT2 selected from VKKGQFPIPSITWEH (SEQ ID NO: 41), LELVVTGAYIKPTLS (SEQ ID NO: 42), VILQCDSQVAFDGFS (SEQ ID NO: 43) and WYRCYAYDSNSPYEW (SEQ ID NO: 44).

In another aspect, there is provided an antibody or antigen-binding fragment that binds ILT2 and inhibits interaction between ILT2 and beta-2-microglobulin (B2M).

In another aspect, there is provided an antibody or antigen-binding fragment that binds ILT2 and induces in a subject suffering from cancer at least one of;

a. increased natural killer (NK) cell cytotoxicity:
b. increased T cell cytotoxicity, proliferation or both:
c. increased macrophage phagocytosis, increased generation of M1 inflammatory macrophages, decreased generation of M2 suppressor macrophages or a combination thereof; and
d. increased dendritic cell homing to a tumor of said cancer, increased dendritic cell activation or a combination thereof.

In some embodiments, the antibody is a monoclonal antibody. In some embodiments, the antibody is a polyclonal antibody. In some embodiments, the antibody is a human antibody. In some embodiments, the antibody is a murine antibody. In some embodiments, the antibody is a humanized antibody. As used herein, a "humanized" antibody refers to an antibody with a human backbone, but which has CDRs that are derived or taken from a non-human antibody. In some embodiments, during humanization the CDRs may become altered but are generally still derived from the CDRs of the non-human antibody. In some embodiments, the antigen-binding fragment is a single chain antibody. In some embodiments, antigen-binding fragment is a single domain antibody.

In some embodiments, the antibody or antigen-binding fragment binds leukocyte immunoglobulin-like receptor subfamily B member 1 (ILT2). In some embodiments, ILT2 is human ILT2. In some embodiments, ILT2 is mammalian ILT2. In some embodiments, ILT2 is primate ILT2. In some embodiments, ILT2 is murine ILT2. In some embodiments, the antibody or antigen-binding fragment binds an extracellular domain of ILT2. In some embodiments, the antibody or antigen-binding fragment binds the ligand pocket of ILT2. In some embodiments, the ligand is B2M. In some embodiments, the ligand is not an HLA. In some embodiments, the ligand is HLA. In some embodiments, the HLA is HLA-G. In some embodiments, the ligand is not an MHC. In some embodiments, the ligand is MHC. In some embodiments, the MHC is MHC class I (MHC-I). In some embodiments, the antibody or antigen-binding fragment binds an ILT2 interdomain. In some embodiments, the interdomain is the interface between the D1 and D2 domains. In some embodiments, the interdomain is the hinge domain between the D1 and D2 domains. In some embodiments, the interdomain does not comprise the N-terminal domain of D1. In some embodiments, the interdomain is from amino acids 54-184 of SEQ ID NO. 31. In some embodiments, amino acids 54-184 of SEQ ID NO: 31 comprise the interdomain. In some embodiments, the interdomain is from amino acids 90-184 of SEQ ID NO: 31. In some embodiments, amino acids 90-184 comprise the interdomain. In some embodiments, the antibody or antigen-binding fragment binds an epitope within the interdomain. In some embodiments, the epitope comprises at least 25, 30, 35, 40, 45, 50, 55, 60, 65, 70, 75, 80, 85, 90, 95, 97, 99 or 100% of the interdomain. Each possibility represents a separate embodiment of the invention. In some embodiments, epitope is within D2. In some embodiments, the antibody or antigen binding domain binds an epitope in D2. In some embodiments, the epitope is at least partially in D2. In some embodiments, the antibody or antigen binding domain binds an epitope at least partially in D2. In some embodiments, the epitope spans D1 and D2. In some embodiments, the antibody or antigen-binding fragment does not bind an ILT2 domain that interacts with the 3 domain of HLA-G.

In some embodiments, ILT2 is mammalian ILT2. In some embodiments, ILT2 is human ILT2. In some embodiments, ILT2 has the amino acid sequence provided in NCBI Reference Sequence: NP_006660.4. In some embodiments, ILT2 has the following amino acid sequence:

(SEQ ID NO: 31)

MTPILTVLICLGLSLGPRTHVQAGHLPKPTLWAEPGSVITQGSPVTLRC

QGGQETQEYRLYREKKTALWITRIPQELVKKGQFPIPSITWEHAGRYRC

YYGSDTAGRSESSDPLELVVTGAYIKPTLSAQPSPVVNSGGNVILQCDS

QVAFDGFSLCKEGEDEHPQCLNSQPHARGSSRAIFSVGPVSPSRRWWYR

CYAYDSNSPYEWSLPSDLLELLVLGVSKKPSLSVQPGPIVAPEETLTLQ

CGSDAGYNRFVLYKDGERDFLQLAGQPQPAGLSQANFTLGPVSRSYGGQ

YRCYGAHNLSSEWSAPSDPLDILIAGQFYDRVSLSVQPGPTVASGENVT

LLCQSQGWMQTFLLTKEGAADDPWRLRSTYQSQKYQAEFPMGPVTSAHA

GTYRCYGSQSSKPYLLTHPSDPLELVVSGPSGGPSSPTTGPTSTSGPED

QPLTPTGSDPQSGLGRHLGVVIGILVAVILLLLLLLLLFLILRHRRQGK

HWTSTQRKADFQHPAGAVGPEPTDRGLQWRSSPAADAQEENLYAAVKHT

QPEDGVEMDTRSPHDEDPQAVTYAEVKHSRPRREMASPPSPLSGEFLDT

KDRQAEEDRQMDTEAAASEAPQDVTYAQLHSLTLRREATEPPPSQEGPS

PAVPSIYATLAIH.

In some embodiments, ILT2 has the amino acid sequence provided in NCBI Reference Sequence: NP_001075106.2. In some embodiments, ILT2 has the amino acid sequence provided in NCBI Reference Sequence: NP_001075107.2. In some embodiments, ILT2 has the amino acid sequence provided in NCBI Reference Sequence: NP_001075108.2. In some embodiments, ILT2 has the amino acid sequence provided in NCBI Reference Sequence: NP_001265328.2.

In some embodiments, the D1 domain of ILT2 comprises or consists of the amino acid sequence GHLPKPTLWAEPGSVITQGSPVTLRCQGGQETQEYRLYREKKTALWITRIPQELVK KGQFPIPSITWEHAGRYRCYYGSDTAGRSESSDPLELVVTGA (SEQ ID NO: 46). In some embodiments, the D1 domain of ILT2 comprises or consists of amino acids 24-121 of SEQ ID NO: 31. In some embodiments, the D2 domain of ILT2 comprises or consists of the amino acid sequence (SEQ ID NO: 47)

YIKPTLSAQPSPVVNSGGNVILQCDSQVAFDGFSLCKEGEDEHPQCLNS
QPHARGSSRAIFSVGPVSPSRRWWYRCYAYDSNSPYEWSLPSDLLELLV
LGV.

In some embodiments, the D2 domain of ILT2 comprises or consists of amino acids 122-222 of SEQ ID NO: 31. In some embodiments, the interdomain of ILT2 comprises amino acids Gln41, Lys65, Trp90, Gly120, Ala121, Val122, Ile123, Gln148, Val149, Ala150, Phe151, Asp201, Asn203 and Glu207 of SEQ ID NO: 31. In some embodiments, the epitope comprises amino acids Gln41, Lys65, Trp90, Gly 120, Ala121, Val122, Ile123, Gln148, Val149, Ala150, Phe151, Asp201, Asn203 and Glu207 of SEQ ID NO: 31. In some embodiments, the epitope comprises at least 5, 6, 7, 8, 9, 10, 11, 12, 13 or 14 amino acids selected from amino acids Gln41, Lys65, Trp90, Gly120, Ala121, Val122, Ile123, Gln148, Val149, Ala150, Phe151, Asp201, Asn203 and Glu207 of SEQ ID NO: 31. In some embodiments, the epitope comprises at least 10 amino acids selected from amino acids Gln41, Lys65, Trp90, Gly120, Ala121, Val122, Ile123, Gln148, Val149, Ala150, Phe151, Asp201, Asn203 and Glu207 of SEQ ID NO: 31. In some embodiments, the antibody or antigen-binding fragment binds the ILT2 epitope provided in SEQ ID NO: 41. In some embodiments, the antibody or antigen-binding fragment binds the ILT2 epitope provided in SEQ ID NO: 42. In some embodiments, the antibody or antigen-binding fragment binds the ILT2 epitope provided in SEQ ID NO: 43. In some embodiments, the antibody or antigen-binding fragment binds the ILT2 epitope provided in SEQ ID NO: 44. In some embodiments, the antibody or antigen-binding fragment binds a 3-dimensional epitope comprising at least two of SEQ ID NO: 41, 42, 43 and 44. In some embodiments, the 3-dimensional epitope comprise at least 3 of SEQ ID NO: 41, 42, 43 and 44. In some embodiments, the 3-dimensional epitope comprise SEQ ID NO: 41, 42, 43 and 44.

In some embodiments, the antibody or antigen-binding fragment binds an ILT2 epitope comprising a residue of ILT2 selected from Q18, G19, K42, L45, S64, I65, T66, W67, E68, G97, A98, Y99, I100, Q125, V126, A127, F128, D178, N180, S181, and E184. In some embodiments, the antibody or antigen-binding fragment binds an ILT2 epitope comprising a residue of ILT2 selected from G97, A98, Y99, I100, Q125 and V126. In some embodiments, the antibody or antigen-binding fragment binds an ILT2 epitope comprising a plurality of residues of ILT2 selected from Q18, G19, K42, L45, S64, I65, T66, W67, E68, G97, A98, Y99, I100, Q125, V126, A127, F128, D178, N180, S181, and E184. In some embodiments, the antibody or antigen-binding fragment binds an ILT2 epitope comprising a plurality of residues of ILT2 selected from G97, A98, Y99, I100, Q125 and V126. In some embodiments, the antibody or antigen-binding fragment binds at least 1, 2, 3, 4, 5, 6, 7, 8, 9, 10, 11, 12, 13, 14, 15, 16, 17, 18, 19, 20, or 21 residues selected from Q18, G19, K42, L45, S64, I65, T66, W67, E68, G97, A98, Y99, I100, Q125, V126, A127, F128, D178, N180, S181, and E184. Each possibility represents a separate embodiment of the invention. In some embodiments, the antibody or antigen-binding fragment binds at least 1, 2, 3, 4, 5, or 6 residues selected from G97, A98, Y99, I100, Q125 and V126. Each possibility represents a separate embodiment of the invention. In some embodiments, the antibody or antigen-binding fragment binds G97, A98, Y99, I100, Q125 and V126. It will be understood that the number used herein is with respect to SEQ ID NO: 31.

In some embodiments, the antibody or antigen-binding fragment is an ILT2 antagonist. In some embodiments, the antibody or antigen-binding fragment is not an ILT2 agonist. In some embodiments, antagonism is of ILT2-mediated immune suppression. In some embodiments, the antibody or antigen-binding fragment inhibits ILT2-mediated immune suppression. In some embodiments, the antibody or antigen-binding fragment inhibits ILT2 signaling.

In some embodiments, the antibody or antigen-binding fragment inhibits interaction between ILT2 and B2M. In some embodiments, the interaction is direct interaction. In some embodiments, the antibody or antigen-binding fragment inhibits ILT2 contact with B2M. In some embodiments, the contact is direct contact. In some embodiments, the antibody or antigen-binding fragment inhibits interaction between ILT2 and HLA, MHC or both. In some embodiments, the antibody or antigen-binding fragment inhibits interaction between ILT2 and HLA, MHC or both via inhibition of ILT2 interaction with B2M. In some embodiment, the interaction is mediated by B2M. In some embodiments, the antibody indirectly inhibits interaction with HLA, MHC or both via inhibition of interaction with B2M. In some embodiments, the interaction is B2M mediated interaction. In some embodiments, the antibody or antigen-binding fragment inhibits interaction between ILT2 and a B2M/HLA complex. In some embodiments, the antibody or antigen-binding fragment inhibits interaction between ILT2 and a B2M/MHC complex. In some embodiments, the complex comprises a B2M monomer. In some embodiments, the complex comprises an HLA or MHC monomer. In some embodiments, the complex comprises a B2M dimer. In some embodiments, the complex comprises an HLA or MHC dimer.

In some embodiments, ILT2-mediated immune suppression is suppression of an immune cell. In some embodiments, the immune cell is selected from a T cell, a macrophage, a dendritic cell and a natural killer (NK) cell. In some embodiments, ILT2-mediated immune suppression is suppression of a T cell, a macrophage, a dendritic cell and an NK cell. In some embodiments, ILT2-mediated immune suppression is suppression of a T cell, a macrophage and an NK cell. In some embodiments, the T cell is a CD8 positive T cell. In some embodiments, the T cell is a $T_{EMRA}$ cell (terminally differentiated effector memory cell re-expressing CD45RA). In some embodiments, the immune cell is selected from a CD8 positive T cell, a $T_{EMRA}$ cell, a dendritic cell, a macrophage and a natural killer (NK) cell. In some embodiments, the immune cell is a T cell. In some embodiments, the immune cell is an NK cell. In some embodiments, the immune cell is a macrophage. In some embodiments, the macrophage is a tumor-associated macrophage (TAM). In some embodiments, the immune cell is a dendritic cell. In some embodiments, the dendritic cell is a tolerogenic dendritic cell. In some embodiments, the immune cell is a peripheral blood immune cell. In some embodiments, the immune cell is a peripheral blood mononuclear cell (PBMC). In some embodiments, the immune cell is an intratumor immune cell. In some embodiments, the immune cell is an immune cell in the tumor microenvironment (TME). In some embodiments, ILT2-mediated immune suppression is suppression of macrophage phagocytosis. In some embodiments, ILT2-mediated immune suppression is suppression of NK cell cytotoxicity. In some embodiments, ILT2-mediated immune suppression is suppression of T cell cytotoxicity. In some embodiments, ILT2-mediated immune suppression is suppression of T cell proliferation. In some embodiments, ILT2-mediated immune suppression is suppression of immune cell proliferation.

In some embodiments, the antibody or antigen-binding fragment does not bind a member of the leukocyte immunoglobulin-like receptor subfamily B other than ILT2. In some embodiments, the antibody or antigen-binding fragment is specific to ILT2. In some embodiments, the antibody or antigen-binding fragment preferentially binds to ILT2. In some embodiments, the antibody or antigen-binding fragment does not inhibit a member of the leukocyte immunoglobulin-like receptor subfamily B other than ILT2.

As used herein, "increased binding efficacy" refers to a specific binding to a target or antigen that is greater than the binding of an isotype control. In some embodiments, increased binding is an increase of at least 10, 20, 30, 40, 50, 60, 70, 80, 90, 100, 200, 300, 400, 500, 600, 700, 800, 900, or 1000% of binding efficacy. Each possibility represents a separate embodiment of the invention. In some embodiments, increased binding is the presence of binding as compared to an isotype control that has no binding. Binding of an antibody to a specific domain will be well known to a person of skill in the art. Antibody binding can be assayed in any way known to one skilled in the art, including but not limited to: x-ray crystallography, immunoprecipitation, immunoblotting, competition assays, and kinetic exclusion assays. In some embodiments, increased binding efficacy is specific binding.

An antibody or antigen-binding fragment, variant, or derivative disclosed herein can be said to bind a target antigen, e.g., ILT2, with an on rate (k(on)) of greater than or equal to $10^3$ $M^{-1}sec^{-1}$, $5\times10^3$ $M^{-1}$ $sec^{-1}$, $10^4$ $M^{-1}$ $sec^{-1}$ or $5\times10^4$ $M^{-1}$ $sec^{-1}$. Each possibility represents a separate embodiment of the invention. An antibody or antigen-binding fragment, variant, or derivative disclosed herein can be said to bind a target antigen with an affinity of $10^{-6}$ M or greater, whereas most antibodies have typical affinities of $10^{-9}$ M.

In some embodiments, the antibody or antigen-binding fragment comprises a heavy chain comprising the amino acid sequence of SEQ ID NO: 19 (QVQLQQSDAELVKPGASVKISCKVSGYTFTDHTIHWMKQRPEQGLEWIGYIYPRD GSTKYNEKFKGKATLTADKSSSTAYMQLNSLTSEDSAVYFCARTWDYFDYWGQG TTLTVSS). In some embodiments, the antibody or antigen-binding fragment comprises a heavy chain comprising the amino acid sequence of SEQ ID NO: 21 (QVQLQQSGAELARPGASVKLSCKASGYTFTSYGISWVKQRTGQGLEWVGEIYPGS GNSYYNEKFKGKATLTADKSSSTAYMELRSLTSEDSAVYFCARSNDGYPDYWGQG TTLTVSS). In some embodiments, the antibody or antigen-binding fragment comprises a heavy chain comprising the amino acid sequence of SEQ ID NO: 23 (DVQLQGSGPGLVKPSETLSLTCSVTGYSITSGYYWNWIRQFPGKKLEWMGYISYD GSNNYNPSLKNRITISRDTSKNQFSLKLNSVTAADTATYYCAHGYSYYYAMDXWG QGTSVTVSS), wherein X is selected from A, C and S.

In some embodiments, the antibody or antigen-binding fragment comprises a light chain comprising the amino acid sequence of SEQ ID NO: 20 (DIVLTQSPASLAVSLGQRATISCRASESVDSYGNSFMHWYQQKPGQPPKLLIYRASN LESGIPARFSGSGSRTDFTLTINPVEADDVATYYCQQSNEDPYTFGGGTKLEIK). In some embodiments, the antibody or antigen-binding fragment comprises a light chain comprising the amino acid sequence of SEQ ID NO: 22 (DIQMTQSSSYLSVSLGGRVTITCKASDHINNWLAWYQQKPGNAPRLLISGATSLET GVPSRFSGSGSGKDYTLSITSLQTEDVATYYCQQYWSTPWTFGGGTKLEIK). In some embodiments, the antibody or antigen-binding fragment comprises a light chain comprising the amino acid sequence of SEQ ID NO: 24 (DIQMTQSPSSLSASVGDRVTITCRTSQDISNYLNWYQQKPGKAVKLLISYTSRLHSGV PSRFSGSGSGTDYTLTISSLQPEDFATYYCQQGNTLPTFGQGTKLEIK. In some embodiments, the antibody or antigen-binding fragment comprises a light chain comprising the amino acid sequence of SEQ ID NO: 45 (DIQMTQTTSSLSASLGDRVTISCRTSQDISNYLNWYQQKPDGTVKLLISYTSRLHSGV PSRFSGSGSGTDYSLTISNLEQEDIATYFCQQGNTLPTFGSGTKLEIK).

In some embodiments. SEQ ID NO: 23 is DVQLQGSGPGLVKPSETLSLTCSVTGYSITSGYYWNWIRQFPGKKLEWMGYISYDG SNNYNPSLKNRITIS- RDTSKNQFSLKLNSVTAADTATYYCAHGYSYYYAMDAWGQ GTSVTVSS (SEQ ID NO: 28). In some embodiments, SEQ ID NO: 23 is SEQ ID NO: 28 and the antibody or antigen-binding fragment is humanized. In some embodiments, SEQ ID NO: 23 is DVQLQGSGPGLVKPSETLSLTCSVTGYSITSGYYWNWIRQFPGKKLEWMGYISYDG SNNYNPSLKNRITISRDTSKNQFSLKLNSVTAADTATYYCAHGYSYYYAMDSWGQ GTSVTVSS (SEQ ID NO: 29). In some embodiments, SEQ ID NO: 23 is SEQ ID NO: 29 and the antibody or antigen-binding fragment is humanized. In some embodiments, SEQ ID NO: 23 is DVQLQGSGPGLVKPSQSLSLTCSVTGYSITSGYYWNWIRQFPGNKLEWMGYISYDG SNNYNPSLKNRISITRDTSKNQFFLKLNSVTSEDTATYYCAHGYSYYYAMDCWGQ GTSVTVSS (SEQ ID NO: 30). In some embodiments. SEQ ID NO: 23 is SEQ ID NO: 30 and the antibody or antigen-binding fragment is murine.

In some embodiments, the antibody or antigen-binding fragment of the invention is for use in treating or ameliorating cancer in a subject in need thereof. In some embodiments, the cancer is an HLA-G positive cancer. In some embodiments, the cancer is an MHC-I positive cancer. In some embodiments, the cancer is an HLA-G expressing cancer. In some embodiments, the cancer is an MHC-I expressing cancer. In some embodiments, an antibody or antigen-binding fragment of the invention is for use in shifting a tumor microenvironment from immunosuppressive to immuno-stimulatory. In some embodiments, said shifting the tumor microenvironment comprises one or more of: inducing/enhancing an anti-tumor T-cell response, increasing T-cell proliferation, reducing cancer-induced suppressor myeloid activity, increasing dendritic cell (DC) activation, increasing dendritic cell homing to the tumor, increasing macrophage phagocytosis, increasing generation of M1 macrophages, decreasing generation of M2 macrophages and increasing NK cell activity. In some embodiments, antibody or antigen-binding fragment of the invention is for use in increasing a T-cell response against a cancer cell. In some embodiments, the T cell response comprises increased pro-inflammatory cytokine secretion. In some embodiments, T cell response comprises increased cytotoxicity. In some embodiments, the T cell response comprises increased T cell proliferation. In some embodiments, antibody or antigen-binding fragment of the invention is for use in increasing macrophage phagocytosis of a cancer cell. In some embodiments, antibody or antigen-binding fragment of the invention is for use increasing dendritic cell homing to a tumor or cancer. In some embodiments, antibody or antigen-binding fragment of the invention is for use in increasing macrophage phagocytosis. In some embodiments, antibody or antigen-binding fragment of the invention is for use increasing macrophage phagocytosis of the cancer. In some embodiments, antibody or antigen-binding fragment of the invention is for use in increasing generation of M1 macrophages. In some embodiments, antibody or antigen-binding fragment of the invention is for use in decreasing generation of M2 macrophages. In some embodiments, antibody or antigen-binding fragment of the invention is for use in increasing NK cell cytotoxicity against a cancer cell. In some embodiments, antibody or antigen-binding fragment of the invention is for use in reducing cancer-induced suppressor myeloid activity. In some embodiments, antibody or antigen-binding fragment of the invention is for use in reducing tolerogenic dendritic cell (DC) activity. In some embodiments, the antibody or antigen-binding fragment of the invention is for increasing M1 monocyte activity or number. In some embodiments, the antibody or antigen-binding fragment of the invention is for decreasing M2 monocyte activity or number. In some embodiments, the antibody or antigen-binding fragment of the invention is for increasing generation of M1 macrophages. In some embodiments, the antibody or antigen-binding fragment of the invention is for decreasing generation of M2 macrophages. In some embodiments, M1 monocytes/macrophages are inflammatory macrophages/monocytes. In some embodiments. M2 monocytes/macrophages are suppressor macrophages/monocytes. In some embodiments, the antibody or antigen-binding fragment of the invention is for increasing DC number in a tumor. In some embodiments, the antibody or antigen-binding fragment of the invention is for increasing recruitment of DCs to a tumor. In some embodiments, the antibody or antigen-binding fragment of the invention is for increasing DC recruitment to a tumor. In some embodiments, the antibody or antigen-binding fragment of the invention is for increasing DC activation. In some embodiments, increasing DC activation comprises decreasing tolerogenic dendritic cell activity. In some embodiments, the antibody or antigen-binding fragment of the invention is for increasing antigen presentation. In some embodiments, to a tumor is to a tumor microenvironment (TME).

In some embodiments, the antibody or antigen-binding fragment induces in a subject at least 1, 2, 3, 4, 5, 6, 7, 8, 9 or 10 anti-cancer effects. Each possibility represents a separate embodiment of the invention. In some embodiments, the antibody or antigen-binding fragment induces in a subject at least 2 effects. In some embodiments, the antibody or antigen-binding fragment induces in a subject at least 3 effects. In some embodiments, the antibody or antigen-binding fragment induces in a subject at least 4 effects. In some embodiments, the effects are selected from: increased NK cell cytotoxicity, increased T cell cytotoxicity, increased T cell proliferation, increased macrophage phagocytosis, increased generation of M1 macrophages, decreased generation of M2 macrophages, increased dendritic cell homing to a tumor of the cancer, and increased dendritic cell activation. In some embodiments, the effects are selected from: a) increased NK cell cytotoxicity; b) increased T cell cytotoxicity, proliferation or both; c) increased macrophage phagocytosis, increased generation of M1 macrophages, decreased generation of M2 macrophages or a combination thereof; and d) increased dendritic cell homing to a tumor of the cancer, increased dendritic cell activation and a combination thereof. In some embodiments, cytotoxicity is cytotoxicity against a cancer. In some embodiments, phagocytosis is phagocytosis of a cancer or cancer cells. In some embodiments, the antibody or antigen-binding fragment induces in a subject an anti-cancer effect on T cells, NK cells, dendritic cell and macrophages. In some embodiments, the antibody or antigen-binding fragment induces in a subject an anti-cancer effect on at least 3 of T cells, NK cells, dendritic cell and macrophages. In some embodiments, the antibody or antigen-binding fragment induces the effect as a monotherapy. In some embodiments, the antibody or antigen-binding fragment induces the effect without combination In some embodiments, increased cytotoxicity comprises increased pro-inflammatory cytokine secretion. Pro-inflammatory cytokines are well known in the art and include, but are not limited to: IL-1, IL-1B, IL-6, TNFα, IFNγ, MCP-1, IL-12, IL-18, IL-2, IL-15, IL-17, IL-21 and granulocyte-macrophage colony stimulating factor (GM-CSF). In some embodiments, the pro-inflammatory cytokine is selected from IL-6, interferon gamma (IFNγ) and GM-CSF. In some embodiments, the pro-inflammatory cytokine is GM-CSF.

An "anti-ILT2 antibody", "an antibody which recognizes ILT2", or "an antibody against ILT2" is an antibody that binds to the ILT2, with sufficient affinity and specificity. In some embodiments, an anti-ILT2 antibody has ILT2 as the antigen to which it binds.

An "antigen" is a molecule or a portion of a molecule capable of eliciting antibody formation and being bound by an antibody. An antigen may have one or more than one epitope. The specific reaction referred to above is meant to indicate that the antigen will react, in a highly selective manner, with its corresponding antibody and not with the multitude of other antibodies which may be evoked by other antigens.

The term "antigenic determinant" or "epitope" according to the invention refers to the region of an antigen molecule that specifically reacts with particular antibody. Peptide sequences derived from an epitope can be used, alone or in conjunction with a carrier moiety, applying methods known in the art, to immunize animals and to produce additional polyclonal or monoclonal antibodies. Immunoglobulin variable domains can also be analyzed using the IMGT information system (www://imgt.cines.fr/) (IMGT®/V-Quest) to identify variable region segments, including CDRs. See, e.g., Brochet, X. et al., Nucl. Acids Res. J6:W503-508 (2008).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In some embodiments, the antibody or antigen-binding fragment is for use in combination with another agent. In some embodiments, the use in combination with another agent is for treating an HLA-G and/or MHC-1 expressing cancer. In some embodiments, the agent is an opsonizing agent. In some embodiments, the agent is an anti-PD-1 and/or anti-PD-L1 agent. In some embodiments, the antibody or antigen-binding fragment is for use in combination with anti-PD-1/PD-L1 based therapy.

As used herein, an "opsonizing agent" is any agent that can bind to a target cell (e.g., a cancer cell, a cell harboring an intracellular pathogen, etc.) and opsonize the target cell. For example, any antibody that can bind to a target cell, where the antibody has an Fc region, is considered to be an agent that opsonizes a target cell. In some embodiments, an opsonizing agent is an antibody that induces antibody dependent cellular phagocytosis (ADCP). Examples of opsonizing agents include, but are not limited to anti-CD47 antibodies, anti-CD20 antibodies, anti-HER2 antibodies, anti-EGFR antibodies, anti-CD52 antibodies and anti-CD30 antibodies. In some embodiments, the opsonizing agent is selected from Rituximab, Trastuzumab, Pertuzumab, Herceptin, Cetuximab, Panitumumab, and Erbitux. In some embodiments, the opsonizing agent is an anti-EGFR antibody. In some embodiments, the opsonizing agent is Erbitux.

As used herein, an "anti-PD-1/PD-L1 therapy", and a "PD-1/PD-L1 therapy" are synonymous and used interchangeably and refer to a therapeutic regime that comprises blockade of the PD-1 and PD-L1 signaling axis. In some embodiments, the cancer is a PD-L1 positive cancer. In some embodiments, PD-1/PD-L1 therapy is PD-1/PD-L1 immunotherapy. In some embodiments, the PD-1/PD-L1 therapy is PD-1/PD-L1 blockade. In some embodiments, the PD-1/PD-L1 therapy is an agent that blocks PD-1 based immune inhibition. In some embodiments, the PD-1/PD-L1 therapy comprises an anti-PD-1 blocking antibody. In some embodiments, the PD-1/PD-L1 therapy comprises an anti-PD-L1 blocking antibody. In some embodiments, the PD-1/PD-L1 therapy increases immune surveillance. In some embodiments, the PD-1/PD-L1 therapy is an anti-cancer therapy. In some embodiments, the PD-1/PD-L1 therapy increases tumor immune surveillance. The term "antibody" (also referred to as an "immunoglobulin") is used in the broadest sense and specifically encompasses monoclonal antibodies and antibody fragments so long as they exhibit the desired biological activity. In certain embodiments, the use of a chimeric antibody or a humanized antibody is also encompassed by the invention.

The basic unit of the naturally occurring antibody structure is a heterotetrameric glycoprotein complex of about 150,000 Daltons, composed of two identical light (L) chains and two identical heavy (H) chains, linked together by both noncovalent associations and by disulfide bonds. Each heavy and light chain also has regularly spaced intra-chain disulfide bridges. Five human antibody classes (IgG, IgA, IgM, IgD and IgE) exist, and within these classes, various subclasses, are recognized based on structural differences, such as the number of immunoglobulin units in a single antibody molecule, the disulfide bridge structure of the individual units, and differences in chain length and sequence. The class and subclass of an antibody is its isotype.

The amino terminal regions of the heavy and light chains are more diverse in sequence than the carboxy terminal regions, and hence are termed the variable domains. This part of the antibody structure confers the antigen-binding specificity of the antibody. A heavy variable (VH) domain and a light variable (VL) domain together form a single antigen-binding site, thus, the basic immunoglobulin unit has two antigen-binding sites. Particular amino acid residues are believed to form an interface between the light and heavy chain variable domains (Chothia et al., J. Mol. Biol. 186, 651-63 (1985): Novotny and Haber, (1985) Proc. Natl. Acad. Sci. USA 82 4592-4596).

The carboxy terminal portion of the heavy and light chains form the constant domains i.e., CH1, CH2, CH3, CL. While there is much less diversity in these domains, there are differences from one animal species to another, and further, within the same individual there are several different isotypes of antibody, each having a different function.

The term "framework region" or "FR" refers to the amino acid residues in the variable domain of an antibody, which are other than the hypervariable region amino acid residues as herein defined. The term "hypervariable region" as used herein refers to the amino acid residues in the variable domain of an antibody, which are responsible for antigen binding. The hypervariable region comprises amino acid residues from a "complementarity determining region" or "CDR". The CDRs are primarily responsible for binding to an epitope of an antigen. The extent of FRs and CDRs has been precisely defined (see, Kabat et al.). In some embodiments, CDRs are determined using the KABAT system. In some embodiments, CDRs are determined using the Chothia system. In some embodiments, the Chothia system is the enhanced Chothia system (Martin system).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 57:6851-6855 (1984)). In addition, complementarity determining region (CDR) grafting may be performed to alter certain properties of the antibody molecule including affinity or specificity. A non-limiting example of CDR grafting is disclosed in U.S. Pat. No. 5,225,539.

Chimeric antibodies are molecules, the different portions of which are derived from different animal species, such as those having a variable region derived from a murine mAb and a human immunoglobulin constant region. Antibodies which have variable region framework residues substantially from human antibody (termed an acceptor antibody) and complementarity determining regions substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (for example PCT patent applications WO 86/01533, WO 97/02671, WO 90/07861, WO 92/22653 and U.S. Pat. Nos. 5,693,762, 5,693,761, 5,585,089, 5,530,101 and 5,225,539). As used herein, the term "humanized antibody" refers to an antibody comprising a framework region from a human antibody and one or more CDRs from a non-human (usually a mouse or rat) immunoglobulin. Parts of a humanized immunoglobulin, except possibly the CDRs, are substantially identical to corresponding parts of natural human immunoglobulin sequences. In some cases, however, specific amino acid residues, for example in the framework regions, may be modified, so as to optimize performance of the humanized antibody. Importantly, the humanized antibody is expected to bind to the same antigen as the donor antibody that provides the CDRs. For further details, see e.g. U.S. Pat. No. 5,225,539 assigned to Medical Research Council, UK. The terms "a framework region from an acceptor human immunoglobulin" and "a framework region derived from an acceptor human immunoglobulin", and similar grammatical expressions are used interchangeably herein to refer to a framework region or portion thereof that has the same amino acid sequence of the acceptor human immunoglobulin.

The term "monoclonal antibody" or "mAb" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed antibodies to be used in accordance with the methods provided herein may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al, J. Mol. Biol. 222:581-597 (1991), for example.

The mAb of the present invention may be of any immunoglobulin class including IgG, IgM, IgE or IgA. A hybridoma producing a mAb may be cultivated in vitro or in vivo. High titers of mAbs can be obtained in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

"Antibody fragments" or "antigen-binding fragment" are used synonymously and comprise a portion of an intact antibody, preferably comprising the antigen binding region thereof. Examples of antibody fragments include Fab, Fab', $F(ab')_2$, and Fv fragments; diabodies: tandem diabodies (taDb), linear antibodies (e.g., U.S. Pat. No. 5,641,870, Example 2; Zapata et al., Protein Eng. 8(10): 1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. $F(ab')_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called a, delta, e, gamma, and micro, respectively. The subunit structures and three-dimensional configurations of different classes of immunoglobulins are well known.

"Single-chain Fv" or "scFv" antibody fragments comprise the VH and VL domains of antibody, wherein these domains are present in a single polypeptide chain. In some embodiments, the Fv polypeptide further comprises a polypeptide linker between the VH and VL domains that enables the scFv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are Natl. Acad. Sci. USA, 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain (VH) and a light chain variable domain (VL), where the VHVL unit has polyepitopic specificity, antibodies having two or more VL and VH domains with each VHVL unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s).

The monoclonal antibodies of the invention may be prepared using methods well known in the art. Examples include various techniques, such as those in Kohler, G. and Milstein, C, Nature 256: 495-497 (1975); Kozbor et al., Immunology Today 4: 72 (1983); Cole et al., pg. 77-96 in MONOCLONAL ANTIBODIES AND CANCER THERAPY, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

In some embodiments, antibodies as described herein are neutralizing antibodies. "Neutralization", as discussed here, is defined as the reduction in protein function by antibodies of the invention. In one embodiment, "neutralization", as discussed here, is binding of antibodies to the surface of immune cells, preferably to immature and mature myeloid linage derived cells, T cells and NK cells, thereby blocking the propagation of inhibitory signals inside these cells and conferring a less suppressive phenotype and function.

In some embodiments, the present invention provides nucleic acid sequences encoding the antibody of the present invention. In one embodiment, an antibody as described herein is encoded by a DNA molecule comprising a DNA sequence having at least 75% identity to a DNA sequence as described herein. In one embodiment, an antibody as described herein is encoded by a DNA molecule comprising a DNA sequence having at least 80% identity to a DNA sequence as described herein. In one embodiment, an antibody as described herein is encoded by a DNA molecule comprising a DNA sequence having at least 85% identity to a DNA sequence as described herein. In one embodiment, an antibody as described herein is encoded by a DNA molecule comprising a DNA sequence having at least 90% identity to a DNA sequence as described herein. In one embodiment, an antibody as described herein is encoded by a DNA molecule comprising a DNA sequence having at least 95% identity to a DNA sequence as described herein.

By another aspect, there is provided a nucleic acid sequence encoding an antibody or antigen-binding fragment of the invention.

By another aspect, there is provided a nucleic acid molecule encoding an antibody or antigen-binding fragment of the invention.

In some embodiments, a nucleic acid sequence encoding a heavy chain of an antibody or antigen-binding fragment of the invention is selected form (SEQ ID NO: 32)

CAGGTTCAGCTGCAGCAGTCTGGAGCTGAGCTGGCGAGGCCTGGGGCTT

CAGTGAAGCTGTCCTGCAAGGCTTCTGGCTACACCTTCACAAGCTATGG

TATAAGCTGGGTGAAGCAGAGAACTGGACAGGGCCTTGAGTGGGTTGGA

-continued

GAGATTTATCCTGGAAGTGGTAATTCTTACTACAATGAGAAGTTCAAGG

GCAAGGCCACACTGACTGCAGACAAATCCTCCAGCACAGCGTACATGGA

GCTCCGCAGCCTGACATCTGAGGACTCTGCGGTCTATTTCTGTGCAAGA

TCGAATGATGGTTACCCTGACTACTGGGGCCAAGGCACCACTCTCACAG

TCTCCTCA, (SEQ ID NO: 33)
GATGTACAGCTTCAGGGGTCAGGACCTGGCCTCGTGAAACCTTCTCAGT

CTCTGTCTCTCACCTGCTCTGTCACTGGCTACTCCATCACCAGTGGTTA

TTACTGGAACTGGATCCGGCAGTTTCCAGGAAACAAACTGGAATGGATG

GGCTACATAAGCTACGATGGTAGCAATAACTACAACCCATCTCTCAAAA

ATCGAATCTCCATCACTCGTGACACATCTAAGAACCAGTTTTTCCTGAA

GTTGAATTCTGTGACTTTTGAGGACACAGCCACATATTACTGTGCCCAT

GGTTACTCATATTACTATGCTATGGACTGCTGGGGTCAAGGAACCTCAG

TCACCGTCTCCTCA, (SEQ ID NO: 34)
GATGTCCAGCTGCAAGGCTCTGGCCCTGGACTGGTTAAGCCTTCCGAGA

CACTGTCCCTGACCTGCTCTGTGACCGGCTACTCTATCACCTCCGGCTA

CTACTGGAACTGGATCAGACAGTTCCCCGGCAAGAAACTGGAATGGATG

GGCTACATCTCCTACGACGGCTCCAACAACTACAACCCCAGCCTGAAGA

ACCGGATCACCATCTCTCGGGACACCTCCAAGAACCAGTTCTCCCTGAA

GCTGAACTCCGTGACCGCTGCCGATACCGCTACCTACTACTGTGCTCAC

GGCTACTCCTACTACTACGCCATGGATGCTTGGGGCCAGGGCACATCTG

TGACAGTGTCCTCT
and (SEQ ID NO: 35)
CAGGTTCAGCTGCAACAGTCTGACGCTGAGTTGGTGAAACCTGGAGCTT

CAGTGAAGATATCCTGCAAGGTTTCTGGCTACACCTTCACTGACCATAC

TATTCACTGGATGAAGCAGAGGCCTGAACAGGGCCTGGAATGGATTGGA

TATATTTATCCTAGAGATGGTAGTACTAAGTACAATGAGAAGTTCAAGG

GCAAGGCCACATTGACTGCAGACAAATCCTCCAGCACAGCCTACATGCA

GCTCAACAGCCTGACATCTGAGGACTCTGCAGTCTATTTCTGTGCAAGA

ACCTGGGACTACTTTGACTACTGGGGCCAAGGCACCACTCTCACAGTCT

CCTCA.

In some embodiments, a nucleic acid sequence encoding a light chain of an antibody or antigen-binding fragment of the invention is selected from (SEQ ID NO: 36)
GACATTGTGCTGACCCAATCTCCAGCTTCTTTGGCTGTGTCTCTAGGGC

AGAGGGCCACCATATCCTGCAGAGCCAGTGAAAGTGTTGATAGTTATGG

CAATAGTTTTATGCACTGGTACCAGCAGAAACCAGGACAGCCACCCAAA

CTCCTCATCTATCGTGCATCCAACCTAGAATCTGGGATCCCTGCCAGGT

TCAGTGGCAGTGGGTCTAGGACAGACTTCACCCTCACCATTAATCCTGT

-continued

GGAGGCTGATGATGTTGCAACCTATTACTGTCAGCAAAGTAATGAGGAT

CCGTACACGTTCGGAGGGGGGACCAAGCTGGAAATAAAA, (SEQ ID NO: 37)
GATATCCAGATGACACAGACTACATCCTCCCTGTCTGCCTCTCTGGGAG

ACAGTCACCATCAGTTGCAGGACAAGTCAGGACATTAGCAATTATTTAA

ACTGGTCAGCAGAAACCAGATGGAACTGTTAAACTCCTGATCTCCTACA

CATCAAGATCACTCAGGAGTCCCATCAAGGTTCAGTGGCAGTGGGTCTG

GAACAGATTATTCTCACCATTAGCAACCTGGAGCAAGAAGATATTGCCA

CTTACTTTTGCCAACGGTAATACGCTTCCCACGTTCGGCTCGGGGACAA

AGTTGGAAATAAAA, (SEQ ID NO: 38)
GACATCCAGATGACCCAGTCTCCATCCTCTCTGTCTGCCTCTGTGGGCG

ACAGAGTGACCATCACCTGTCGGACCTCTCAGGACATCTCCAACTACCT

GAACTGGTATCAGCAGAAACCCGGCAAGGCCGTGAAGCTGCTGATCTCC

TACACCTCCAGACTGCACTCTGGCGTGCCCTCCAGATTTTCTGGCTCTG

GATCTGGCACCGACTACACCCTGACCATCAGTTCTCTGCAGCCTGAGGA

CTTCGCCACCTACTACTGTCAGCAGGGCAACACCCTGCCTACCTTTGGC

CAGGGCACCAAGCTGGAAATCAAG
and (SEQ ID NO: 39)
GACATCCAGATGACACAATCTTCATCCTACTTGTCTGTATCTCTAGGAG

GCAGAGTCACCATTACTTGCAAGGCAAGTGACCACATTAATAATTGGTT

AGCCTGGTATCAGCAGAAACCAGGAAATGCTCCTAGGCTCTTAATATCT

GGTGCAACCAGTTTGGAAACTGGGGTTCCTTCAAGATTCAGTGGCAGTG

GATCTGGAAAGGATTACACTCTCAGCATTACCAGTCTTCAGACTGAAGA

TGTTGCTACTTATTACTGTCAACAGTATTGGAGTACTCCGTGGACGTTC

GGTGGAGGCACCAAGCTGGAAATCAAA.

In some embodiments, the antibody or antigen-binding fragment is murine and the sequence encoding a heavy chain is selected from SEQ ID NO: 32, 33, and 35. In some embodiments, the antibody or antigen-binding fragment is murine and the sequence encoding a light chain is selected from SEQ ID NO: 36, 37, and 39. In some embodiments, the antibody or antigen-binding fragment is humanized and the sequence encoding a heavy chain is SEQ ID NO: 34. In some embodiments, the antibody or antigen-binding fragment is humanized and the sequence encoding a light chain is SEQ ID NO: 38.

"Polynucleotide," or "nucleic acid." as used interchangeably herein, refer to polymers of nucleotides of any length, and include DNA and RNA.

Polynucleotides encoding polypeptides may be obtained from any source including, but not limited to, a cDNA library prepared from tissue believed to possess the polypeptide mRNA and to express it at a detectable level. Accordingly, polynucleotides encoding a polypeptide can be conveniently obtained from a cDNA library prepared from human tissue. The polypeptide-encoding gene may also be obtained from a genomic library or by known synthetic procedures (e.g., automated nucleic acid synthesis).

For example, the polynucleotide may encode an entire immunoglobulin molecule chain, such as a light chain or a heavy chain. A complete heavy chain includes not only a heavy chain variable region (VH) but also a heavy chain constant region (CH), which typically will comprise three constant domains: CH1, CH2 and CH3: and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and CH1 and CK or CL domain has been excised. As minibodies are smaller than conventional antibodies they should achieve better tissue penetration in clinical/diagnostic use, but being bivalent they should retain higher binding affinity than monovalent antibody fragments, such as dAbs. Accordingly, unless the context dictates otherwise, the term "antibody" as used herein encompasses not only whole antibody molecules, but also antigen-binding antibody fragments of the type discussed above. Each framework region present in the encoded polypeptide may comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions. Given the properties of the individual amino acids comprising the disclosed protein products, some rational substitutions will be recognized by the skilled worker. Amino acid substitutions. i.e., "conservative substitutions," may be made, for instance, on the basis of similarity in polarity, charge, solubility, hydrophobicity, hydrophilicity, and/or the amphipathic nature of the residues involved.

Suitably, the polynucleotides described herein may be isolated and/or purified. In some embodiments, the polynucleotides are isolated polynucleotides.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

Methods for Treatment and Diagnosis

By another aspect, there is provided a method of treating an HLA, MHC-1 or both expressing cancer in a subject in need thereof, the method comprising administering to the subject an antibody or antigen-binding fragment of the invention.

By another aspect, there is provided a method of treating a cancer in a subject in need thereof, the method comprising confirming expression of ILT2 in the subject is above a predetermined threshold and administering to the subject an agent that inhibits ILT2 based immune suppression, thereby treating a cancer in a subject.

By another aspect, there is provided a method of treating a cancer in a subject in need thereof, the method comprising: administering to the subject an agent that inhibits ILT2-mediated immune suppression; and administering to the subject an a PD-1/PD-L1 based therapy: thereby treating a cancer in a subject.

By another aspect, there is provided a method of increasing efficacy of a PD-1/PD-L1 based therapy against a cancer cell, the method comprising contacting the cancer cell with an agent that inhibits ILT2-mediated immune suppression.

By another aspect, there is provided an agent that binds and inhibits ILT2 mediated immune cell suppression for use in combination with an anti-PD-L1/PD-1 based therapy to treat a subject suffering from cancer.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

As used herein the term "treatment" refers to clinical intervention in an attempt to alter the course of disease in the individual being treated and can be performed either for prophylaxis or during the course of clinical pathology. Desirable effects of treatment include preventing occurrence or recurrence of the disease, alleviation of symptoms, reducing a pathological consequence of the disease, reducing the rate of disease progression, amelioration of the disease state, remission or improved prognosis. The term "treatment" may also encompass ex vivo procedures affecting cells or tissues in culture.

In some embodiments, the antibody or antigen-binding fragment is administered as a monotherapy. In some embodiments, the antibody or antigen-binding fragment is administered with PD-1/PD-L1 therapy. In some embodiments, the antibody or antigen-binding fragment is administered with an opsonizing agent. In some embodiments, the opsonizing agent is not an anti-CD47 agent. In some embodiments, an anti-CD47 agent is an anti-CD47 antibody. In some embodiments, the antibody or antigen-binding fragment is not administered with anti-CD47 agent or therapy. In some embodiments, the antibody or antigen-binding fragment is not combined with an anti-CD47 agent or therapy.

In some embodiments, treating comprises increasing immune surveillance. In some embodiments, treating comprises increasing an immune response. In some embodiments, treating comprises decreasing tumor burden. In some embodiments, treating comprises reducing cancer metastasis. In some embodiments, treating comprises increasing cytotoxicity against the cancer. In some embodiments, treating comprises increasing inflammatory response against the cancer. In some embodiments, treating comprises increased phagocytosis of the cancer.

As used herein the term "subject" refers to an individual, or a patient, which is a vertebrate, e.g. a mammal, including especially a human. In some embodiments, the subject is a human. In some embodiments, the subject is a mammal. In some embodiments, the subject suffers from cancer.

In some embodiments, the cancer is an HLA expressing cancer. In some embodiments, HLA is HLA-G. In some embodiments, the cancer is an MHC-I expressing cancer. In some embodiments, the cancer is a PD-1 expressing cancer. In some embodiments, the cancer is a solid cancer. In some embodiments, the cancer is a blood cancer. In some embodiments, the cancer is refractory to PD-1 and/or PD-L1 based therapy. In some embodiments, the cancer never responded to PD-1 and/or PD-L1 based therapy. In some embodiments, the cancer was responsive to a PD-1 and/or PD-L1 based therapy but became refractory. In some embodiments, the method of the invention converts a refractory cancer to a responsive cancer.

In some embodiments, the method comprises confirming the cancer expresses HLA, MHC-I or both. In some embodiments, the method comprises confirming the cancer expresses HLA. In some embodiments, the method comprises confirming the cancer expresses MHC-I. In some embodiments, the method comprises confirming the cancer expresses HLA and MHC-I. In some embodiments, the confirming comprises measuring expression in the cancer. In some embodiments, the confirming comprises measuring expression on the surface of the cancer. In some embodiments, in and/or on the cancer is in and/or on a cancer cell. In some embodiments, the confirming comprises measuring HLA-G secreted by the cancer. In some embodiments, the confirming comprises measuring soluble HLA-G. In some embodiments, the soluble HLA-G is in a bodily fluid. In some embodiments, the bodily fluid is blood.

In some embodiments, the method comprises confirming expression of ILT2 in the subject. In some embodiments, the method comprises confirming expression of ILT2 in the subject is above a predetermined threshold. In some embodiments, confirming comprises measuring expression of ILT2 in the subject. In some embodiments, the confirming is before the administering. In some embodiments, the measuring is before the administering. In some embodiments, expression of ILT2 is expression in an immune cell. In some embodiments, expression of ILT2 is expression in an immune cell of the subject. In some embodiments, the immune cell is a peripheral blood immune cell. In some embodiments, the immune cell is a peripheral blood mononuclear cell (PBMC). In some embodiments, the immune cell is an intratumor immune cell. In some embodiments, the immune cell is an immune cell in the tumor microenvironment (TME). In some embodiments, the immune cell is selected from a CD8 positive T cell, a macrophage, an NK cell and a $T_{EMRA}$ cell. In some embodiments, the immune cell is CD8 positive T cell. In some embodiments, the immune cell is a peripheral blood CD8 positive T cell.

In some embodiments, administering an antibody or antigen-binding fragment of the invention comprises administering a pharmaceutical composition comprising an antibody or antigen-binding fragment of the invention. In some embodiments, a therapeutically effective amount of antibody or antigen-binding fragment is administered. In some embodiments, the pharmaceutical composition further comprises a carrier, excipient or adjuvant. In some embodiments, the carrier is a pharmaceutically acceptable carrier.

As used herein, the term "carrier," "excipient." or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate: powdered tragacanth: malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution: ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic. Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelies, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al., Current Protocols in Protein Science, 1999, John Wiley & Sons, Inc., New York. and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

The term "therapeutically effective amount" refers to an amount of a drug effective to treat a disease or disorder in a mammal. The term "a therapeutically effective amount" refers to an amount effective, at dosages and for periods of time necessary, to achieve the desired therapeutic or prophylactic result. The exact dosage form and regimen would be determined by the physician according to the patient's condition.

In some embodiments, the method further comprises administering to the subject an opsonizing agent. In some embodiments, the method further comprises contacting the cell with an opsonizing agent. In some embodiments, the opsonizing agent is an epidermal growth factor receptor (EGFR) inhibitor. In some embodiments, the EGFR inhibitor is cetuximab. In some embodiments, the opsonizing agent is not an anti-CD47 agent. In some embodiments, the method further comprises administering to the subject a PD-1/PD-L1 based therapy. In some embodiments, the method further comprises contacting the cell with a PD-1/PD-L1 based therapy. In some embodiments, the method further comprises growing the cell in the presence of a PD-1/PD-L1 based therapy. In some embodiments, the PD-1/PD-L1 based therapy is a PD-1 or PD-L1 blocking antibody. In some embodiments, the method does not comprise administering an anti-CD47 agent or therapy. In some embodiments, the method is devoid of administration of an anti-CD47 agent or therapy. In some embodiments, the method further comprises administering an anti-CD47 agent or therapy.

In some embodiments, the agent that inhibits ILT2 based immune suppression binds to ILT2. In some embodiments, the agent binds the ILT2 extracellular domain. In some embodiments, the agent is an ILT2 antagonist. In some embodiments, the agent is an ILT2 blocking antibody. In some embodiments, the agent inhibits ILT2 interaction with B2M. In some embodiments, the agent is an antibody of the invention.

In some embodiments, the agent that inhibits ILT2 based immune suppression is administered before, after or concomitantly with the opsonizing agent. In some embodiments, the agent that inhibits ILT2 based immune suppression and the opsonizing agent are administered in a single composition. In some embodiments, the agent that inhibits ILT2 based immune suppression and the opsonizing agent are administered in separate compositions.

In some embodiments, the agent that inhibits ILT2 based immune suppression is administered before, after or concomitantly with the PD-1/PD-L1 therapy. In some embodiments, the agent that inhibits ILT2 based immune suppression and the PD-1/PD-L1 therapy are administered in a single composition. In some embodiments, the agent that inhibits ILT2 based immune suppression and the PD-1/PD-L1 therapy are administered in separate compositions. In some embodiments, at least one of the agents or therapies is adapted for co-administration.

The term "adapted for co-administration" as used herein, refers to the antibodies being present in a form such they can be safely and easily administered to a subject. Co-administration, in some non-limiting embodiments, can be done orally, by injection, or by inhalation. In some embodiments, the antibodies will be comprised within a pharmaceutical composition such as can be safely and easily administered to a subject. In some embodiments, the pharmaceutical composition comprises the antibodies and a pharmaceutically acceptable carrier or excipient.

In some embodiments, HLA is HLA-G. In some embodiments, HLA is a non-canonical HLA. In some embodiments, the HLA is a canonical HLA. In some embodiments, mRNA expression is confirmed. In some embodiments, protein expression is confirmed. In some embodiments, surface expression of the protein is confirmed. Methods of measuring expression are well known in the art and include, PCR, Q-PCR, northern blot, immunoblot, in situ hybridization, immunostaining, and FACS. In some embodiments, the method comprises FACS analysis of the cancer to confirm surface expression.

Formulations

The present invention also contemplates pharmaceutical formulations for human medical use, which comprise as the active agent at least one antibody which recognizes ILT2, for the manufacture of a therapeutic composition for the treatment, diagnosis or prophylaxis of the conditions variously described herein.

In such pharmaceutical and medicament formulations, the active agent is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

Typically, the molecules of the present invention comprising the antigen binding portion of an antibody will be suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly (ethylene-co-vinyl acetate) and matrices of a polyanhydride copolymer of a stearic acid dimer and sebaric acid. The rate of release of the molecule according to the present invention, i.e., of an antibody or antibody fragment, from such a matrix depends upon the molecular weight of the molecule, the amount of the molecule within the matrix, and the size of dispersed particles.

The pharmaceutical composition of this invention may be administered by any suitable means, such as orally, topically, intranasally, subcutaneously, intramuscularly, intravenously, intra-arterially, intraarticulary, intralesionally or parenterally. Ordinarily, intravenous (i.v.), intraarticular, topical or parenteral administration will be preferred.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician.

Although an appropriate dosage of a molecule (an antibody or a fragment thereof) of the invention varies depending on the administration route, type of molecule (polypeptide, polynucleotide, organic molecule etc.) age, body weight, sex, or conditions of the patient, and should be determined by the physician in the end, in the case of oral administration, the daily dosage can generally be between about 0.01 mg to about 500 mg, preferably about 0.01 mg to about 50 mg, more preferably about 0.1 mg to about 10 mg, per kg body weight. In the case of parenteral administration, the daily dosage can generally be between about 0.001 mg to about 100 mg, preferably about 0.001 mg to about 10 mg, more preferably about 0.01 mg to about 1 mg, per kg body weight. The daily dosage can be administered, for example in regimens typical of 1-4 individual administration daily. Other preferred methods of administration include intraarticular administration of about 0.01 mg to about 100 mg per kg body weight. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

Suitable dosing regimens of combination chemotherapies are known in the art and described in, for example, Saltz et al. Proc ASCO 1999, 18, 233a and Douillard et al., Lancet 2000, 355, 1041-7.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

Methods of Production

By another aspect, there is provided a method of producing an agent, the method comprising: obtaining an agent that binds to an ILT2 extracellular domain or fragment thereof, testing an ability of the agent to increase at least one of macrophage inflammatory activity, T cell activity against a cancer cell, dendritic cell activity, and natural killer (NK) cell cytotoxicity against a cancer cell and selecting at least one agent that increases at least one of the macrophage activity, T cell activity, the dendritic cell activity and the cytotoxicity; thereby producing an agent.

By another aspect, there is provided a method of producing an agent, the method comprising: culturing a host cell comprising one or more vectors comprising a nucleic acid sequence encoding an agent, wherein the nucleic acid sequence is that of an agent that was selected by:

i. obtaining an agent that binds to an ILT2 extracellular domain or fragment thereof;
ii. testing an ability of said agent to increase at least one of macrophage inflammatory activity. T cell activity against a cancer cell, dendritic cell activity, and NK cell cytotoxicity against a cancer cell: and
iii. selecting at least one agent that increases at least one of the phagocytosis, the activity and the cytotoxicity:

thereby producing an agent.

By another aspect, there is provided a method of producing an agent, the method comprising: obtaining an agent that binds to an ILT2 extracellular domain or fragment thereof, testing an ability of the agent to increase efficacy of an anti-PD-L1/PD-1 based therapy against a cancer cell and selecting at least one agent that increases the efficacy of an anti-PD-L1/PD-1 based therapy; thereby producing an agent.

By another aspect, there is provided a method of producing an agent, the method comprising: culturing a host cell comprising one or more vectors comprising a nucleic acid sequence encoding an agent, wherein the nucleic acid sequence is that of an agent that was selected by:

i. obtaining an agent that binds to an ILT2 extracellular domain or fragment thereof;
ii. testing an ability of the agent to increase efficacy of an anti-PD-L1/PD-1 based therapy against a cancer cell; and
iii. selecting at least one agent that increases efficacy of an anti-PD-L1/PD-1 based therapy against a cancer cell;

thereby producing an agent.

By another aspect, there is provided a method for producing an agent, the method comprising:

obtaining an agent that binds to an ILT2 extracellular domain or fragment thereof, testing an ability of said agent to induce at least two of: increased phagocytosis of a cancer cell by macrophages, increased T cell activity against a cancer cell, increased generation of M1 macrophages, reduced generation of M2 macrophages, increased recruitment of dendritic cells to a tumor microenvironment, increased dendritic cell activation, and increased natural killer (NK) cell cytotoxicity against a cancer cell and selecting at least one agent that induces at least two of said increased phagocytosis, said increased activity, said increased generation, said reduced generation, said recruitment, said increased activation, said decreased activity and said increased cytotoxicity: thereby producing an agent.

By another aspect, there is provided a method for producing an agent, the method comprising:

culturing a host cell comprising one or more vectors comprising a nucleic acid sequence encoding an agent, wherein the nucleic acid sequence is that of an agent that was selected by:

i. obtaining an agent that binds to an ILT2 extracellular domain or fragment thereof;
ii. testing an ability of said agent to induce at least two of: increased phagocytosis of a cancer cell by macrophages, increased T cell activity against a cancer cell, increased generation of M1 macrophages, reduced generation of M2 macrophages, increased recruitment of dendritic cells to a tumor microenvironment, increased dendritic cell activation, and increased natural killer (NK) cell cytotoxicity against a cancer cell; and
iii. selecting at least one agent that increases at least two of said increased phagocytosis, said increased activity, said increased generation, said reduced generation, said recruitment, said increased activation, said decreased activity and said increased cytotoxicity:

thereby producing an agent.

By another aspect, there is provided a method for producing an agent, the method comprising:

obtaining an agent that binds to an ILT2 extracellular domain or fragment thereof, testing an ability of said agent to inhibit interaction between ILT2 and B2M and selecting at least one agent that inhibits interaction between ILT2 and B2M: thereby producing an agent.

By another aspect, there is provided a method for producing an agent, the method comprising:

culturing a host cell comprising one or more vectors comprising a nucleic acid sequence encoding an agent, wherein the nucleic acid sequence is that of an agent that was selected by:

i. obtaining an agent that binds to an ILT2 extracellular domain or fragment thereof;
ii. testing an ability of said agent to inhibit interaction between ILT2 and B2M; and
iii. selecting at least one agent that inhibits interaction between ILT2 and B2M;

thereby producing an agent.

By another aspect, there is provided a method for producing an agent, the method comprising: obtaining an agent that binds to an ILT2 epitope within a sequence of human ILT2 selected from SEQ ID NO: 41, 42, 43 and 44; thereby producing an agent.

By another aspect, there is provided a method for producing an agent, the method comprising: culturing a host cell comprising one or more vectors comprising a nucleic acid sequence encoding an agent, wherein the nucleic acid sequence is that of an agent that was selected by obtaining an agent that binds to an 1LT2 epitope within a sequence of human ILT2 selected from SEQ ID NO: 41, 42, 43 and 44; thereby producing an agent.

In some embodiments, the method further comprises testing an ability of the agent to inhibit ILT2 mediated immune suppression and selecting at least one agent that inhibits ILT2 mediated immune suppression. In some embodiments, the nucleic acid sequence is of an agent selected by testing an ability of the agent to inhibit ILT2 mediated immune suppression and selecting an agent that inhibits ILT2 mediated immune suppression. In some embodiments, the method comprises testing an ability of said agent to induce at least three of: increased phagocytosis of a cancer cell by macrophages, increased T cell activity against a cancer cell, increased generation of M1 macrophages, reduced generation of M2 macrophages, increased recruitment of dendritic cells to a tumor microenvironment, increased dendritic cell activation, and increased natural killer (NK) cell cytotoxicity against and selecting at least one agent that induces at least three. In some embodiments, the method comprises testing the ability of the agent to induce an effect in at least three of T cells, NK cells, dendritic cells and macrophages. In some embodiments, the method comprises testing the ability of the agent to induce an effect in T cells, NK cells, dendritic cells and macrophages.

In some embodiments, increasing efficacy comprises a synergistic increase in an anti-cancer effect. In some embodiments, the anti-cancer effect is pro-inflammatory cytokine secretion. In some embodiments, the pro-inflammatory cytokine is selected from GM-CSF, IL-6 and IFNγ. In some embodiments, the pro inflammatory cytokine is GM-CSF, IL-6 or IFNγ. Each possibility represents a separate embodiment of the invention. In some embodiments, the pro inflammatory cytokine is GM-CSF. In some embodiments, the increased efficacy comprises a synergistic increase in T cell activation. In some embodiments, the increased efficacy comprises a synergistic increase in T cell cytotoxicity. In some embodiments, the increased efficacy comprises a synergistic increase in both T cell activation and cytotoxicity. In some embodiments, the increase comprises increased membranal CD107a expression. In some embodiments, the increase is characterized by increased membranal CD107a expression. In some embodiments, the increase is as compared to efficacy when the agent is not administered or contacted. In some embodiments, increasing efficacy comprises converting a cancer refractory to the PD-1/PD-L1 based therapy to a cancer that responds to the therapy. In some embodiments, the cancer expresses HLA. In some embodiments, the cancer expresses MHC-I.

In some embodiments, increased macrophage inflammatory activity comprises increased phagocytosis of a cancer cell by a macrophage. In some embodiments, increased macrophage inflammatory activity comprises increasing generation of M1 macrophages. In some embodiments, increased macrophage inflammatory activity comprises decreasing generation of M2 macrophages. In some embodiments, increased macrophage inflammatory activity comprises increasing M1 phenotype on macrophages. In some embodiments, increased macrophage inflammatory activity comprises decreasing M2 phenotype on macrophages.

In some embodiments, dendritic cell activity comprises dendritic cell activation. In some embodiments, dendritic cell activity comprises dendritic cell recruitment to a tumor. In some embodiments, dendritic cell activity is activity against a cancer cell. In some embodiments, activity against a cancer cell is activity in the TME. In some embodiments, a tumor is the TME. In some embodiments, dendritic cell activity comprises antigen presentation.

In some embodiments, testing an ability of the agent comprises the ability of the agent to increase at least 1, 2, 3, 4, 5 or all of T cell activity against a cancer cell, macrophage inflammatory activity, dendritic cell activity, and natural killer (NK) cell cytotoxicity against a cancer cell. Each possibility represents a separate embodiment of the invention. In some embodiments, selecting at least one agent comprises selecting an agent that increases at least 1, 2, 3, 4, 5 or all of T cell activity against a cancer cell, macrophage inflammatory activity, dendritic cell activity, and natural killer (NK) cell cytotoxicity against a cancer cell. In some embodiments, increasing macrophage inflammatory activity is increasing generation of M1 macrophages and/or increasing phagocytosis of a cancer cell by macrophages. In some embodiments, increasing macrophage inflammatory activity is decreasing generation of M2 macrophages. In some embodiments, testing an ability of an agent comprises the ability of the agent to increase macrophage inflammatory activity. In some embodiments, testing an ability of an agent comprises the ability of the agent to increase dendritic cell activity. In some embodiments, to a tumor is to a TME. In some embodiments, testing an ability of an agent comprises the ability of the agent to increase NK cell cytotoxicity against a cancer cell.

In some embodiments, the method further comprises testing an ability of the agent to inhibit interaction of ILT2 and B2M. In some embodiments, the interaction is direct interaction. In some embodiments, the method further comprises testing an ability of the agent to inhibit contact of ILT2 and B2M. In some embodiments, interaction is binding. In some embodiments, contact is binding. In some embodiments, the method further comprises testing an ability of the agent to bind the epitope.

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the appended claims.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning; A laboratory Manual" Sambrook et al., (1989); "Current Protocols in Molecular Biology" Volumes I-III Ausubel, R. M., ed. (1994): Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998): methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition: "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996), "Monoclonal Antibodies: Methods and Protocols". Vincent Ossipow, Nicolas Fischer. Humana Press (2014): "Monoclonal Antibodies: Methods and Protocols". Maher Albitar. Springer Science & Business Media (2007), all of which are incorporated by reference. Other general references are provided throughout this document.

Materials and Methods

Antibodies—

Commercial anti-ILT2 mAbs are: Clone #1—GHI/75 (BioLegend, Cat. No. 333704). Clone #2—HP-F1 (eBioscience, Cat. No. 16-5129). Additional mAbs used: HLA-G (MEM-G/9; Abcam, Cat. No. ab7758: G-0031.), ILT4 (42D1, Biolegend, Cat. No. 338704), ILT6 (Sino Biological, Cat No. 13549-MM06), LILRA1 (R&D systems, Cat. No. MAB30851). pan-HLA (W6/22: eBioscience, Cat. No. 16-9983-85) and His (Proteintech, Cat. No. 10001-0-AP).

Flow Cytometry—

In general, cells were kept on ice or at 4° C. during all steps. Prior to staining, $5\times10^5$ cells were blocked with 50 µg/mL human IgG (Sigma, cat #I4506) in FACS buffer (PBS with 0.1% BSA) for 15 min. Antibodies were used at concentrations recommended by the manufacturer and incubated for 30 min. in the dark. Incubation was done in 100 µL in 96-well U bottom plates, cells were washed twice with 200 µL FACS buffer and transferred to FACS tubes in 150 µL FACS buffer for analysis. Cells were analyzed on Gallios Flow Cytometer (Beckman coulter) using the Kaluza for Gallios Flow Cytometry Acquisition Software.

Myeloid Cell Differentiation—

Monocytes were isolated from fresh blood samples from healthy donors using EasySep™ Human Monocyte Enrichment Kit (STEMCELL, cat #19059) by negative selection method. The different cell populations were tested for the indicated phenotypes by FACS analysis of relevant markers and by analysis of secretion of characteristic cytokines. For maturation, monocytes were cultured at a density of $0.8\times10^6$/mL in RPMI media with growth factors that was refreshed at day 3 and at day 6. Inflammatory M1 macrophages were matured in the presence of 50 ng/mL GM-CSF (M1 phenotype) for 6 days and then 20 ng/mL IFN-gamma and 50 ng/mL LPS for 48 hr. Suppressive M2 macrophages were differentiated using 50 ng/mL of M-CSF for 6 days and then 10 ng/mL M-CSF and 20 ng/mL IL-4 and IL-10 for 48 hr. Dendritic cells were induced by 50 ng/mL GM-CSF and 20 ng/mL IL-4 for 6 days and further differentiated into mature (100 ng/mL LPS) ortolerogenic (IL-10 100 U/mL and IFN-α2b (1000 U/mL) dendritic cells.

Transfection—

HLA-G1 (encoding the full-length HLA-G transcript) plasmids were generated by cloning HLA-G1 cDNA into a PCDNA3.1 vector. Transfection was done using jetPEI® Transfection reagent (PolyPlus Transfections). ILT2/CD3z plasmid was generated by combining in frame the extracellular portion of human ILT2 protein with the transmembrane and cytoplasmic residues of the mouse CD3 gene. The plasmid was nucleofected into mouse BW5417.3 T cell line using Nucleofector II (Lonza) as described by the manufacturer. Stable transfectants were selected in G418-containing medium.

NK and Cancer Cell Line Co-Culture Assay—

NK cells were incubated with the indicated cell lines in the presence of anti-ILT2 antibodies and matching isotype controls for 5 hours at 37° C. Cytotoxicity levels were measured using a fluorometric LDH detection kit (Promega).

Flow Cytometry Blocking Assay—

Recombinant human ILT2 protein fused with the Fc portion of human IgG1 at the N terminal was conjugated with biotin (Innova bioscience). A total of $5\times10^5$ A375/HLA-G1 cells were incubated in a volume of 100 µL in the presence of anti-ILT2 clone #1 or isotype matched control mAb and ILT2-Fc conjugated with biotin (10 µg/mL) for 30 minutes at room temperature. After several washing steps, streptavidin-PE was added at a final concentration of 0.2 µg/mL and incubated for 30 min on ice followed by FACS analysis.

BW ILT2/CD3z-Chain Chimera Assay—

$3\times10^4$ BW/ILT2z were mixed with equivalent number of A375/WT or A375/HLA-G1 cells for 24 hr. Functional mAbs were used at indicated concentrations and the matching isotype controls. The amount of secreted mouse IL2 was evaluated by commercial ELISA kit (BioLegend).

Example 1

ILT2 and HLA-G are Found on Cancer Cells and Cancer Relevant Immune Cells

ILT2, is a known immunosuppressive molecule found on the surface of healthy immune cells as well as many tumor cells. ILT2 has been shown to bind MHC-1 as well as HLA class molecules (HLA-G, as well as HLA-F and HLA-B27), and competes with CD8 and thereby inhibits T cell activation. In order to further understand the breadth of cells that express ILT2, flow cytometric analysis was performed using a commercial antibody (antibody #1) on a variety of immune cells. As reported in the literature, cytotoxic T cells (CTLs) derived from a melanoma patient, as well as natural killer (NK) cells, were positive for surface expression of ILT2 (FIG. 1). Monocytes from the blood of healthy donors were also examined and found to highly express ILT2 (FIG. 2, left most panels). Upon differentiation of the monocytes into different myeloid cell populations (dendritic cells and macrophages), whether immature, inflammatory or tolerogenic, ILT2 expression was retained (FIG. 2, right panels).

ILT2 expression in different cancer indications was examined by bioinformatic analysis of the TCGA database (FIG. 3A). Interestingly, a correlation between ILT2 RNA expression levels and the presence of myeloid derived suppressor cells (MDSC) and suppressive M2 tumor associated macrophages (TAM) in the tumors of samples represented in the TCGA was observed (FIG. 3B). An analysis of fresh tumor samples from different solid tumors by flow cytometry demonstrated the expression of ILT2 by innate and adaptive immune cells in the tumor microenvironment (TME). Tumor samples from non-small cell lung cancer (NSCLC), kidney cancer (RCC), head and neck cancer, esophageal cancer and colon cancer patients were collected and single cell suspensions were generated by enzymatic digestion. The percent of ILT2 positive cells is presented in FIG. 3C for total immune cells, tumor associated macrophages (TAM), CD4 positive T cells, CD8 positive T cells and natural killer cells (NK).

Thus, it is apparent that ILT2 is expressed both on cells with anti-cancer activity (inflammatory cells) as well as on cells with cancer-promoting and immunosuppressing activity (tolerogenic and MDSCs).

Figure 4A:
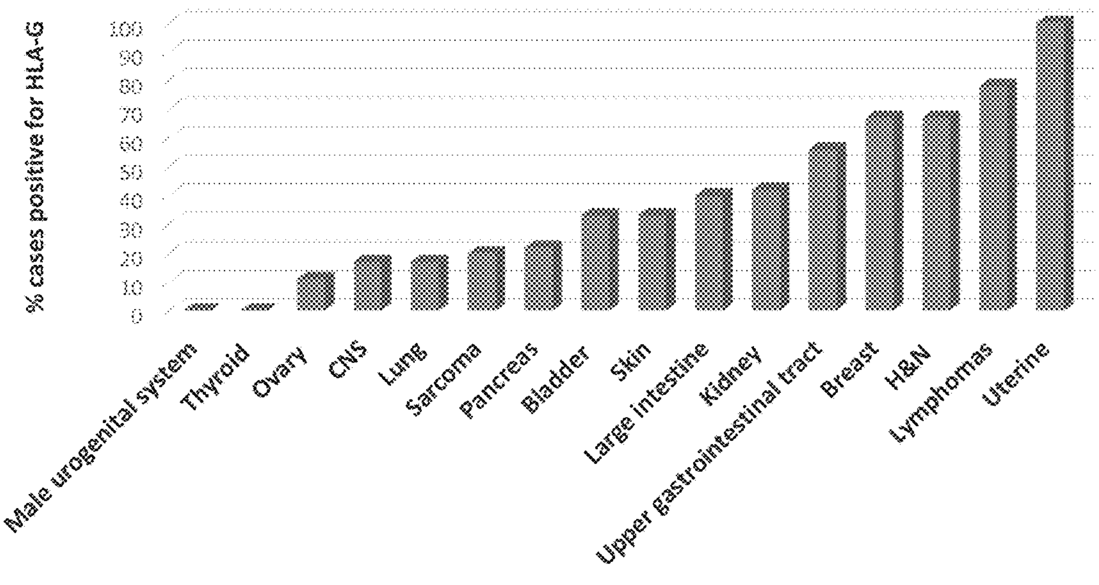
FIGS. 4A-4B. (4A) Bar graph of the percent of cases for various cancers that are HLA-G positive as determined by immunohistochemistry (IHC). (4B) Scatter plots of HLA-G IHC score for various cancers.
Figure 4B:
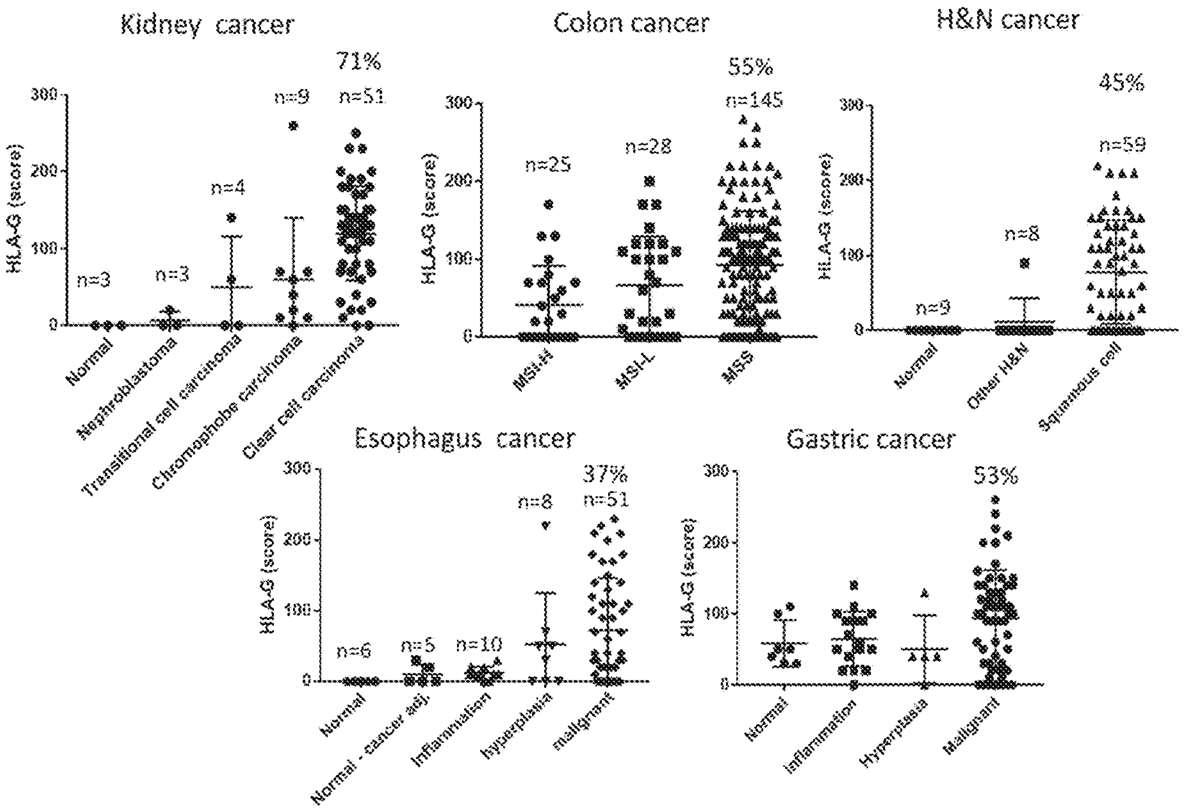

HLA-G expression was also investigated in various cancers. Tissue microarrays (TMA) of cancer samples from the different indications were stained with a commercial polyclonal HLA-G antibody by immuno-histochemistry. The percent of positive cases for each cancer type are indicated (FIG. 4A). In addition, for several indications, extended TMAs were examined. A score of HLA-G staining was calculated by the multiplication of staining intensity and the percent of positive cells. A high score of HLA-G staining of above 100 was detected in a high percentage of esophagus, gastric, head and neck and kidney cancer (FIG. 4B). Percent of positive cases in each indication are shown in Table 1.

TABLE 1

| Cancer | Tumor types | N | positive cases (%) |
|---|---|---|---|
| Male urogenital system | Prostate adenocarcinoma and testis seminoma | 6 | 0 |
| Thyroid | Thyroid carcinoma | 6 | 0 |
| Ovary | Ovary - adenocarcinoma and granular cell tumor | 8 | 11 |
| CNS | Cerebrum, Cerebellum, Eye | 15 | 17 |
| Lung | Lung - adenocarcinoma, large cell, small cell and squamous cell carcinoma | 12 | 17 |
| Sarcoma | Bone, Abdominal cavity, Retroperitoneum, soft tissue | 15 | 20 |
| Pancreas | Pancreatic adenocarcinoma | 9 | 22 |
| Bladder | Bladder transitional cell carcinoma | 3 | 33 |
| Skin | Squamous cell carcinoma and melanoma | 6 | 33 |
| Large intestine | Colon adenocarcinoma and rectal adenocarcinoma | 5 | 40 |
| Kidney | Kidney - clear cell carcinoma, nephroblastoma, chromophobe adenoma, sarcomatoid carcinoma | 12 | 42 |
| Upper gastrointestinal tract | Esophagus carcinoma and stomach adenocarcinoma | 9 | 56 |
| Breast | Breast - invasive ductal carcinoma | 3 | 67 |
| H&N | H&N - laryngeal squamous cell carcinoma | 3 | 67 |
| Lymphomas | Hodgkin's lymphoma, Diffuse small B and T cell lymphoma | 9 | 78 |

Figure 5:
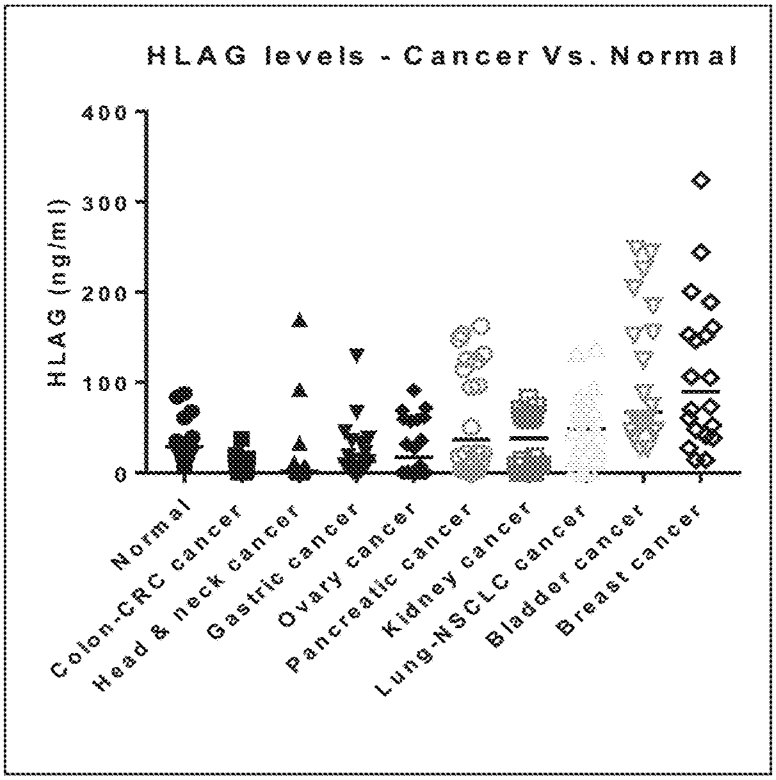
FIG. 5. Scatter plot of soluble HLA-G levels in various cancers.

HLA-G has a soluble secreted form as well as the more common membranal form. In order to examine the expression levels of soluble HLA-G in cancer patients, plasma samples were examined for the presence of HLA-G using a commercial ELISA. HLA-G was found to be overexpressed in several cancer indications as compared to normal (healthy) controls (FIG. 5). Further, in certain cancer types a population of patients with significantly higher levels could be detected.

Example 2

Generation of ILT2 Blocking Antibodies

Hybridoma technology was employed to generate monoclonal ILT2 antagonist antibodies. 69 ILT2-specific hybridomas were originally generated. 3 lead antibodies were selected according to their preferable binding, cross reactivity profile and functional activity in the various assays examined. The selected antibodies were 19E3, 15G8 and 17F2. These antibodies were sequenced using common methods. The sequences of the selected antibodies are indicated in FIG. 6. The CDRs were determined by the KABAT system. 15G8 and 19E3 were humanized using a common CDR-graftment approach. Briefly, the essential CDR and framework residues from the original hybridoma-derived antibodies were identified and grafted into the variable and constant regions of germline human antibodies. The final humanized antibodies are IgG4 antibodies. The final humanized 15G8 also contained a single amino acid change, removing the cysteine in CDR-H3 and replace it with alanine or serine. This change was made in order to improve developability. The binding of both resulting antibodies were confirmed, and the 15G8 antibody with an alanine was selected for further testing. All future references to humanized 15G8 refer to the alanine variant.

Figure 7B:
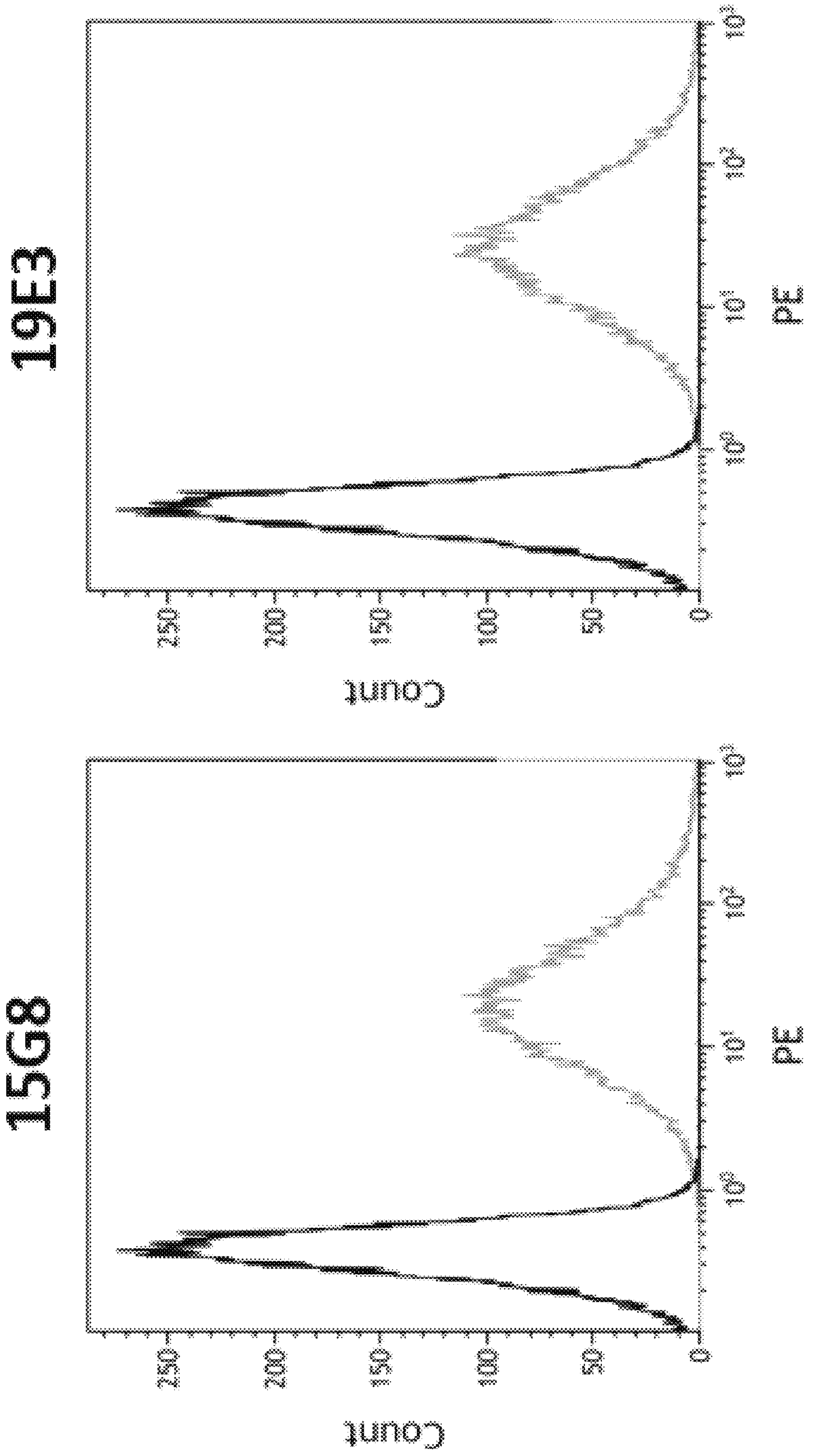
Figure 7B:
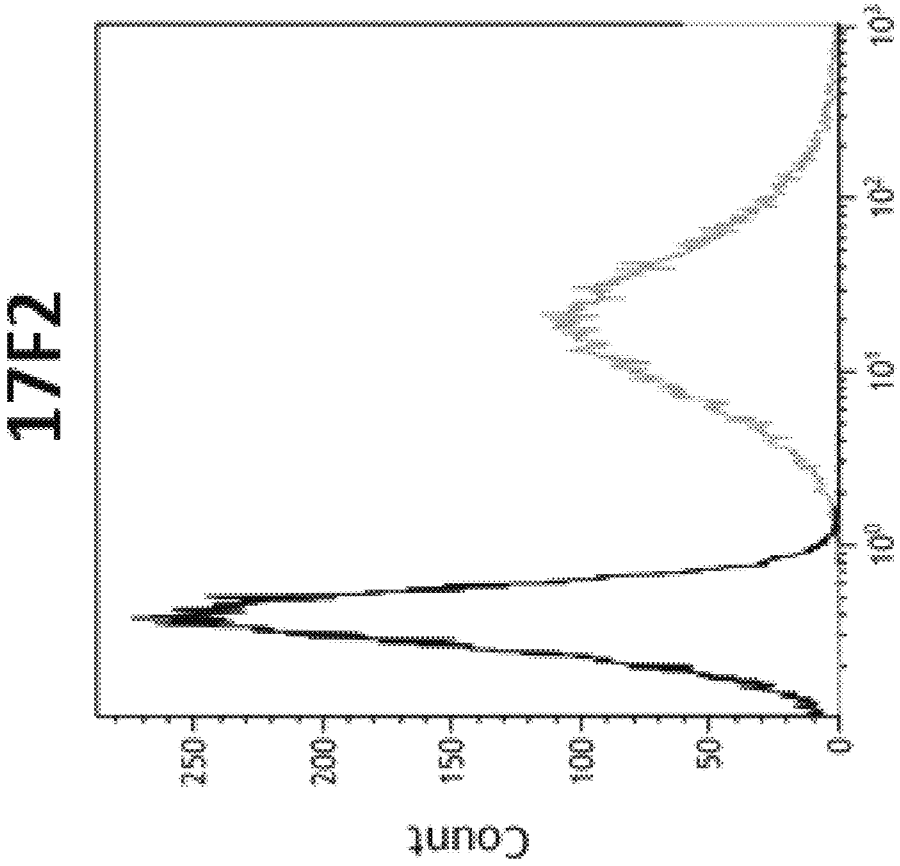
Figure 7C:
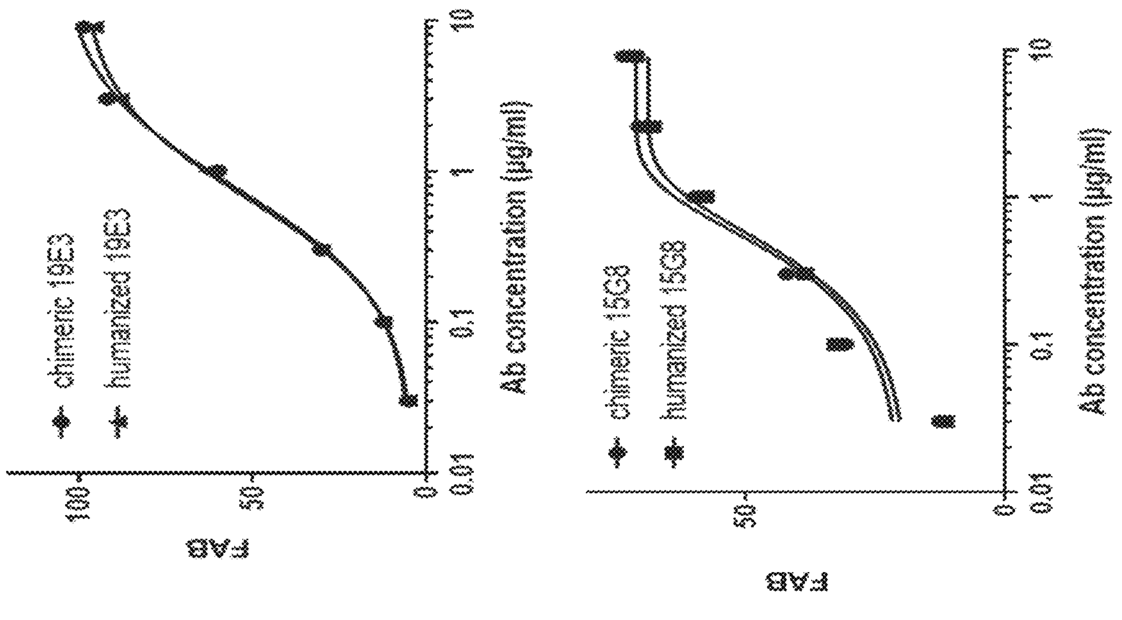
Figure 7D:
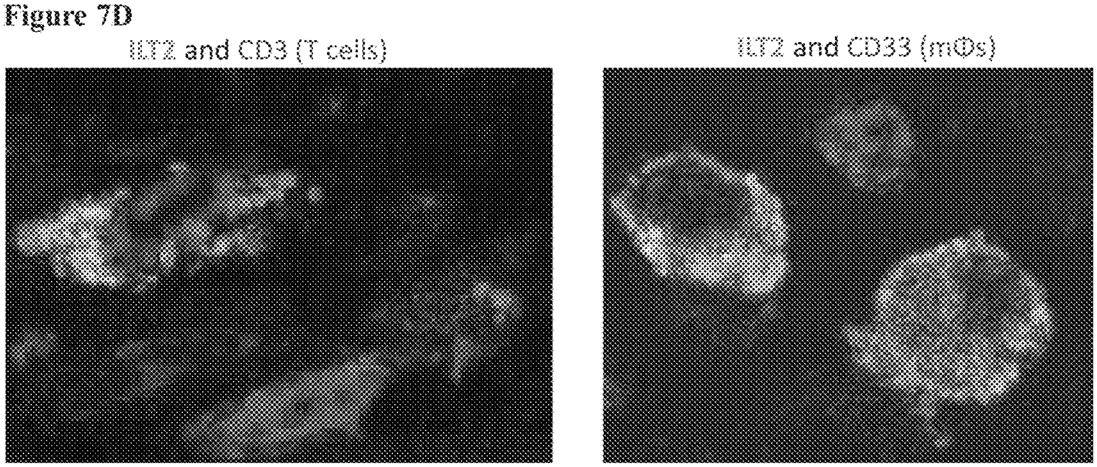
Figure 7E:
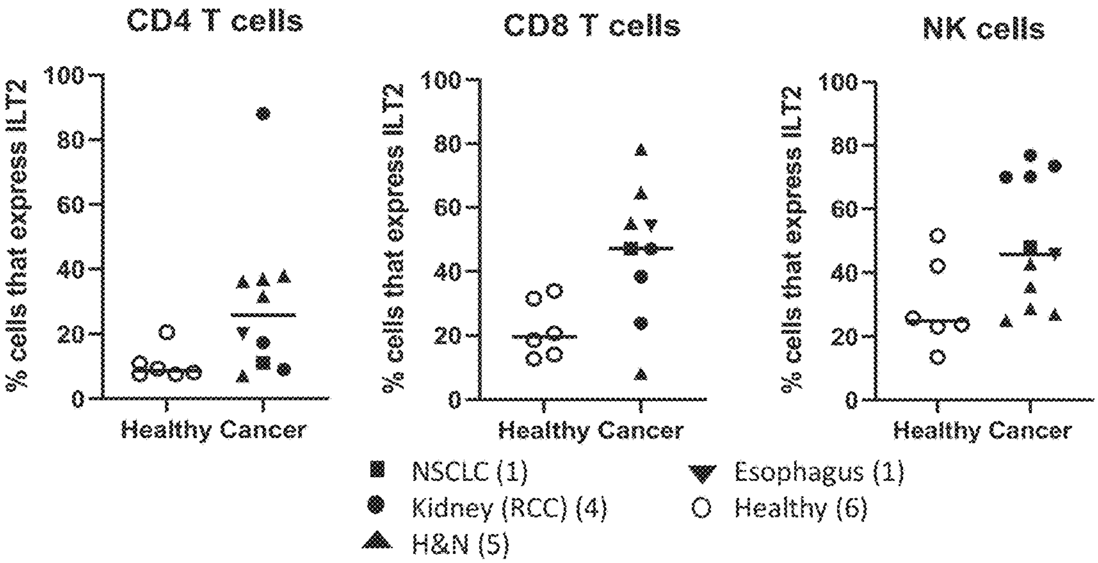

The ability of the anti-ILT2 antibodies to bind to ILT2 was tested using three different systems. Binding to recombinant ILT2 was tested using ELISA (FIG. 7A), and using a Biacore T200 (Table 2), and binding to membranal ILT2 was tested using BW cells transfected with ILT2 (FIG. 7B). The chimeric murine and humanized antibodies showed similar binding (FIG. 7C). A commercial mouse anti-human ILT2 antibody (Biolegend; clone GHI/75) was used as a positive control. The three tested antibodies successfully bound ILT2 whether in solution or on the surface of cells. Cross-reactivity to several similar ILT family members—PIRB, ILT6 and LILRA1 was examined using binding ELISA as well. Antibodies to these proteins were used as positive control. None of the antibodies cross-reacted with PIRB, ILT6 and LILRA1. The antibodies were also effective for immunostaining (FIG. 7D). Interestingly, when PBMCs were isolated from the blood of cancer patients, it was found that ILT2 was expressed on more T cells and NK cells in the cancer patients than in healthy controls (FIG. 7E).

TABLE 2

| Ka (1/Ms) | Kd (1/s) | KD (/M) |
|---|---|---|
| 1.37-1.76E+06 | 2.22-5.22E−03 | 1.26-3.16E−09 |

Example 3

ILT2 Antibodies Block ILT2-HLA-G Interaction

Figure 8A:
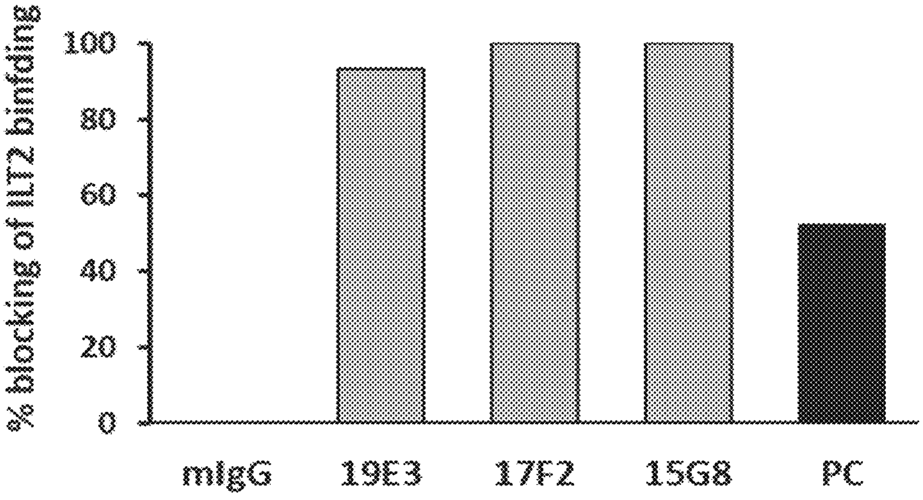
FIGS. 8A-8P. (8A) Bar graph of percent blocking for each ILT2 antibody and a positive control (PC, GHI/75 antibody). (8B) Histogram of ILT2-biotin binding to cells expressing HLA-G in the presence of an ILT2 blocking antibody. The binding of ILT2-biotin to the cells was determined using Streptavidin-PE by flow cytometry analysis. No antibody (grey line), 15G8 (light grey line), isotype control (black line). (8C) A line graph of blocking activity of the 15G8 humanized antibody as determined by ILT2-biotin binding to cells expressing HLA-G. (8D) Line graph of the blocking activity of chimeric and humanized 19E3 (left panel) and of chimeric and humanized 15G8 (right panel) as determined by the binding of ILT2-biotin to cells expressing HLA-G in the presence of the antibodies. (8E) Bar graph of mouse IL-2 secretion from cells expressing an ILT2 signaling reporter construct in the presence of HLA-G-expressing cells and the presence or absence of ILT2 blocking antibodies. PC=positive control (GHI/75 antibody). (8F) A line graph of blocking activity of the 15G8 humanized antibody as determined by reporter assay. (SG) A bar graph of mouse IL-2 secretion from cells expressing an ILT2 signaling reporter construct in the presence or absence of ILT2 blocking antibody and a positive control antibody. (8H-8K) Bar graph of human IL-2 secretion from Jurkat cells (8H) lacking ILT2, or (8I-8K) expressing ILT2 cocultured with A375 cancer cells (8I) with only MHC-I expression or (8J-8K) expressing both MHC-I and exogenous HLA-G in the presence or absence of ILT2 blocking antibody and a positive control (8I-J) pan-HLA antibody or (8K) HLA-G specific antibody. (8L-8N) Bar graphs of human IL-2 secretion from Jurakt cells expressing ILT2 cultured with A375 cancer cells expressing HLA-G in the presence or absence of (8L) the 15G8 antibody. (8M) the GHI/75 antibody and (8N) the HP-F1 antibody. (8O-8P) Dot plots of expression of activation markers (8O) phosphorylated ZAP70 and (8P) phosphorylated Syk in TIL cells and NK cells, respectively, incubated with HLA-G-positive cancer cells with and without the presence of 15G8 antibody.
Figure 8B:
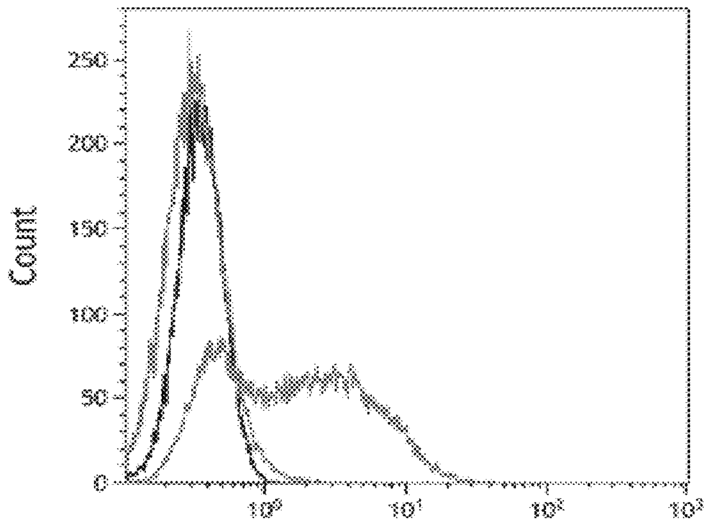
Figure 8C:
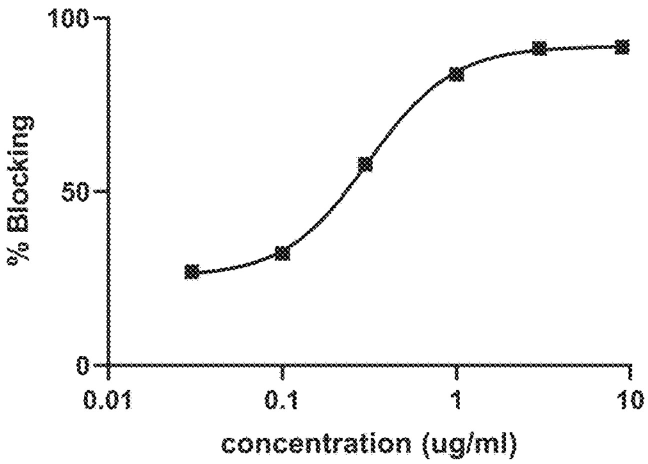
Figure 8D:
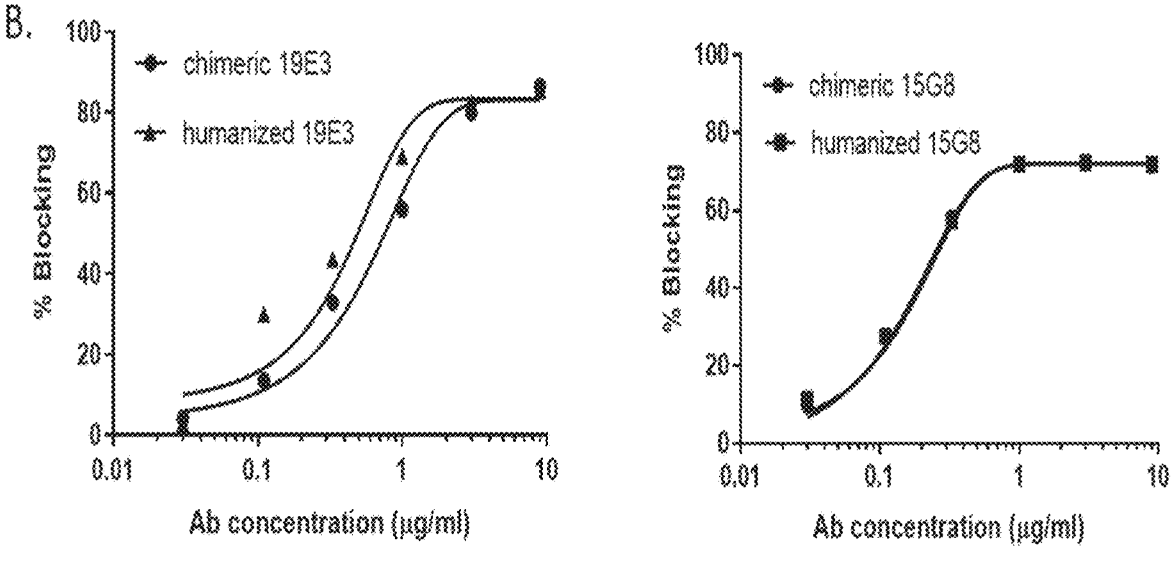

The ability of the generated anti-ILT2 antibodies to block the interaction between HLA-G and ILT2 was tested using four different assays. First, a blocking flow cytometry assay was performed. HLA-G transfected A375 cells were incubated with biotinylated ILT2 in the presence of the antibodies of the invention and a positive control antibody. The commercially available anti-ILT2 antibody GH1/75 (BioLegend, cat #333704) was used as the positive control. The binding of ILT2-biotin to the cells was determined using Streptavidin-PE by flow cytometry analysis (FIG. 8A). The percent of blocking was determined by normalizing to a negative control (ILT2 binding in the presence of control IgG). A representative FACS analysis showing ILT2 binding without antibody (grey line), in the presence of 15G8 (light grey line), and the isotype control (black line) is presented in FIG. 8B. The percentage of blocking was calculated at various concentrations of antibody (FIG. 8C). The chimeric murine and humanized antibodies showed similar blocking ability (FIG. 8D).

Figure 8E:
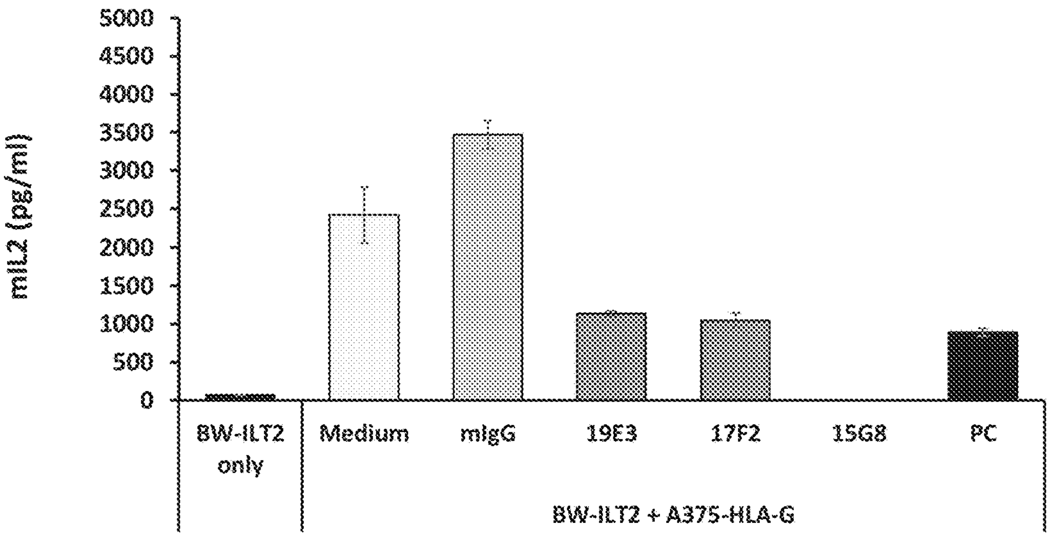
Figure 8F:
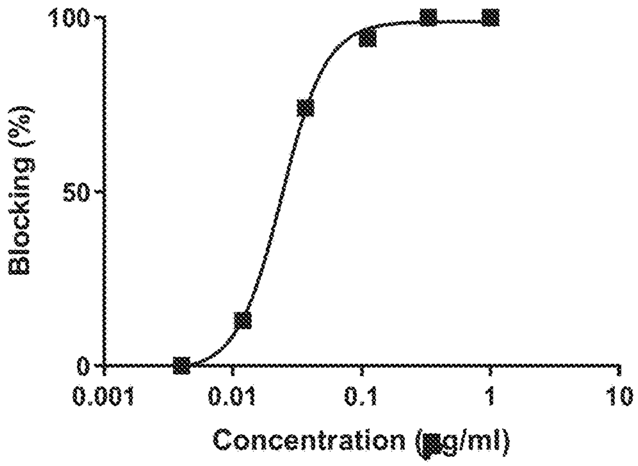
Figure 8G:
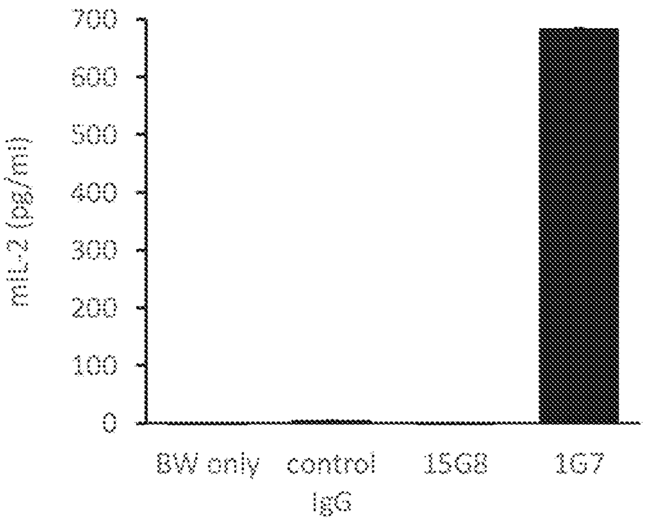

The ability of ILT2 antibodies to functionally block the interaction between HLA-G and ILT2 was also examined in a BW ILT2/mouse Z-chain chimera reporter assay. BW cells were transfected with human ILT2 fused to a mouse T cell zeta chain (BW-ILT2). The cells were then incubated with A375-HLA-G cells in the presence of the selected ILT2 antibodies. Upon a functional ILT2-HLA-G interaction the BW cells secrete a reporter cytokine, mouse IL-2. Blocking of the interaction would reduce secretion of the reporter cytokine. The secretion of a mouse IL-2 was determined by ELISA after 24 hours of incubation. The results represent an average of mIL-2 levels±SE from triplicate wells per treatment (FIG. 8E). A commercial mouse anti-human ILT2 antibody (Biolegend; clone GHI/75) was used as a positive control (PC) for both assays. The percentage of blocking was calculated at various concentrations of antibody (FIG. 8F). This same BW ILT2/mouse Z-chain chimera reporter assay was used to rule out the possibility that the new antibodies might have an ILT2 activating effect on their own. The cells were incubated with the ILT2 antibodies without the cancer cells and mouse IL-2 secretion was again measured (FIG. 8G). The new ILT2 antibodies were found to have no agonistic effect, though other antibodies generated by the same hybridoma process (1G7) can bind ILT2 and induce its activity.

Figure 8H:
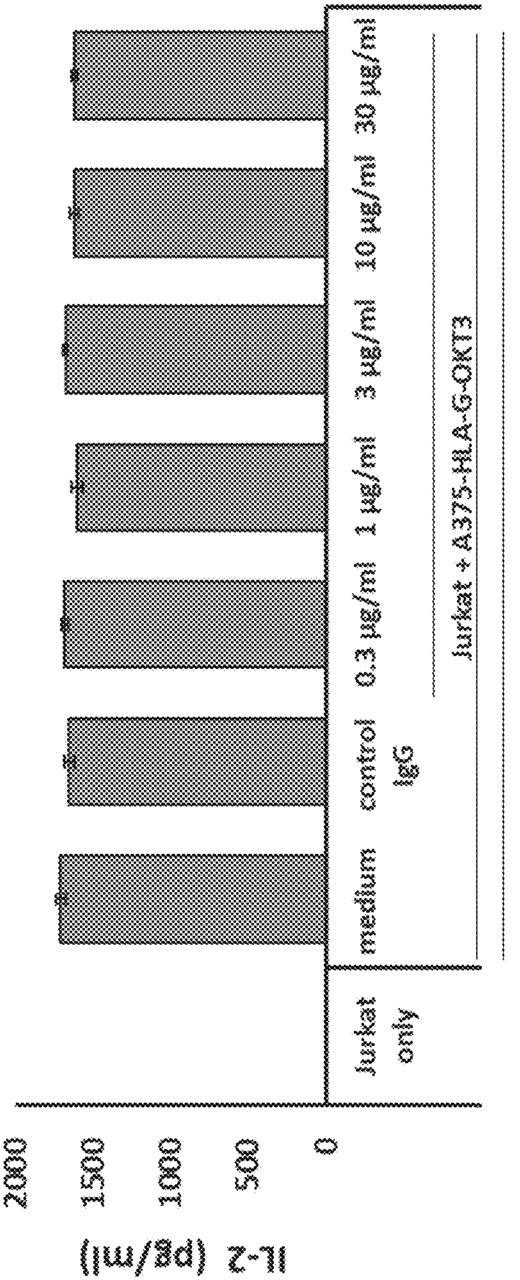
Figure 8I:
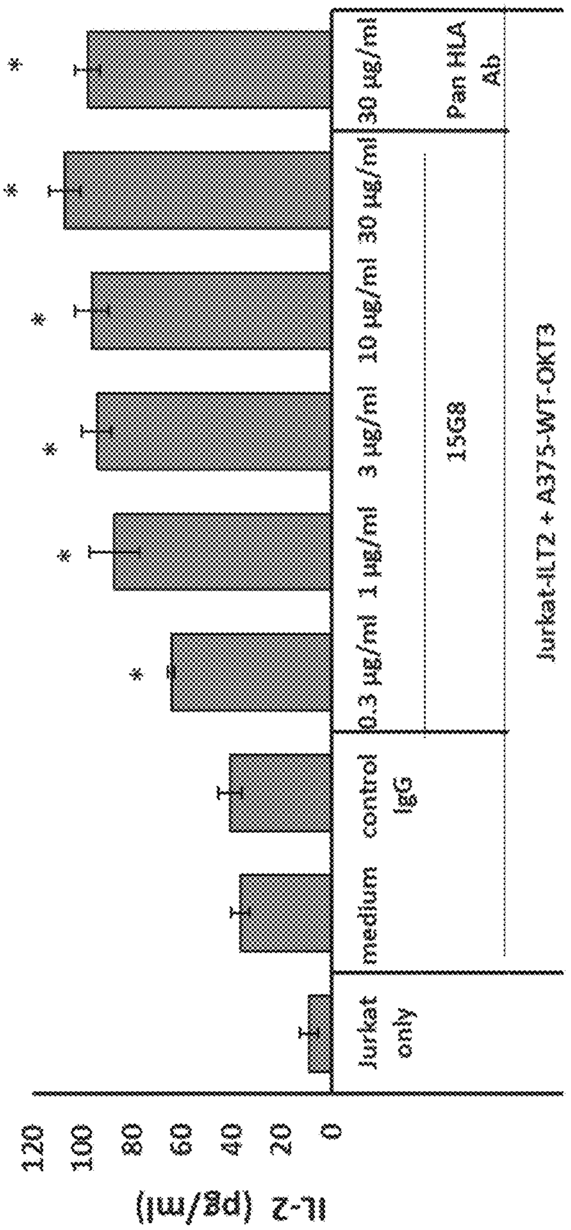
Figure 8J:
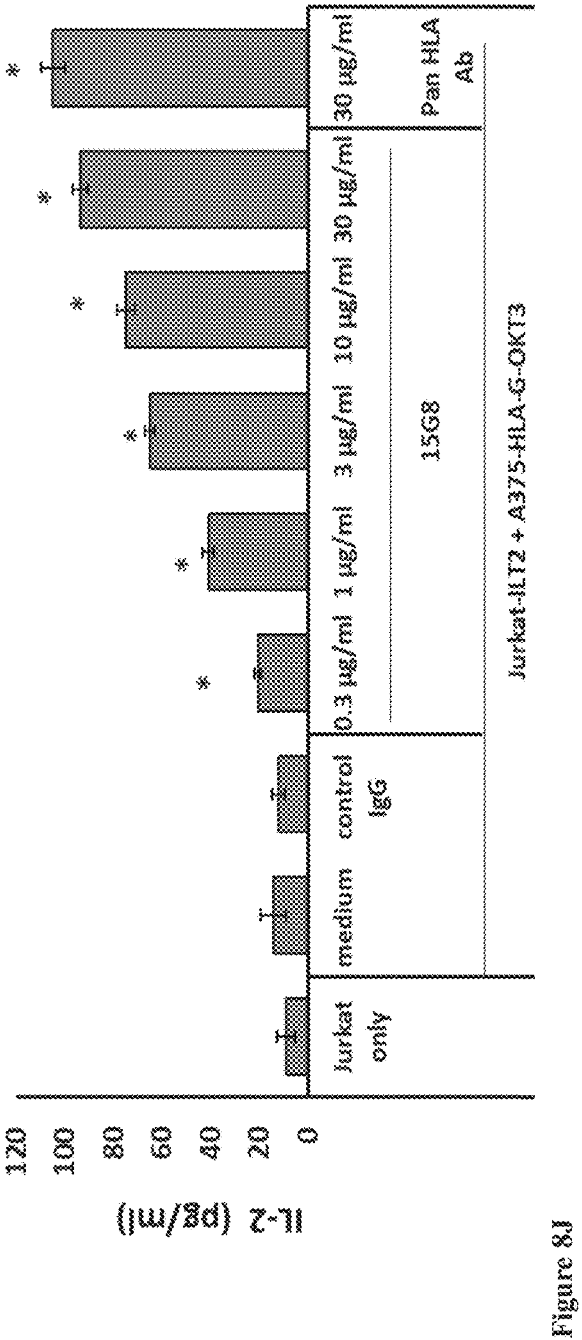
Figure 8K:
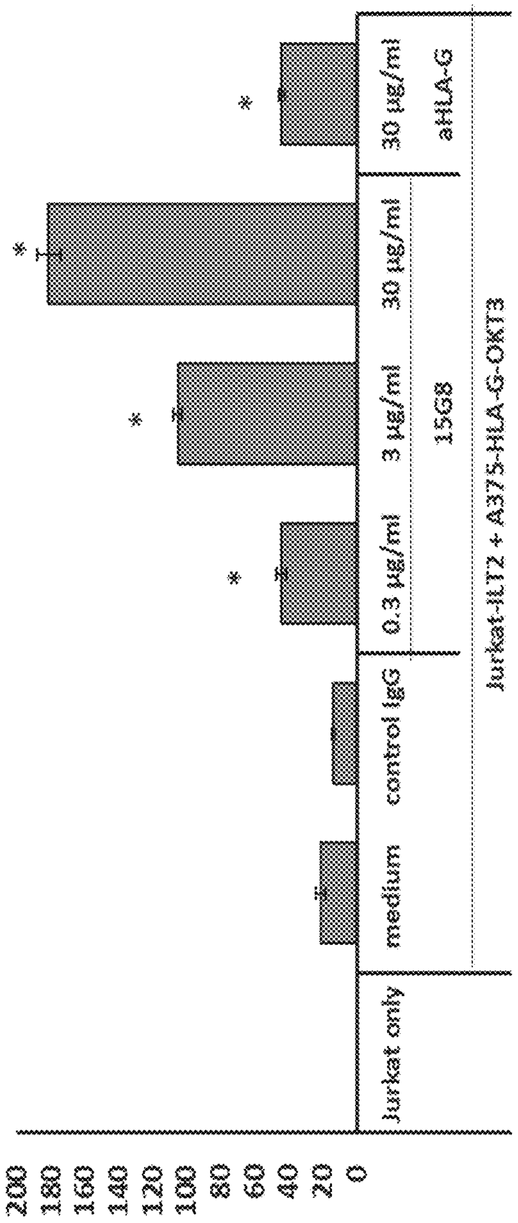

Functional blocking was also examined in human Jurkat cells (T cells). Jurkat cells were incubated with or without A375 cancer cells exogenously expressing HLA-G and a single chain anti-CD3 (OKT3). Secretion of pro-inflammatory human IL-2 was measured. When unmodified Jurkat cells were used (cells which are ILT2 negative) high levels of IL-2 were secreted when the Jurkat cells were cocultured with the cancer cells (FIG. 8H). Not surprisingly, the addition of the 15G8 antibody had no effect on IL-2 secretion as there was no ILT2 to block. Jurkat cells were therefore transfected to express human ILT2. First, the ILT2-positive Jurkat cells were cultured with and without A375 cancer cell exogenously expressing OKT3. These cancer cells are naturally MHC-I positive. The MHC-I from the cancer cells strongly inhibited IL-2 secretion (FIG. 8I). In this case, addition of the 15G8 antibody blocked the ILT2/MHC-I interaction and increased IL-2 secretion in a dose dependent manner. A pan-HLA antibody was used as a positive control, and at equal concentrations the 15G8 antibody was comparable to the pan-HLA antibody (FIG. 8I). In order to enhance the inhibitory effect, the A375 cells were also transfected with HLA-G, making them MHC-I and HLA-G positive. These cells produced an even stronger inhibitory effect on the ILT2 positive cells, reducing IL-2 secretion to that of Jurkat cells cultured alone (FIG. 8J). A dose dependent effect was again observed when the 15G8 antibody was administered, and again at an equal dosage the 15G8 antibody and pan-HLA antibody were comparably effective (FIG. 8J). Notably, when only an HLA-G specific antibody was used instead of the pan-HLA the effect was greatly reduced and was comparable to the 15G8 antibody used at ⅟100$^{th}$ of the concentration (FIG. 8K).

Figure 8L:
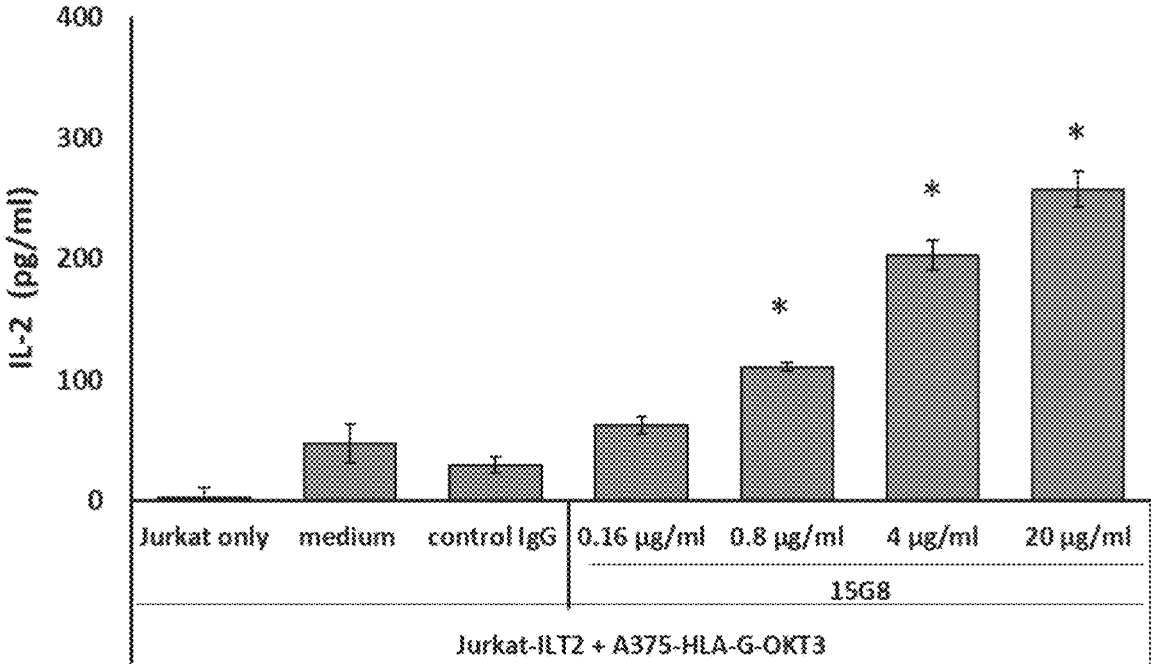
Figure 8M:
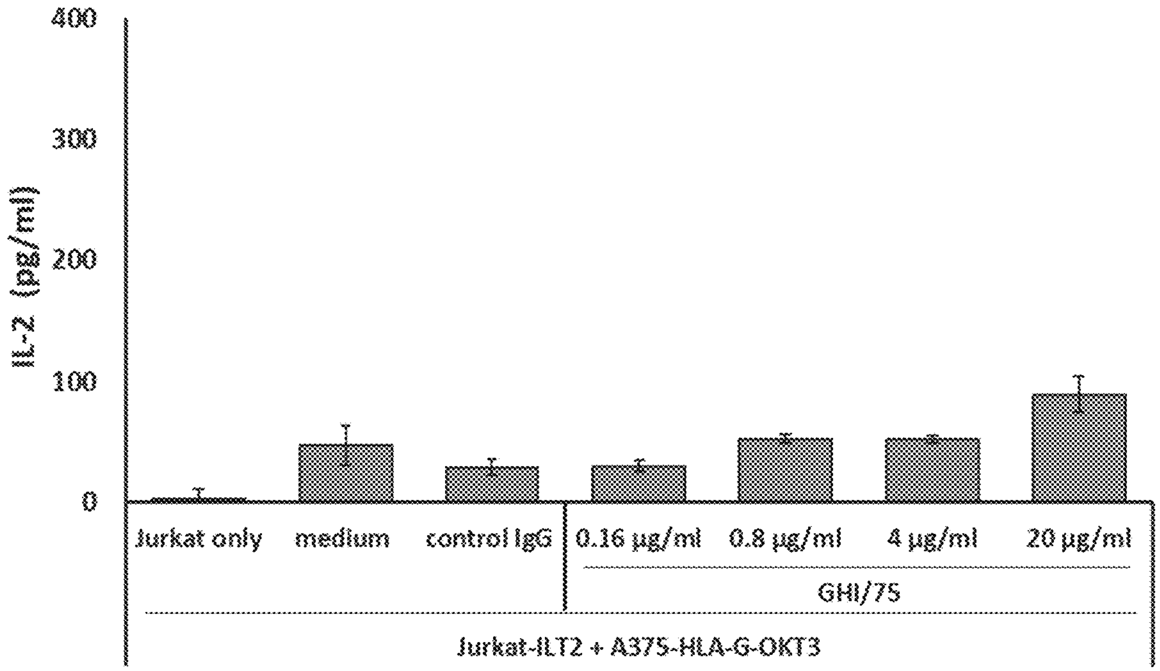
Figure 8N:
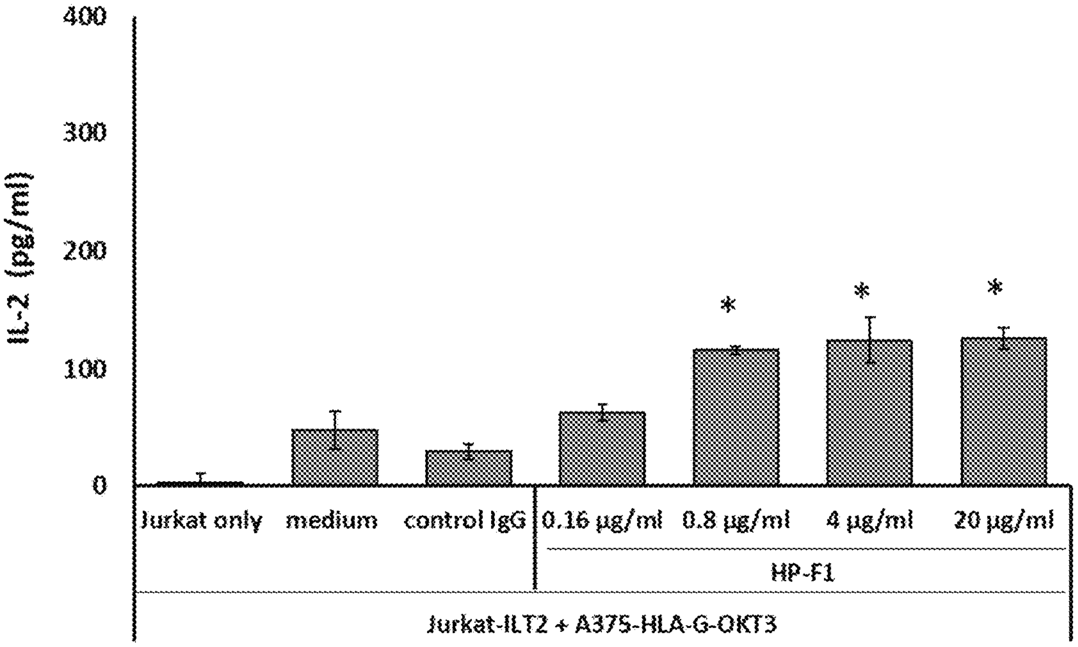

This Jurkat system was also used to compare the 15G8 antibody to two commercially available antibodies: GHI/75 and HP-F1. Jurkat cells expressing human ILT2 were cultured with A375 cells expression HLA-G/OKT3 in the presence and absence of various concentrations of 15G8, GHI/75 and HP-F1. As already observed, 15G8 caused a statistically significant, dose dependent, increase in IL-2 secretion (FIG. 8L). GHI/75 had no effect on IL2 secretion as compared to medium alone but resulted in a small increase as compared to the IgG control (FIG. 8M). HP-F1 produced a small but significant increase that plateaued and did not increase with increased dosing (FIG. 8N). Even at 20 μg/ml HP-F1 was inferior as compared to only 4 μg/ml of 15G8.

Figure 8O:
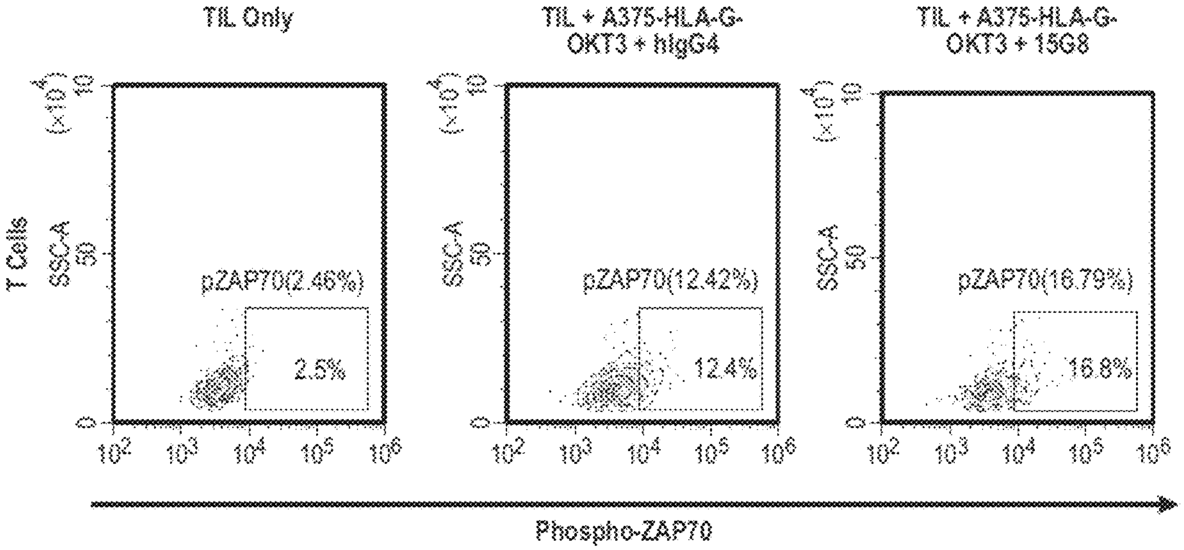
Figure 8P:
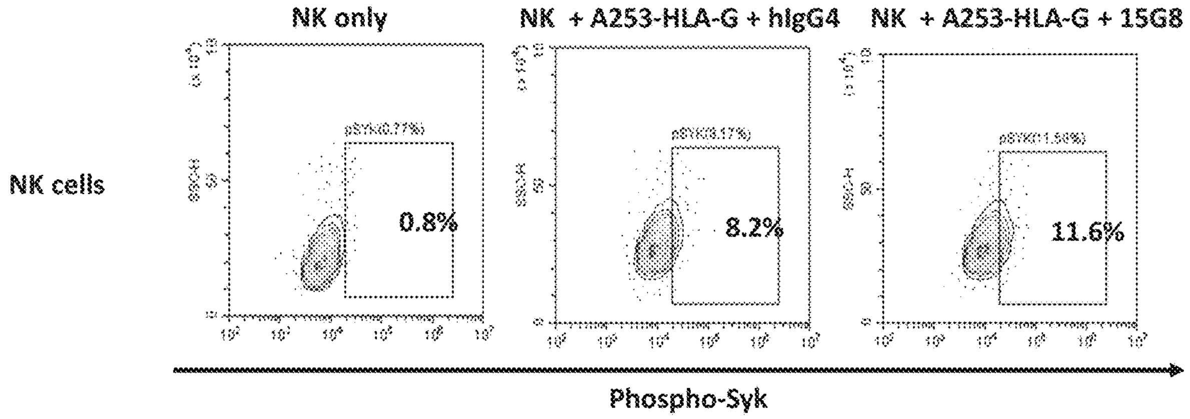

Lastly, activation was directly measured in TILs, and NK cells. TILs were incubated with A375-HLA-G-OKT3 cells for 5 minutes followed by detection of the T cell activation marker, phosphorylated ZAP70. NK cells were incubated with A253-HLA-G cells for 2 minutes followed by detection of the NK cell activation marker, phosphorylated Syk. Activation was observed in both cell types when cocultured with cancer cells, however this activation was enhanced in the presence of ILT2 antibody (FIG. 8O-8P). These results demonstrate that the ILT2 antibodies can efficiently block the ILT2-HLA-G interaction which results in enhanced T cell and NK cell activation.

Example 4

Figure 9A:
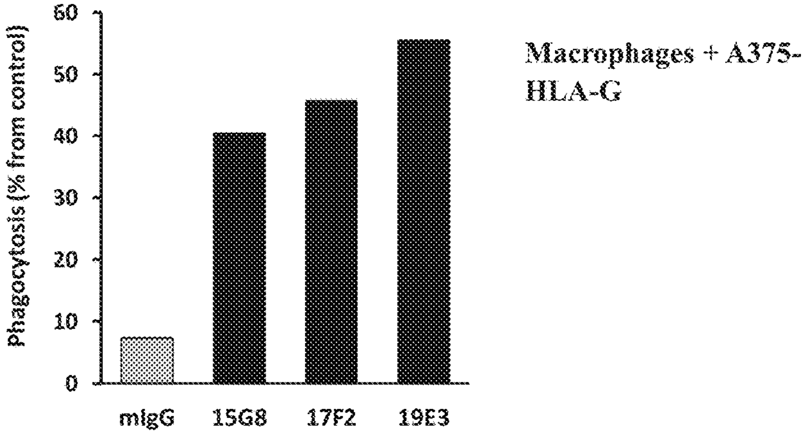
FIGS. 9A-9D. (9A) Bar graph measuring phagocytosis as percent from control of HLA-G expressing cancer cells cocultured with macrophages in the presence of ILT2 antibodies as determined by a FACS-based method. (9B) Line graph of real-time phagocytosis of cancer cells by macrophages in the presence of the ILT2 antibodies as determined by an Incucyte® system. (9C) Bar graphs measuring phagocytosis as percent from control of various HLA-G and MHC-I expressing cancer cells cocultured with macrophages in the presence of the ILT2 antibody 15G8. (9D) Bar graph of phagocytosis by macrophages cocultured with A253-HLA-G cells in the presence of ILT2 antibodies, Erbitux, hIgG control or their combinations.
Figure 9B:
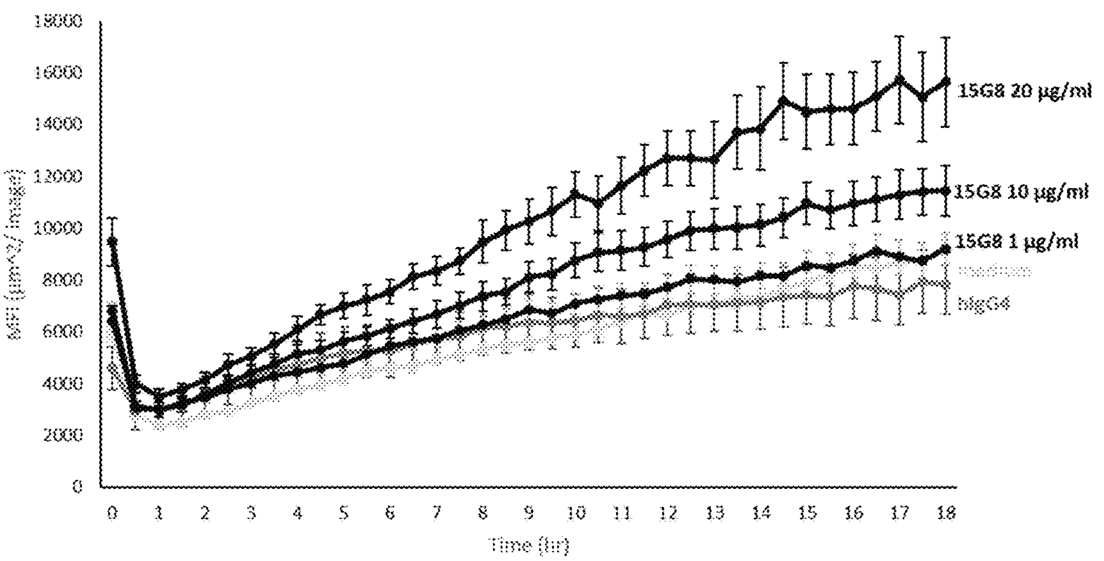
Figure 9C:
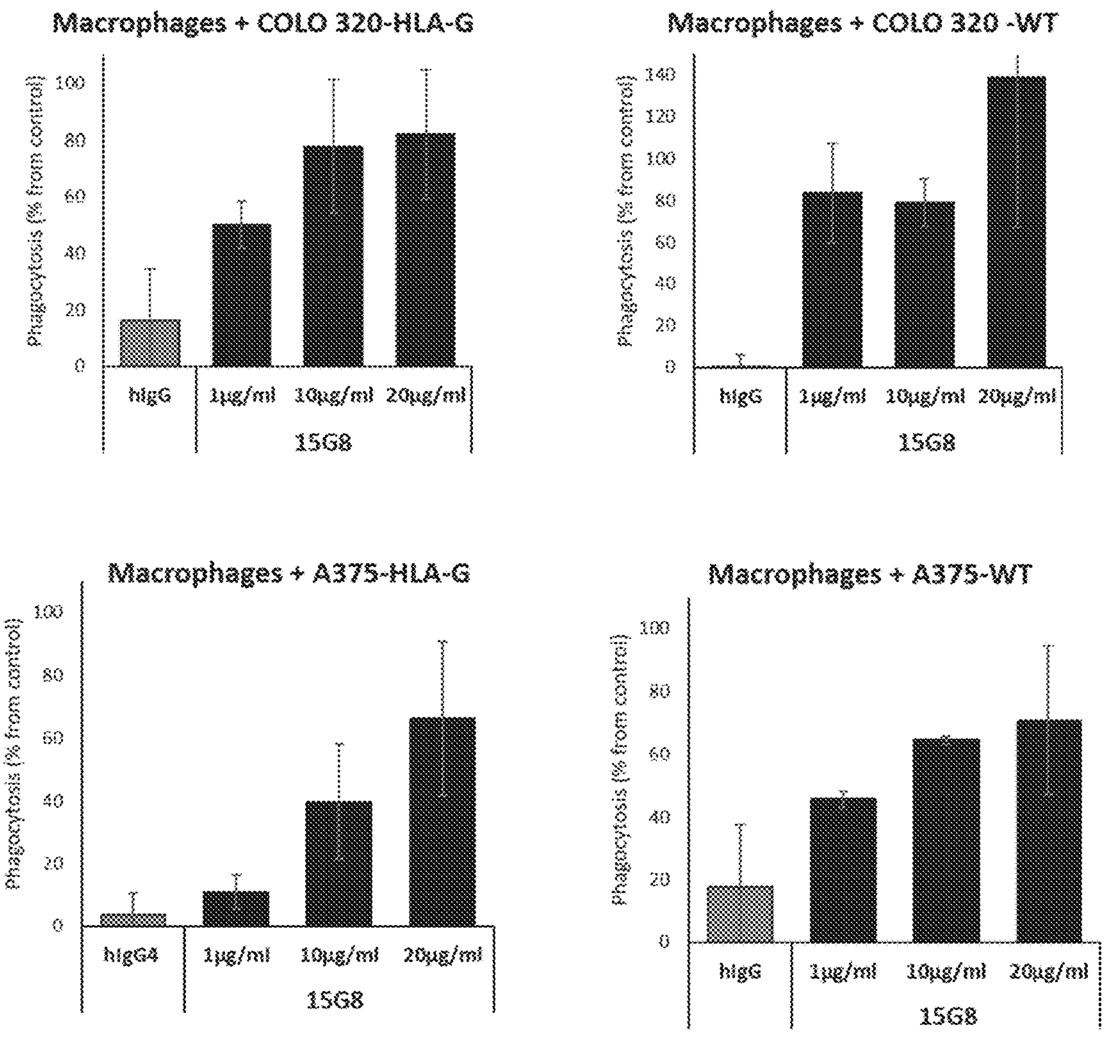

ILT2 Antibodies Enhance the Phagocytosis of HLA-G and MHC-I-Positive Tumor Cells The ability of the generated anti-ILT2 antibodies to enhance the phagocytosis of tumor cells was tested using two different systems. Monocytes were isolated from the blood of healthy donors and incubated for 6-7 days in the presence of M-CSF to generate macrophages. First, a flow cytometry-based assay was employed. Different cancer cell lines stained with PKH67-FITC were incubated with the macrophages which were stained with eFluor 670-APC in the presence of the indicated antibodies. Phagocytosis levels were determined by the percent of macrophages which were double stained indicating the engulfment of the target cells. Phagocytosis levels are presented as percent from control (medium only). As demonstrated in FIG. 9A, the different ILT2 blocking antibodies could enhance the phagocytosis of HLA-G positive A375 cells by macrophages. In addition, the ability of macrophages to enhance the phagocytosis of tumor cells was examined using a real-time IncuCyte® analysis system. Target cell lines were labeled with pHrodo™ Red Cell Labeling Dye, washed and added to macrophages along with various treatments in replicates. The fluorescence of the IncuCyte® pHrodo™ Red Cell Labeling Dye is increased in an acidic environment such as the one that is resident in the phagosome, thus enabling the quantitation of phagocytosis events by measurement of fluorescence. The IncuCyte® instrument sampled the assay plate every 30 min for fluorescent red signal intensity and phase images. Phagocytosis events are reflected as accumulation of red fluorescent signal and the phagocytosis rate was reflected from the kinetics of red fluorescent signal accumulation. Using this real-time system, the ability of a humanized anti-ILT2 antibody to enhance the phagocytosis of HLA-G positive A375 cells was confirmed (FIG. 9B). In addition, using the IncuCyte® system, it was demonstrated that the generated blocking ILT2 antibodies can enhance the phagocytosis of both HLA-G positive as well as various MHC-1 positive (WT) cancer cell lines (FIG. 9C).

Figure 9D:
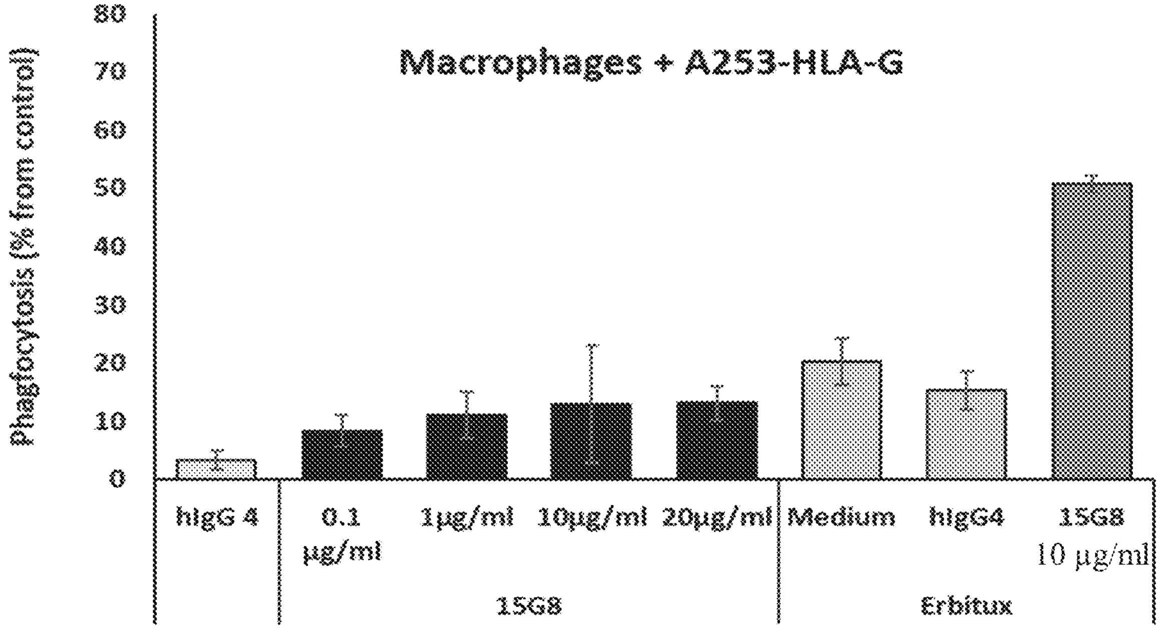

The effect of combining the generated ILT2 antibodies with the antibody-dependent cellular phagocytosis (ADCP) inducing antibody. Erbitux, on phagocytosis of cancer cells was examined using the IncuCyte® real-time system described above. The combination of the ILT2 blocking antibody with Erbitux significantly increased the phagocytosis of a cancer cell line overexpressing HLA-G (FIG. 9D) in comparison to the activity of each antibody alone. Indeed, the combination of Erbitux and the 15G8 humanized antibody had a synergistic effect, with the increase in phagocytosis of the combination treatment being larger than merely additive.

Example 5

Figure 10A:
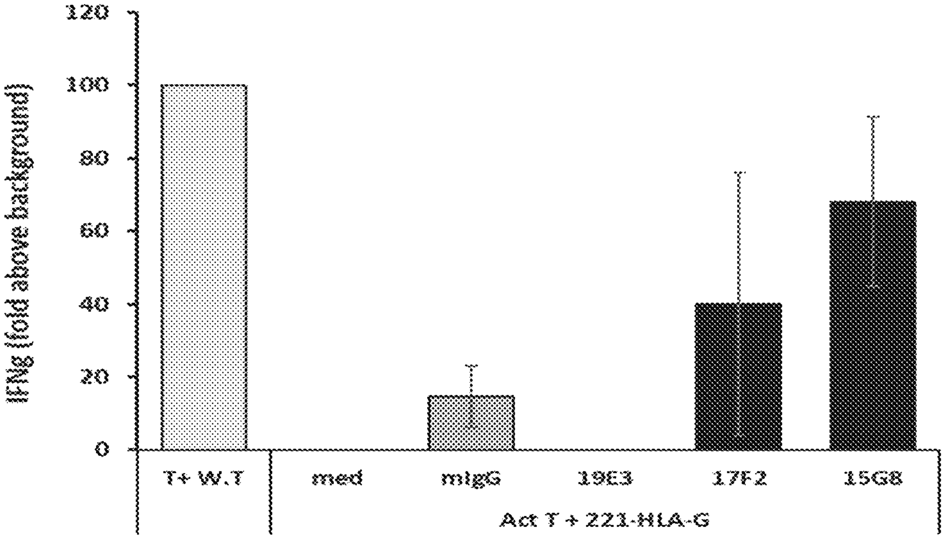
FIGS. 10A-10B. Bar graphs of IFNγ secretion and granzyme B secretion from activated CD8 T cells co-cultured with (10A) wild-type 721.221 cells or HLA-G expressing 721.221 cells or (10B) HLA-G expression A375 cells in the presence of ILT2 antibodies.
Figure 10B:
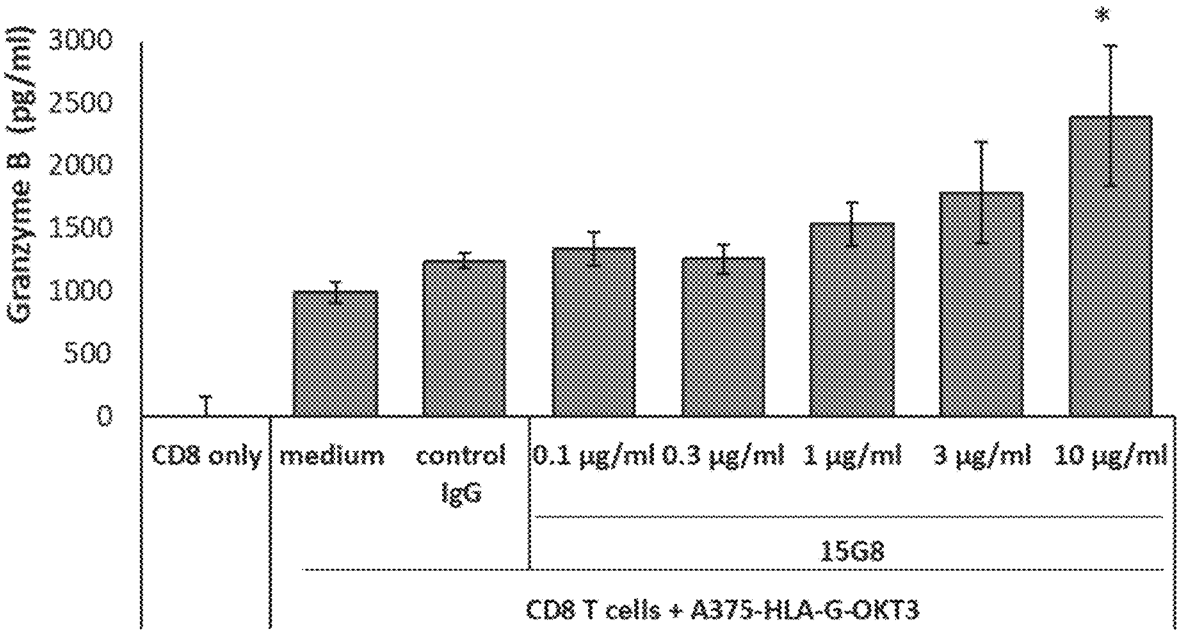

Selected ILT2 Antibodies can Restore T Cell Activity which is Inhibited by HLA-G In order to examine the ability of the generated anti-ILT2 antibodies to restore T cell activity which was inhibited by HLA-G, human CD8 T cells were co-incubated with either wild type 721.221 cells (221 WT) or 721.221 cells which overexpress the soluble HLA-G5 (221-HLA-G). IFNγ secretion levels from the T cells were measured following 5 days using a standard ELISA. The results are demonstrated as percent of fold above the effect of 221-HLA-G only and represent an average of 4 independent experiments. The results displayed in FIG. 10A demonstrate that several ILT2 antibodies can restore HLA-G-inhibited T cell activity. This was also tested with incubation with A375-HLA-G-OKT3 cells. After 72 hours secretion of human granzyme B was also measured and was found to be increased in the presence of 15G8 antibody in a dose dependent manner (FIG. 10B).

Example 6

Selected ILT2 Antibodies can Enhance NK Cytotoxicity Against HLA-G and MHC-I-Positive Tumor Cells The ability of the generated anti-ILT2 antibodies to enhance NK cells effector activity was tested in a system in which NK cells were incubated with various target cancer cell lines. The cells were co-incubated for 5 hours at effector-to-target ratio of 7.5:1, followed by the detection of cytotoxicity levels using a fluorometric LDH detection kit. Percent of specific cytotoxicity was calculated as follows:

$$\%\ \text{Cytotoxicity} = \frac{100 \times (\text{Test sample} - \text{Low control (target cells only)})}{\left(\begin{array}{c}\text{High control (target cells in lysic buffer)} - \\ \text{Low control-effectors only}\end{array}\right)}$$

Figure 11B:
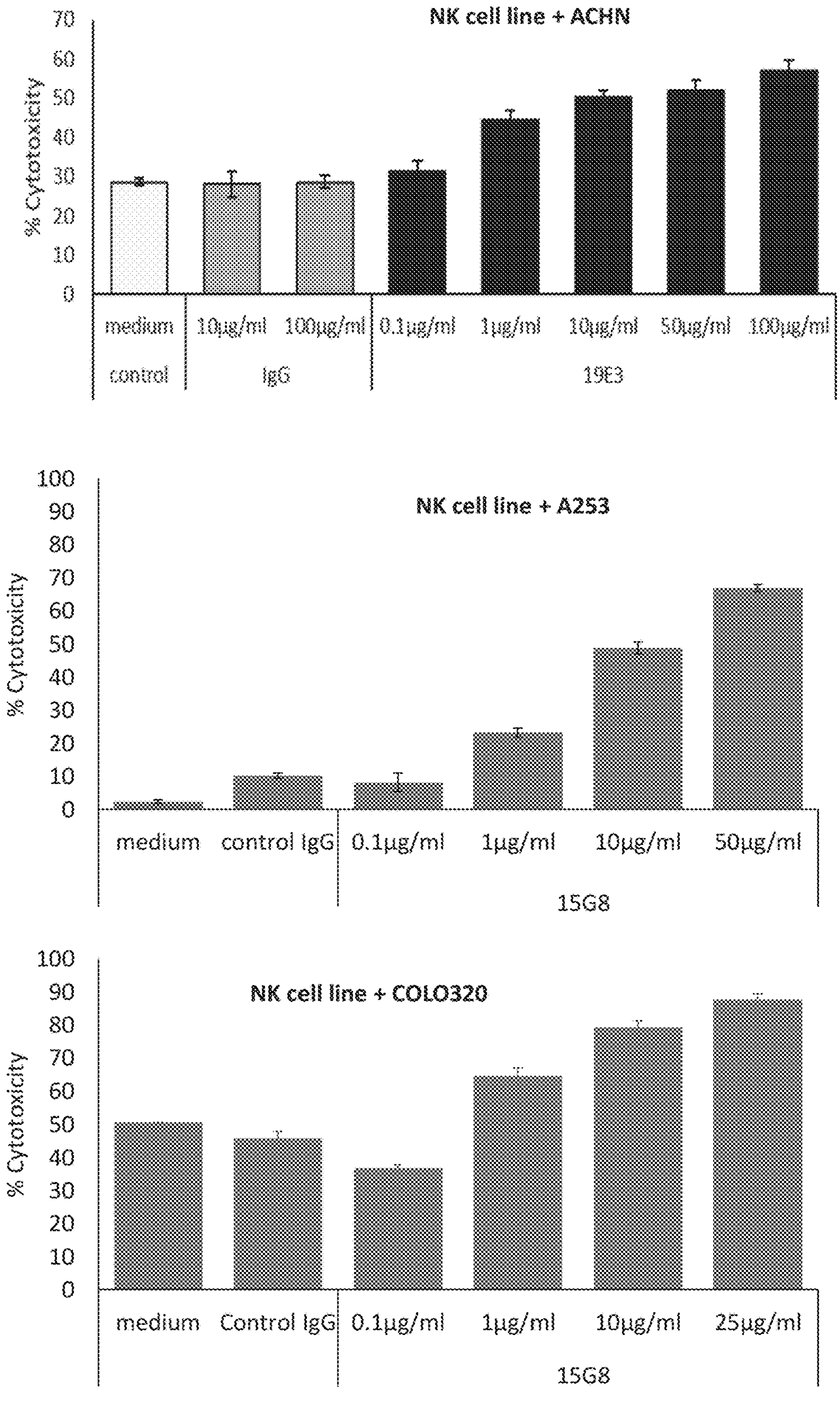
Figure 11C:
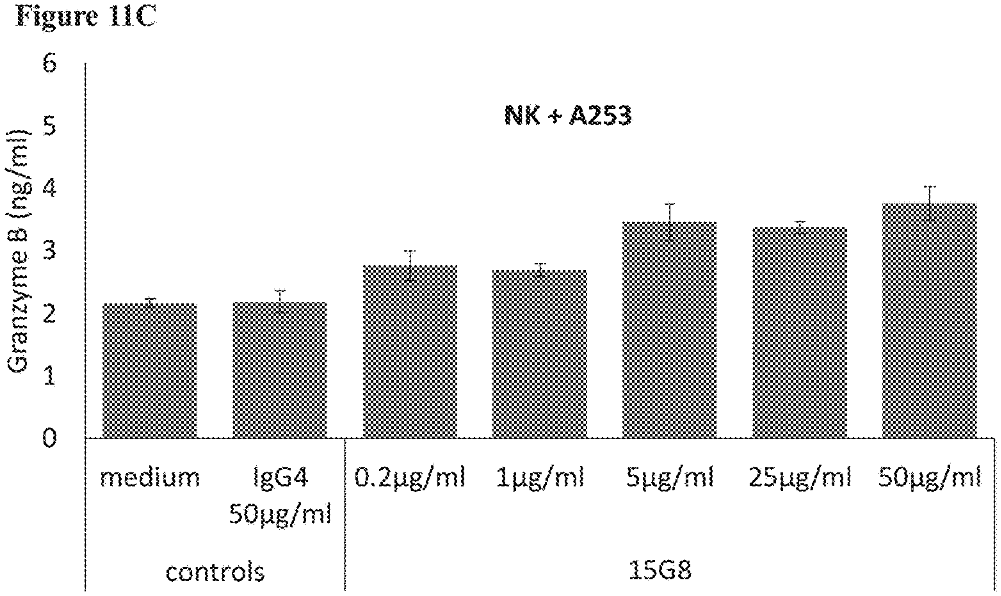
Figure 11D:
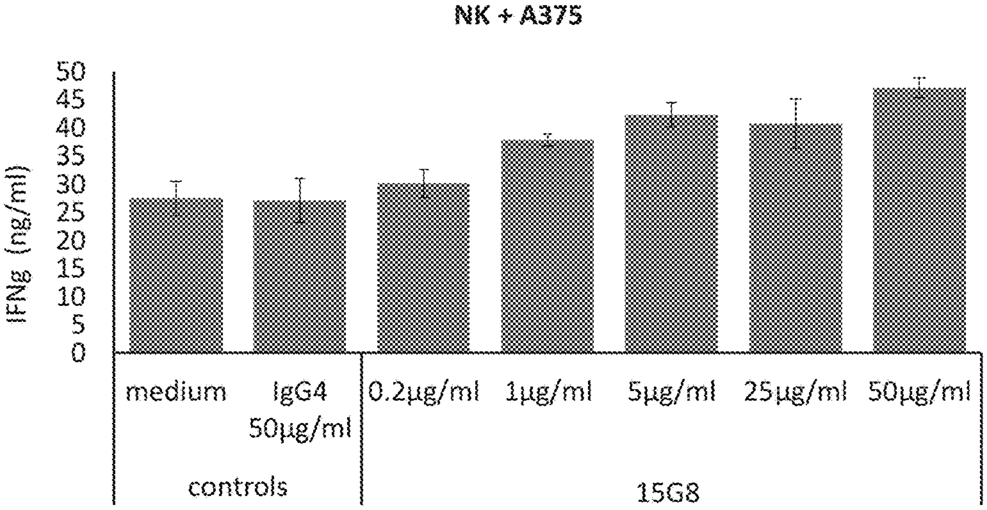
Figure 11E:
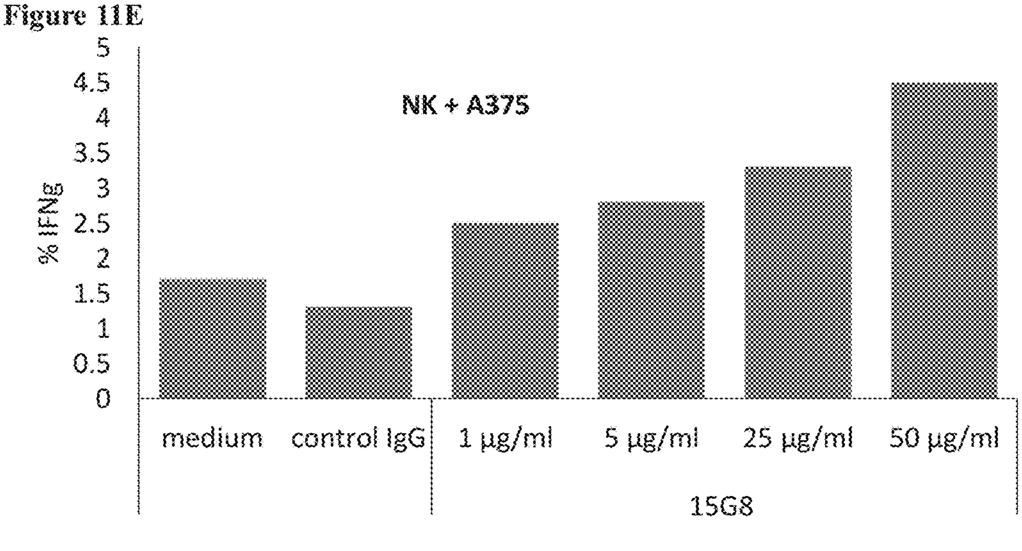
Figure 11F:
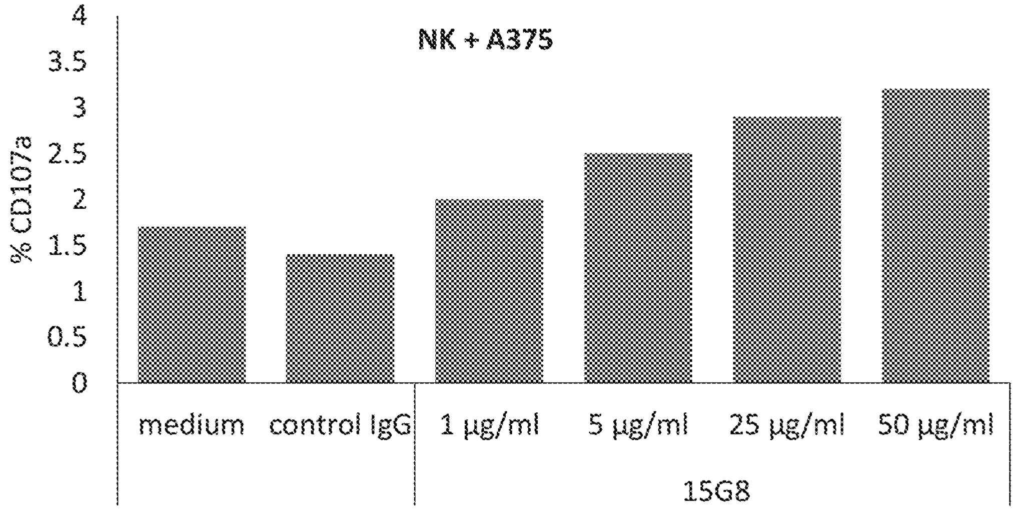
Figure 11G:
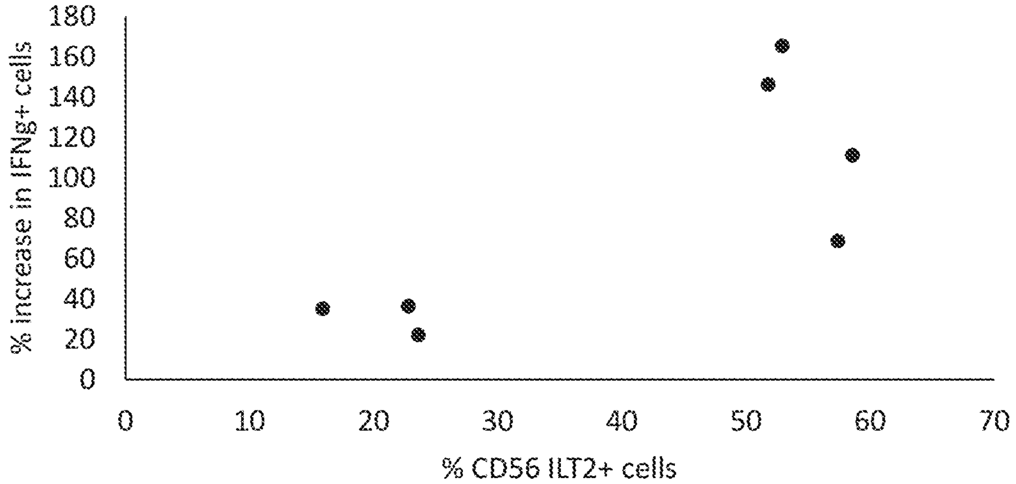
Figure 11H:
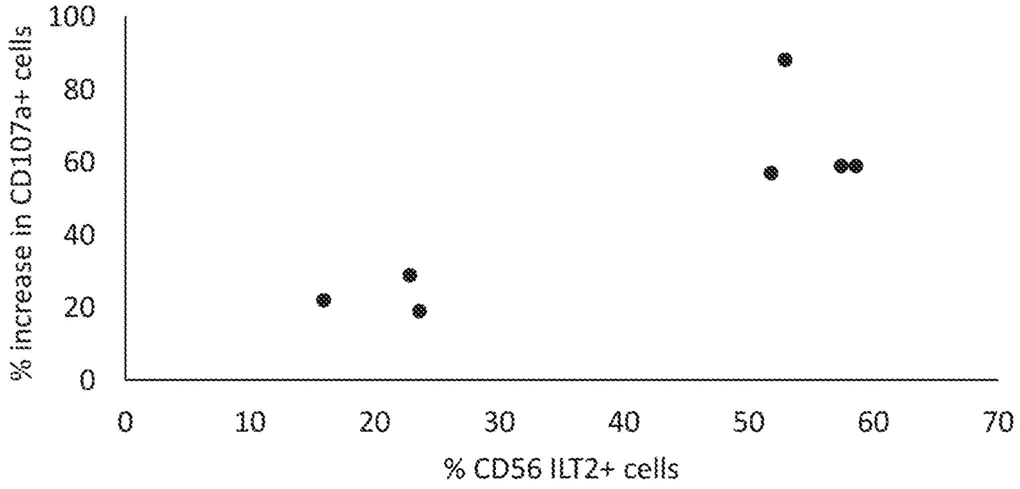

As demonstrated in FIG. 11A, the ILT2 antibodies of the invention could significantly enhance the cytotoxicity of NK cells against both HLA-G positive cells and various MHC-I-positive cancer cell lines (FIG. 11B) in a dose-dependent manner. Granzyme B (FIG. 11C) and interferon gamma (FIG. 11D) secretion was also measured and found to increase in a dose-dependent fashion. Primary NK cells were co-cultured with target HLA-G+ melanoma cells followed by analysis by FACS for expression of IFNγ, ILT2, CD56, and CD107A. The ILT2 positive, CD56 positive, NK cell population was specifically analyzed and the dose dependent increase in IFNγ expression and membranal CD107A expression was observed (FIG. 11E-11F). When each experiment was plotted separately, the correlation between % ILT2 positive cells and increased expression of IFNγ and CD107A was clearly apparent (FIG. 11G-H).

Example 7

ILT2 Antibodies Increase the Generation of Inflammatory Macrophages

Figure 12:
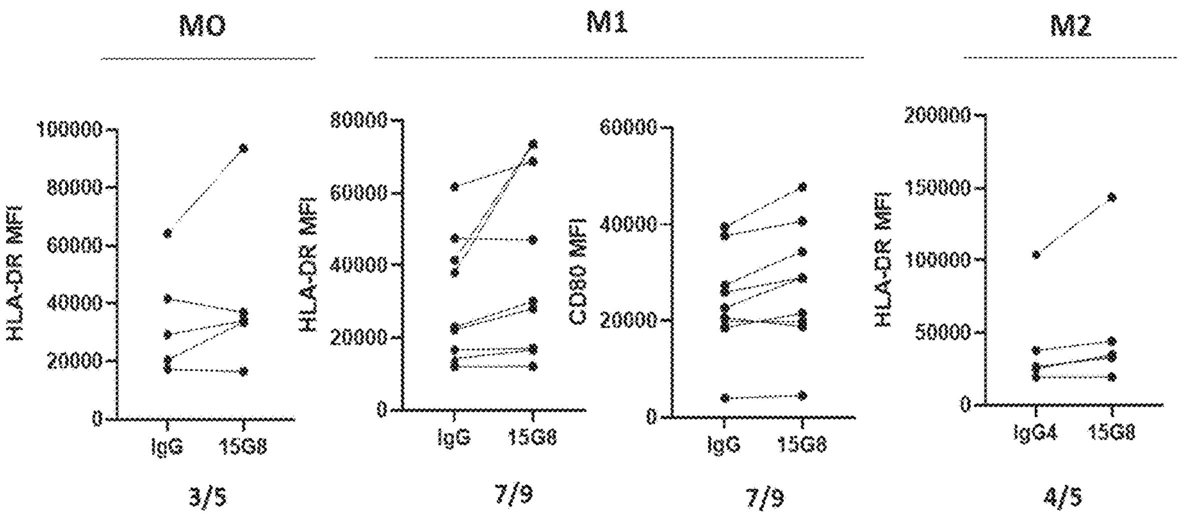
FIG. 12. Line graphs of HLA-DR and CD80 expression (MFI) as determined by flow cytometry in macrophages which were differentiated from monocytes isolated from healthy donors into M0, M1 or M2 macrophages in the presence of IgG or anti-ILT2 antibody. The number of patients which displayed increased expression of the specified marker in comparison to control IgG is indicated for each condition tested.

The effect of blocking ILT2 on the maturation of macrophages was examined in vitro. Monocytes isolated from healthy donors were differentiated in the presence of M-CSF (50 mg/mL) for 5 days to generate mature macrophages (M0) in the presence of a humanized blocking ILT2 antibody or control IgG. The macrophages were further differentiated in the presence of LPS (50 ng/mL) to generate M1 macrophages or with IL-4 (25 ng/mL) to generate M2 macrophages. As demonstrated in FIG. 12, the presence of ILT2 blocking antibodies during the maturation process of macrophages increased the expression of HLA-DR (a marker of M1 inflammatory macrophages) on the macrophages of most of the donors tested, whether they were differentiated into M0, M1 or M2 macrophages. In addition, macrophages differentiated into M1 macrophages also had increased CD80 levels in most of the donors tested. Taken together, these results demonstrate that the selected ILT2 antagonist antibodies can induce macrophages that display higher levels of HLA-DR and CD80, which represent macrophages with a more inflammatory M1 phenotype.

Example 8

Figure 13A:
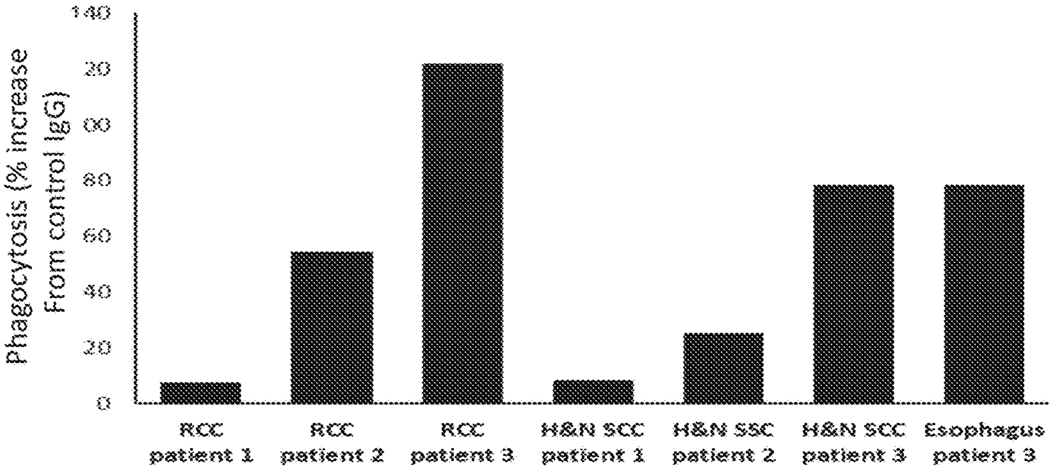
FIGS. 13A-13C. (13A) Bar graph of phagocytosis by macrophages co-cultured with various primary tumor cells. (13B-13C) Bar graphs of dose dependent phagocytosis of primary tumor cells isolated from a (13B) RCC patient and a (13C) H&N patient by autologous macrophages in the presence of a humanized antibody of the invention.
Figure 13B:
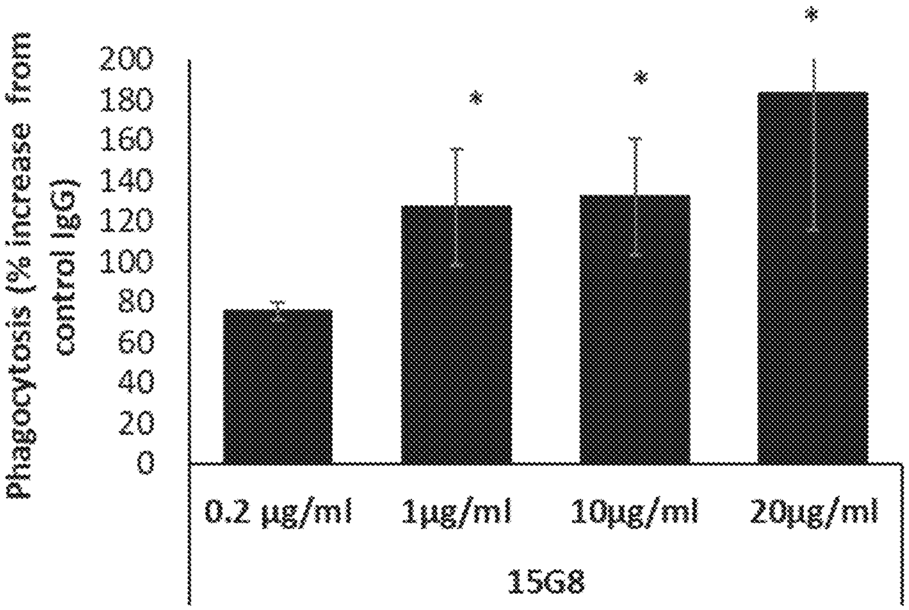

ILT2 Blocking Antibodies Enhance the Activity of Immune Cells Against Tumor Cells from Patients The activity of the generated anti-ILT2 antibodies was examined in ex vivo systems with tumor samples from cancer patients (RCC and H&N). In order to test the ability of the antibodies to increase phagocytosis of tumor cells from patients, macrophages generated from monocytes were incubated with tumor cells isolated from tumor samples. Phagocytosis levels were examined using the IncuCyte® real-time analysis system as detailed above. As demonstrated in FIG. 13A, ILT2 antibodies could enhance the phagocytosis of tumor cells from patients from different cancer indications. Further, the effect was dose dependent, and present even with autologous macrophages and was seen both for RCC (FIG. 13B) and squamous cell carcinoma from H&N (13C). In addition, the effect of ILT2 antibodies to enhance the activity of PBMCs was examined. Single cell suspensions of tumor samples from patients were incubated with PBMCs isolated from the same patients in the presence of IL-2 (activated PBMCs). As demonstrated in FIG. 14G, PBMC secretion of the pro-inflammatory TNF-a cytokine in the presence of the tumor cells was elevated in the presence of the ILT2 antibodies. Taken together, these results demonstrate the ability of blocking ILT2 antibodies to increase the activity of immune cells against tumor cells from various cancer indications.

Example 9

ILT2 Blocking Antibodies can be Combined with PD-1/PD-L1 Therapy

Figure 14A:
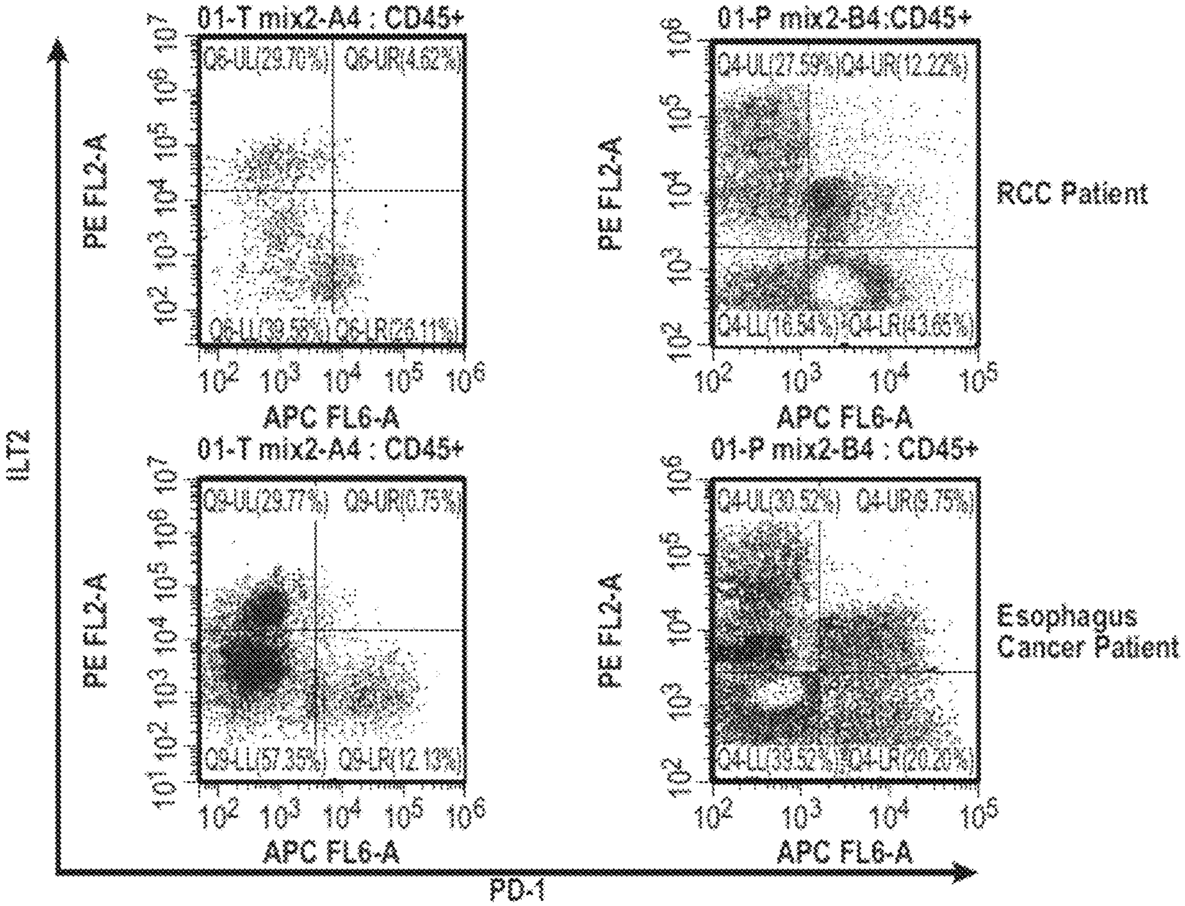
FIGS. 14A-14L. (14A) Dot plots of ILT2 and PD-1 expression in tumor cells (left panels) and PBMCs (right panels) from an RCC and esophageal cancer patient. (14B-14C) Box and whisker plots of (14B) PD-1 and (14C) 1LT2 RNA expression in CD8 T cell populations in the TME of CRC patients. (14D-14E) Dot plots of (14D) ILT2 expression in CD8 T cells from peripheral blood of healthy donors and of (14E) ILT2 and PD-1 expression in TILs from esophageal cancer. (14F) Scatter plot of the increase in membranal CD107a on PBMCs from 10 healthy donors activated with Staphylococcal Enterotoxin B (SEB) in the presence of 15G8, anti-PD-1 antibody or a combination of the two. (14G) Bar charts of CD107a increase in expression in exemplary PBMCs from 3 donors. (14H-14J) Bar charts of levels of inflammatory cytokine (14H) IFNγ, (14I) TNFα, (14J) GM-CSF secretion from activated PBMCs cocultured with various primary cancer cells in the presence of anti-PD-1 antibody, humanized anti-ILT2 antibody or both. (14K-14L). Bar charts of levels of IFNγ secretion from T cells cocultured with (14K) dendritic cells or (14L) macrophages in a mixed lymphocyte reaction.
Figure 14B:
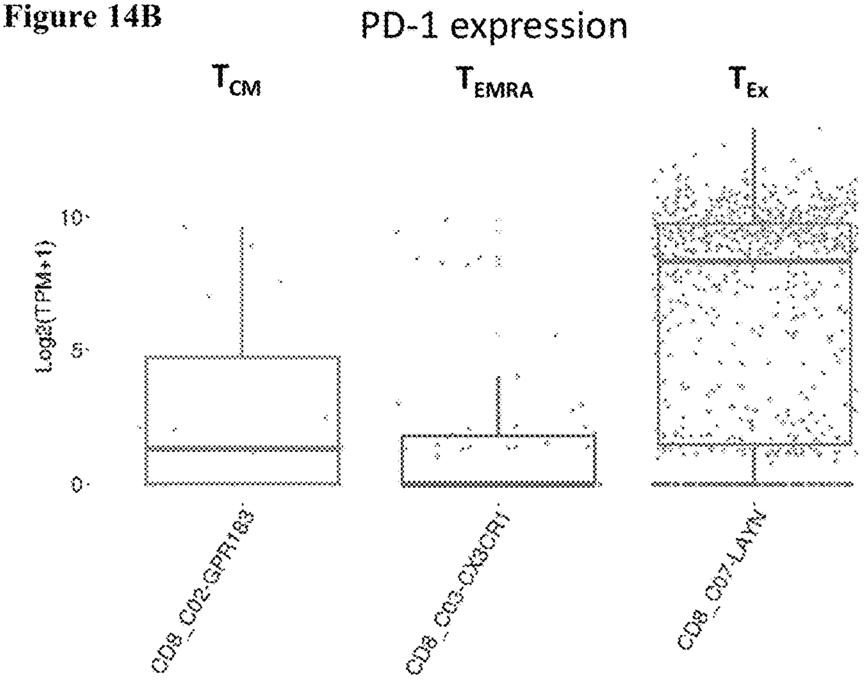
Figure 14C:
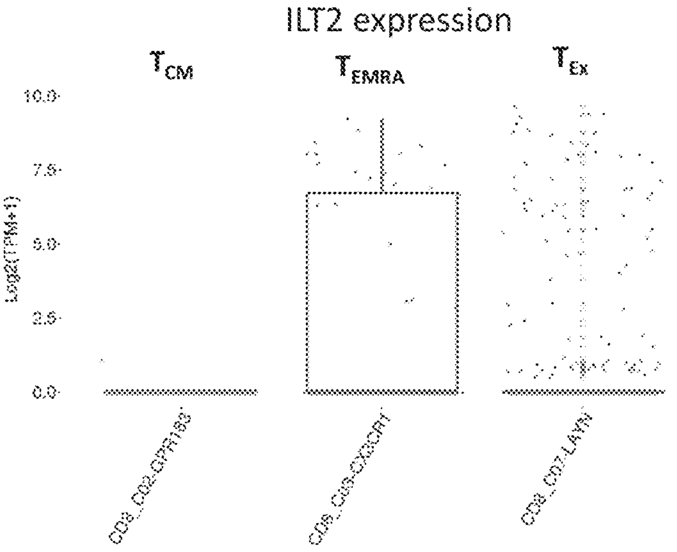
Figure 14D:
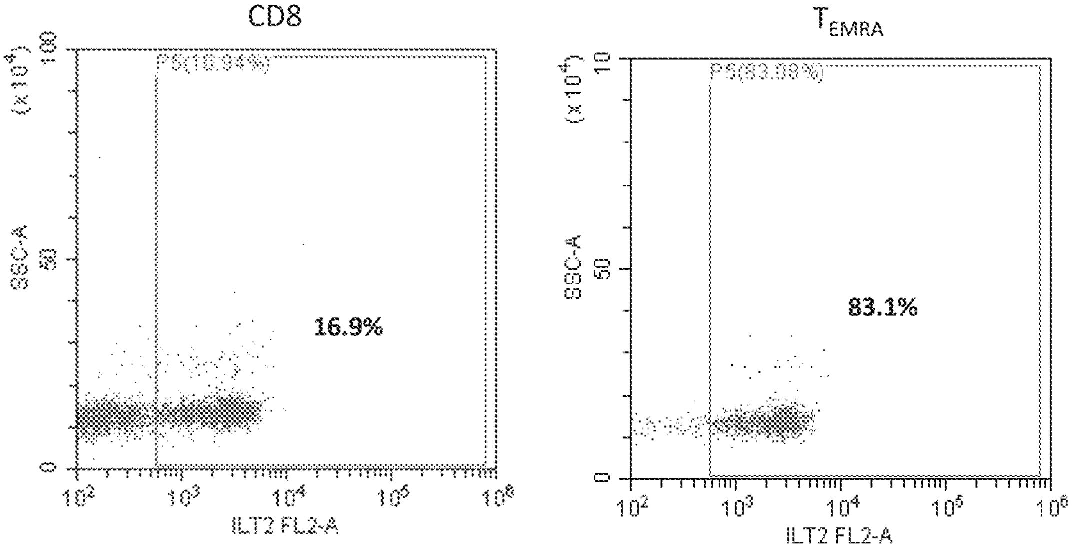
Figure 14E:
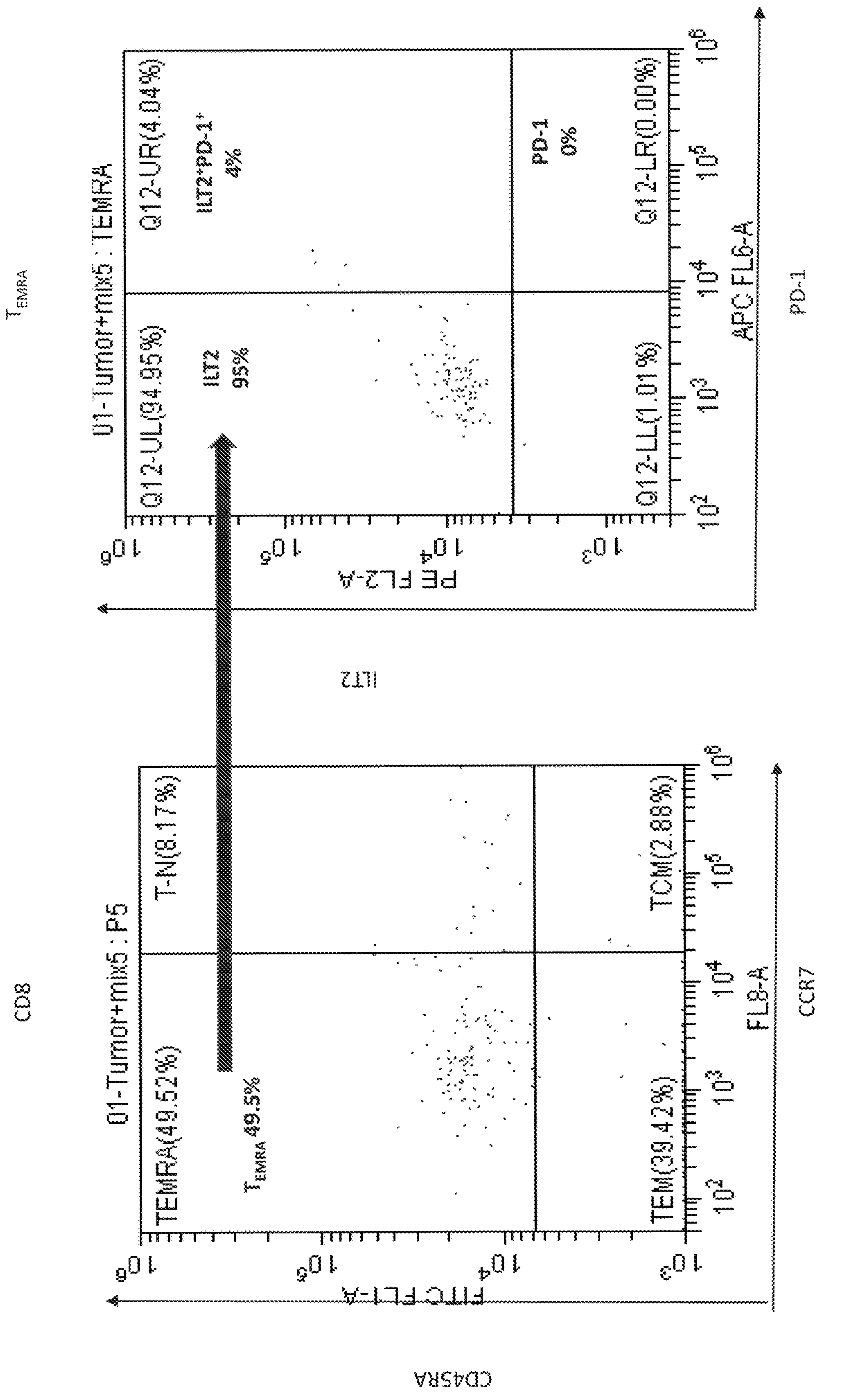

ILT2 and PD-1 are, for the most part, expressed on different immune cells that comprise both the peripheral blood cells and the tumor microenvironment resident immune cells (FIG. 14A). Analysis of ILT2 and PD-1 expression in intra-tumoral CD8 positive T cells from CRC patients found that T central memory cells (Tcm) and exhausted T cells (Tex) both expressed high levels of PD-1 (FIG. 14B), but low levels of ILT2 (FIG. 14C). CD45RA re-expressing T cells ($T_{EMRA}$) showed the exact opposite pattern, expressing high levels of ILT2 and low levels of PD-1. This dichotomy was not a cancer specific phenomenon, a large percentage (83%) of $T_{EMRA}$ cells from the blood of healthy donors were found to be ILT2 positive while only a small percentage (17%) of total CD8 positive T cells were positive (FIG. 14D). Nevertheless. ILT2 expression was enhanced in T cells in the TME. A single cell suspension was generated by enzymatic digestion of a tumor isolated from an esophageal cancer patient. FACS analysis showed that a large proportion of CD8 positive tumor infiltrating lymphocytes (TILs) were $T_{EMRA}$ cells (50%) and that these $T_{EMRA}$ cells were 100% ILT2 positive, but almost completely PD-1 negative (95%) (FIG. 14E).

Figure 14G:
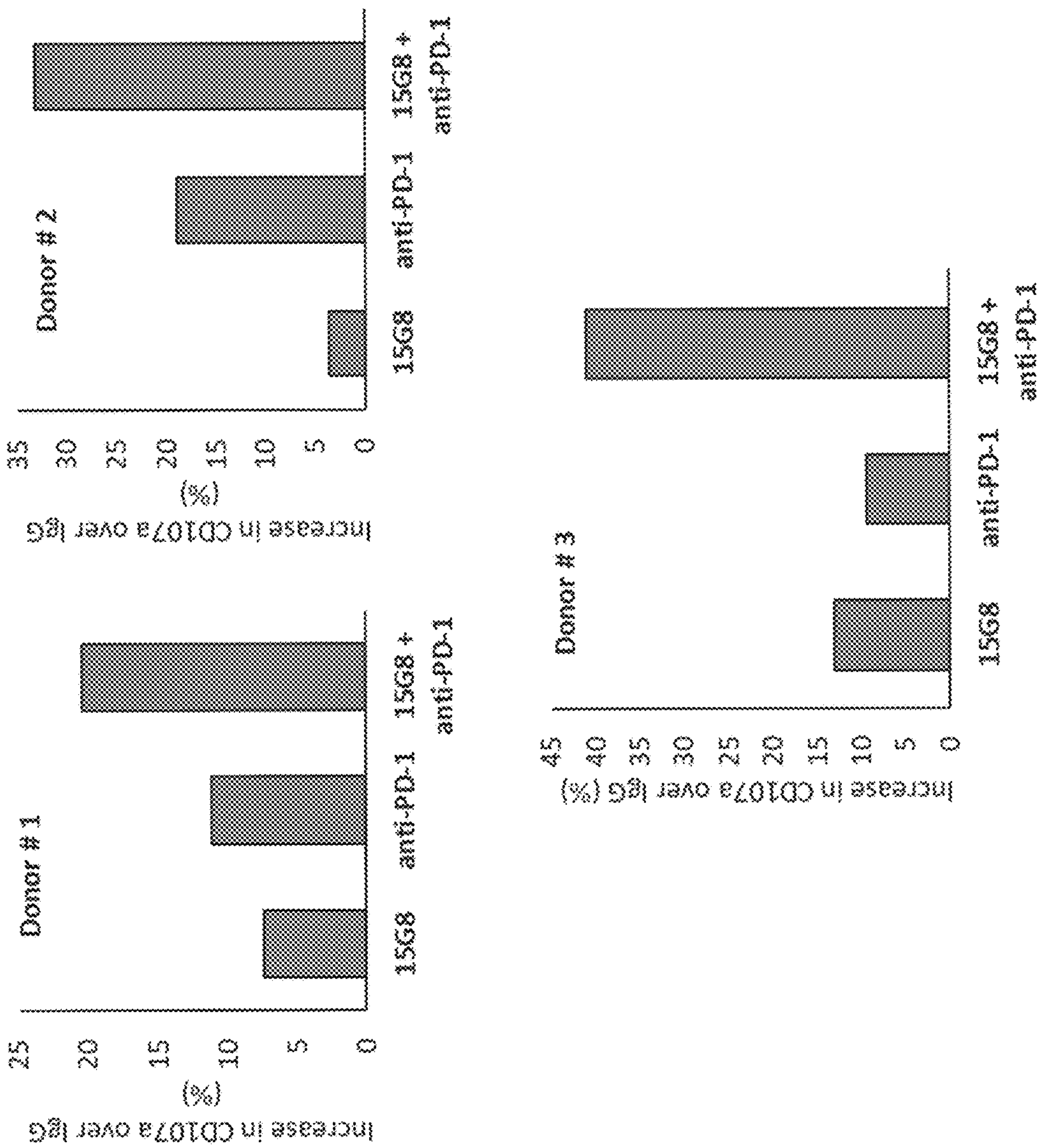
Figure 14F:
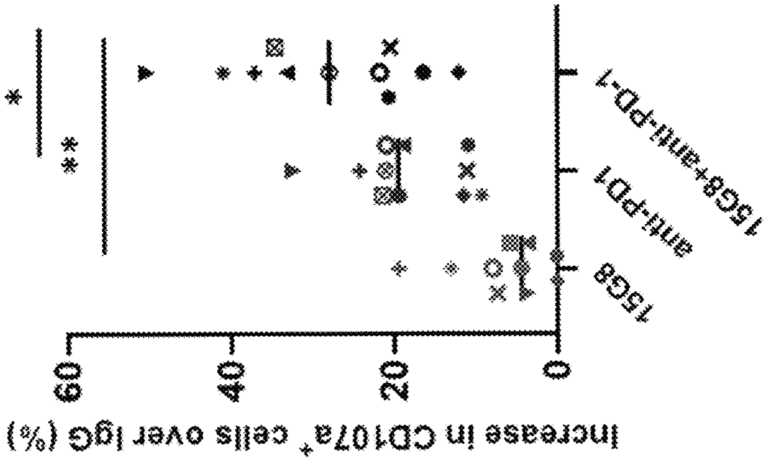

The effect of the combination of an anti-ILT2 antibody of the invention and anti-PD-1 was tested in SEB-activated (10 ng/ml) PBMCs from 10 healthy donors. Expression of membranal CD107a was used as a marker for increased cytotoxicity. Overall, the 15G8 antibody produced on average a small increase in surface CD107a, while anti-PD-1 produced a somewhat larger response which was donor-dependent (FIG. 14F). The combination of the two antibodies produced increased CD107a levels on average; however, these changes were variable based on the specific donor sample. FIG. 14G presents three exemplary samples. The first donor saw an additive effect when anti-PD-1 was combined with 15G8, with the total CD107a level being approximately equal to the sum of the effects of each antibody alone. The second donor had a stronger response to anti-PD-1 than to anti-ILT2, but unexpectedly the combination of the two antibodies had a more than additive effect. Anti-PD-1 produced 19% increase in expression, anti-ILT2 produced 3.7% increase, but the combined treatment resulted in 33.2% increase. This synergistic effect was even more pronounced in the cells of donor #3. In donor #3 15G8 was more effective than anti-PD-1 (13.1% increase vs. 9.3% increase) and the combined therapy was vastly more effective (41%) producing almost twice the effect of what would be predicted from a merely additive combination.

Figure 14H:
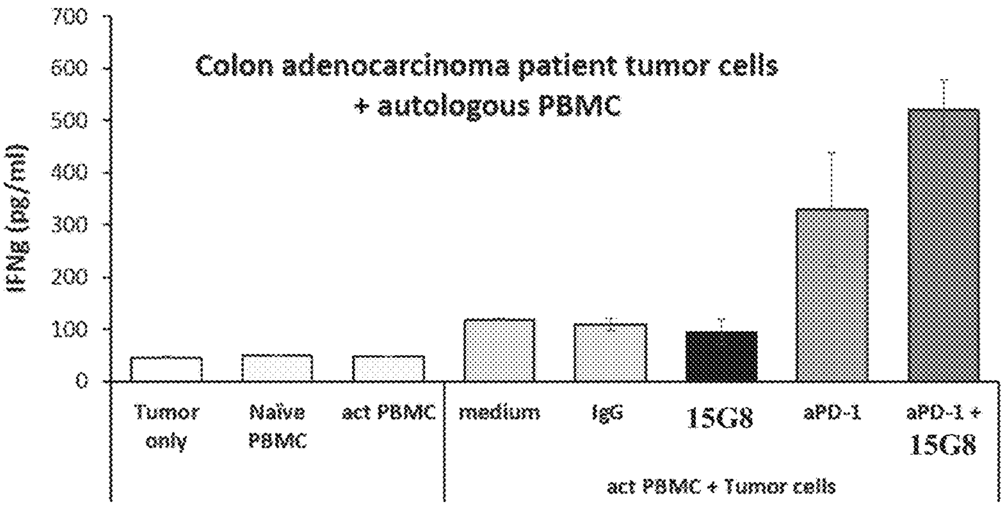
Figure 14I:
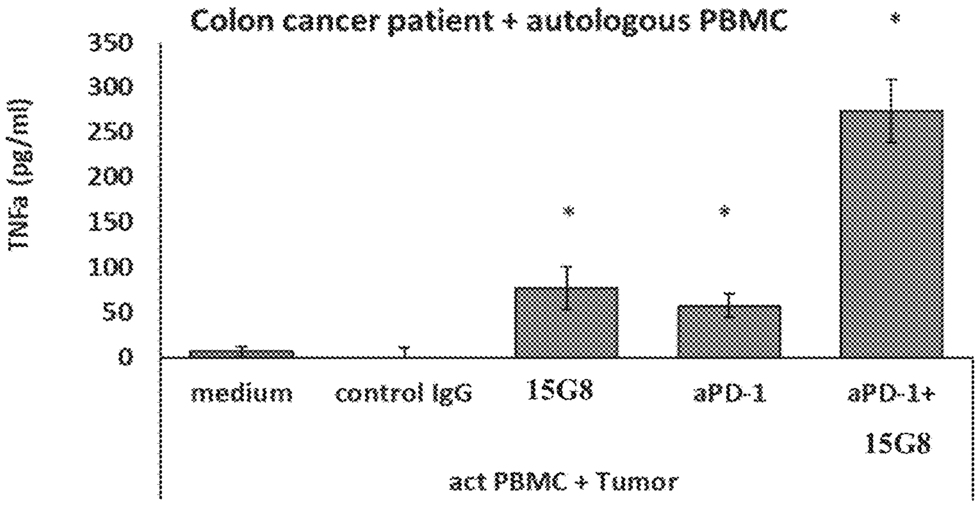
Figure 14J:
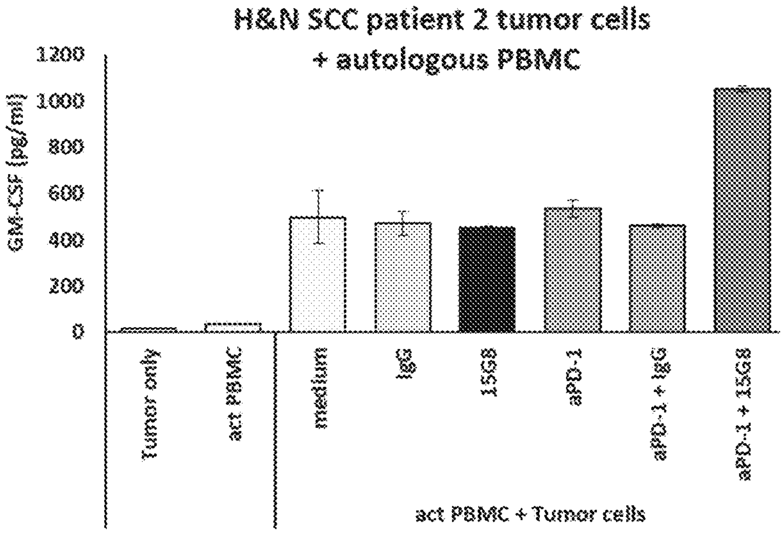

A combination treatment of patient tumor cells with PD-1 blocking antibody and the generated ILT2 antibodies was assessed next. Various patient cancer cells were incubated with autologous PBMCs in the presence of anti-PD1 antibody, antibodies of the invention and combinations thereof. IgG was used as a control and secretion of pro-inflammatory molecules was measured as a readout. An enhanced secretion of pro-inflammatory cytokines was observed in the combination treatments (FIG. 14H-14J). Treatment of colon adenocarcinoma cells from a first patient by humanized antibody 15G8 did not enhance IFNγ secretion at all as compared to IgG control, while anti-PD-1 produced a robust increase in cytokine secretion (FIG. 14H). Unexpectedly however, the combination of anti-PD-1 with the ILT2 antibody increased secretion by more than 50%. A second patient showed a similar trend with small increases induced by ILT2 antibody or anti-PD-1 and with an enhanced synergistic increase present when the two antibodies were used in combination (FIG. 14I). GM-CSF expression was not altered by either antibody alone as compared to control, however, surprisingly, the combination of the two antibodies produced a robust increase of nearly 100% of the control GM-CSF levels (FIG. 14J).

Figure 14K:
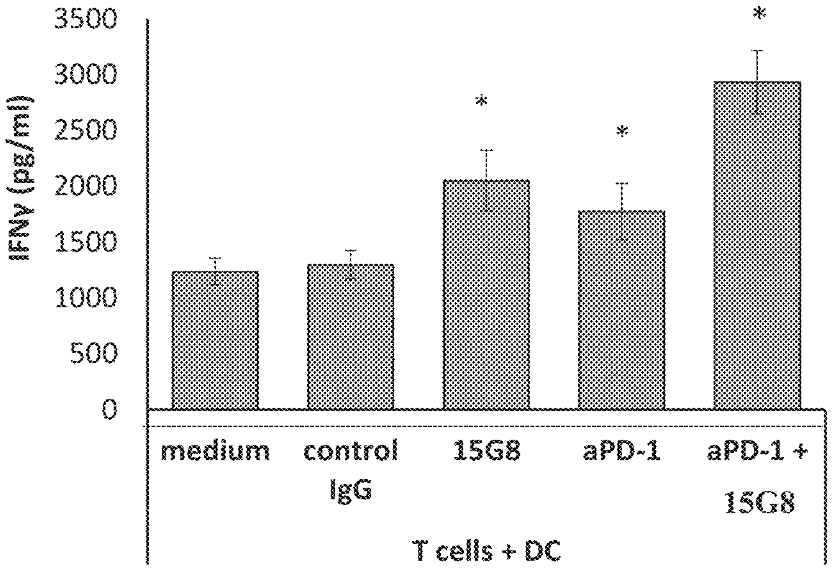
Figure 14L:
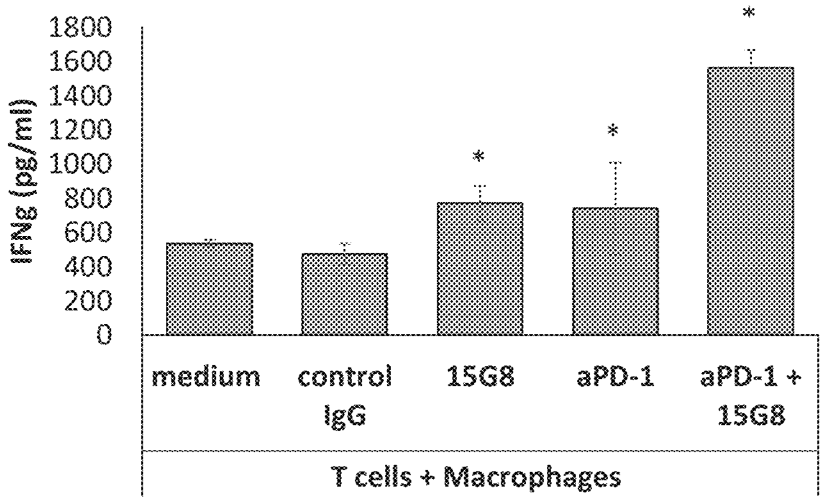

Next a mixed lymphocyte reaction was used to assess combined therapy. Dendritic cells and CD8 positive T cells were isolated from different healthy donors and macrophages were generated from monocytes isolated from a H&N cancer patient. The cells were combined in an effector cell to target ratio of 5:1, with the indicated treatments (20 μg/mg of each). IFNγ secretion by the T cells was enhanced when either anti-ILT2 antibodies or anti-PD-1 antibodies were present and this effect was increased with the use of both antibodies in combination (FIG. 14K-14L). A greater cumulative effect was observed in the macrophage culture (FIG. 14L) as compared to the dendritic cell culture (FIG. 14K). These results clearly show that anti-ILT2 and anti-PD-1 therapy have a synergistic and de novo effect on enhancing immune cell inflammatory response.

Example 10

ILT2 Blocking Antibodies Reduce Tumor Burden In Vivo

Figure 15A:
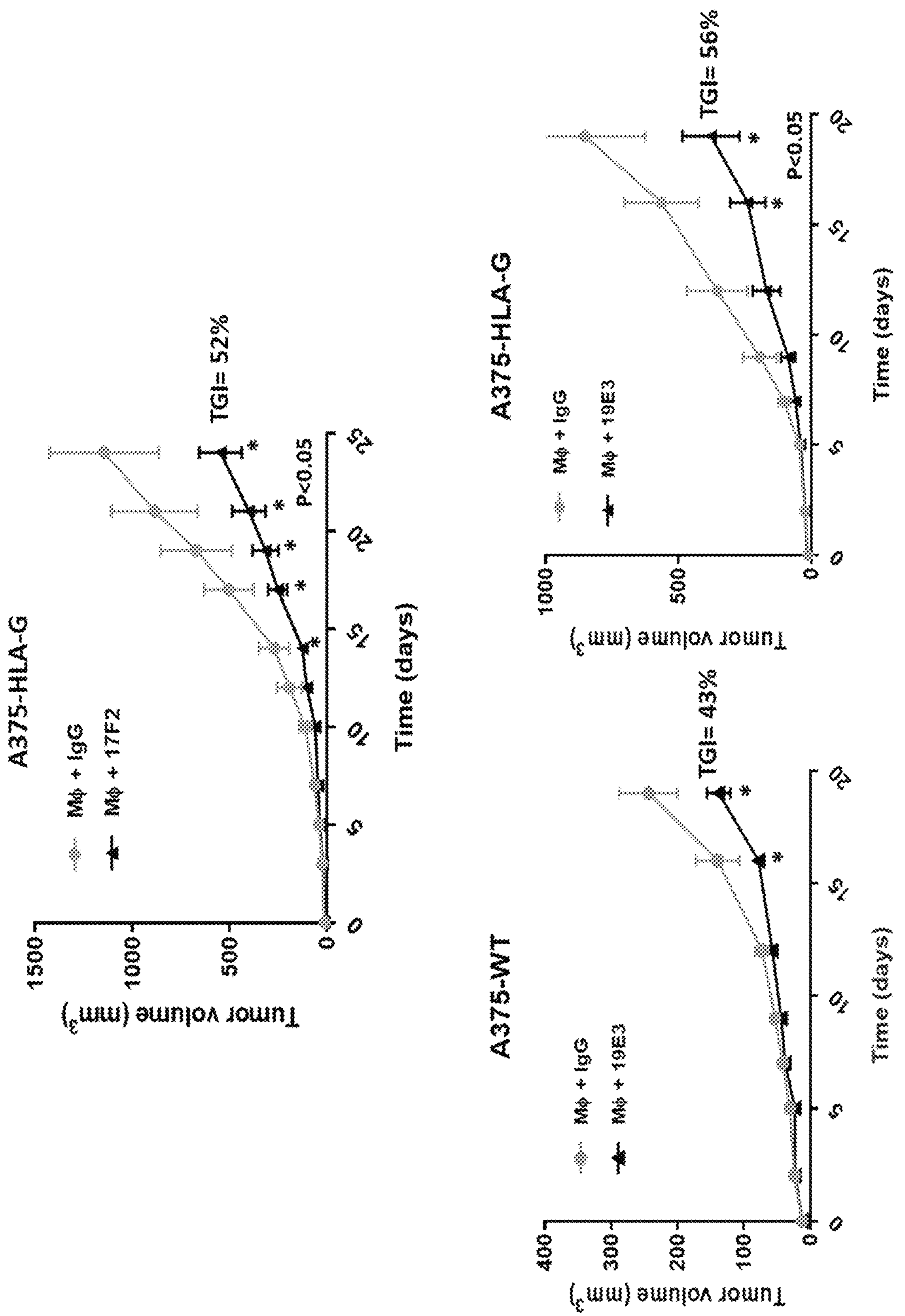
FIGS. 15A-15F. (15A) Line graphs of tumor volume of HLA-G and MHC-I expressing tumors grown in immunocompromised mice supplemented with human macrophages and anti-ILT2 antibodies. (15B). Illustration of mice treatment schedule for preventing lung tumors. (15C) Photographs of lungs from immunocompromised mice inoculated with HLA-G positive cancer cells with or without human PBMC and an ILT2 antibody. (15D) Scatter plot summarizing the data from 15C. (15E) Illustration of mice treatment schedule for treating already established lung tumors. (15F) Box and whisker plot of tumor weights.
Figure 15A:
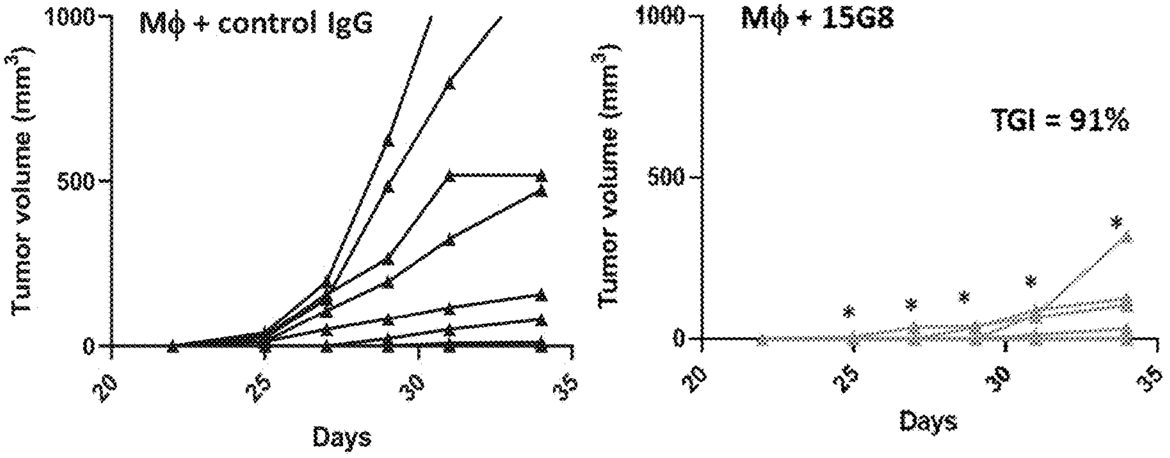

The efficacy of the anti-ILT2 antibodies was examined in a xenograft in vivo model. Immune compromised SCID-NOD or NSG mice were inoculated with cancer cell lines (A375-HLA-G, A375-WT, COLO-320-HLA-G) and human macrophages generated from the blood of healthy donors were injected into the mice in the presence of ILT2 antibodies. As demonstrated in FIG. 15A, the administration of the generated ILT2 antibodies led to significant tumor inhibition in this model which was most likely mediated by the activity of the human macrophages in this system. In addition, anti-tumor efficacy was observed in HLA-G-positive as well as MHC-I-positive tumor cells.

Figure 15B:
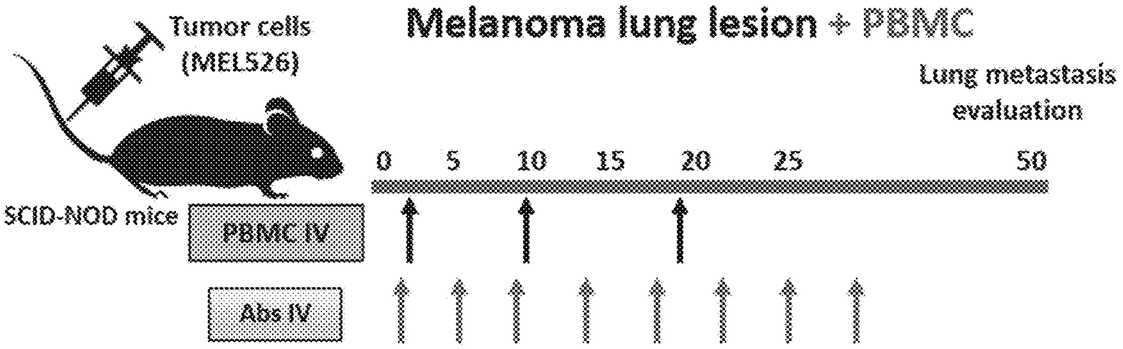
Figure 15C:
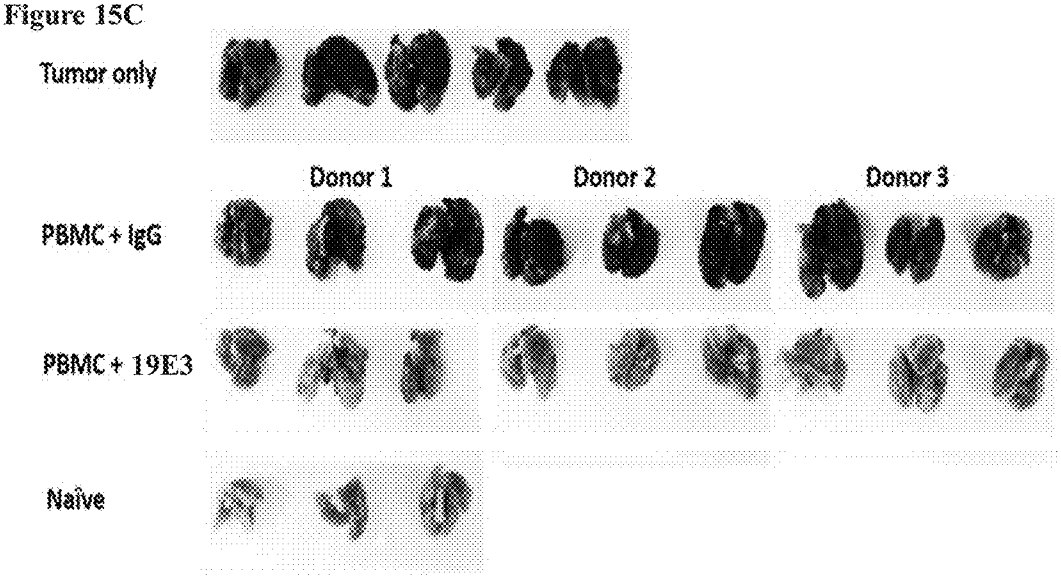
Figure 15D:
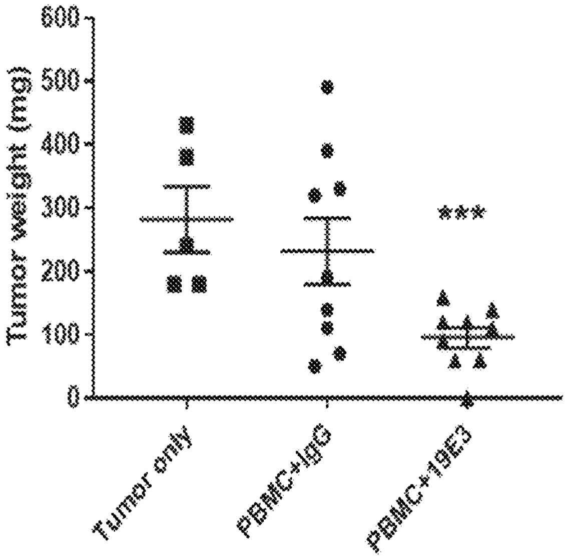

The efficacy of the anti-ILT2 antibodies was also examined in a lung lesion melanoma xenograft in vivo model. Immune compromised SCID-NOD mice were inoculated with melanoma cells (MEL526-HLA-G). Human PBMC, isolated from the blood of healthy donors, were injected into the mice in the presence of select ILT2 antibodies starting one day after the inoculations and repeated at days 2, 10, 18 (FIG. 15B). ILT2 antibodies were administered at days 1, 4, 8, 11, 15, 18, 22 and 25. As demonstrated in FIG. 15C, the administration of the generated ILT2 antibody led to a significant reduction in the metastasis of the tumor cells, which is represented by the formation of black lesions in the lungs of the mice. The lungs of the mice that were treated with the ILT2 antibody have very few such lesions compared to the mice that were treated with the control IgG. This effect is also demonstrated by the reduction of the weight of the lungs in these mice (FIG. 15D) and was most likely mediated by the human lymphocytes that were administered to the mice in combination with the inhibition of ILT2 by the administered antibody. Thus, the anti-ILT2 antibodies were effective at preventing metastasis and tumor formation.

Figure 15E:
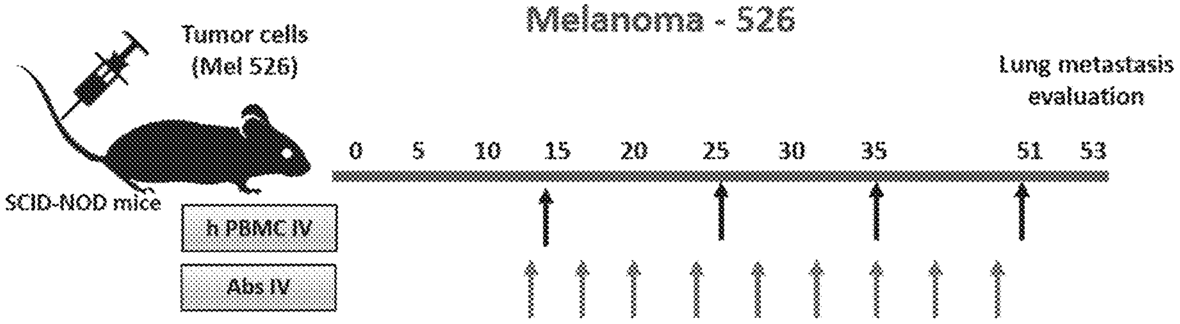
Figure 15F:
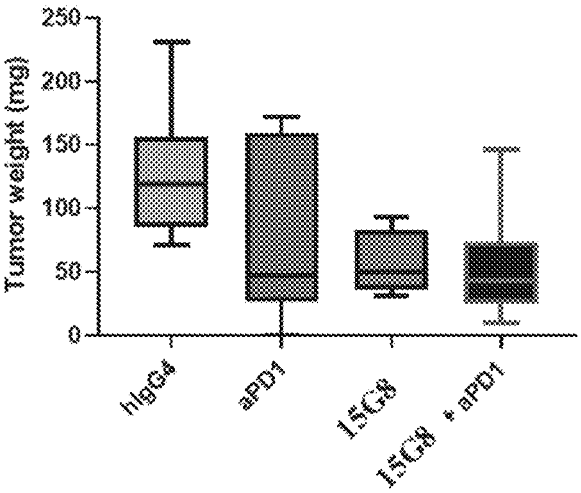

Next, the effectiveness of the new antibodies in treating an already formed tumor was tested in the same in vivo mouse model. SCID-NOD mice were engrafted by IV administration with MEL526-HLA-G cells as before. After 15 days, human PBMCs isolated from healthy donors were administered to the relevant groups of mice and this administration was repeated at days 25, 35 and 51 (see FIG. 15E). Antibodies, (ILT2 antibodies, anti-PD-1 antibodies or a combination of the two) were administered at days 14, 17, 20, 24, 27, 30, 34, 37 and 50 (see FIG. 15E). At day 53 the mice were sacrificed, and the lungs weighed. Tumor weight was calculated by subtracting naïve mice lung weight from the lung weight of the test mice. Anti-PD-1 antibody decreased tumor weight, though not significantly, while the ILT2 antibody and the combination treatment had a significant effect (FIG. 15F).

Figure 16A:
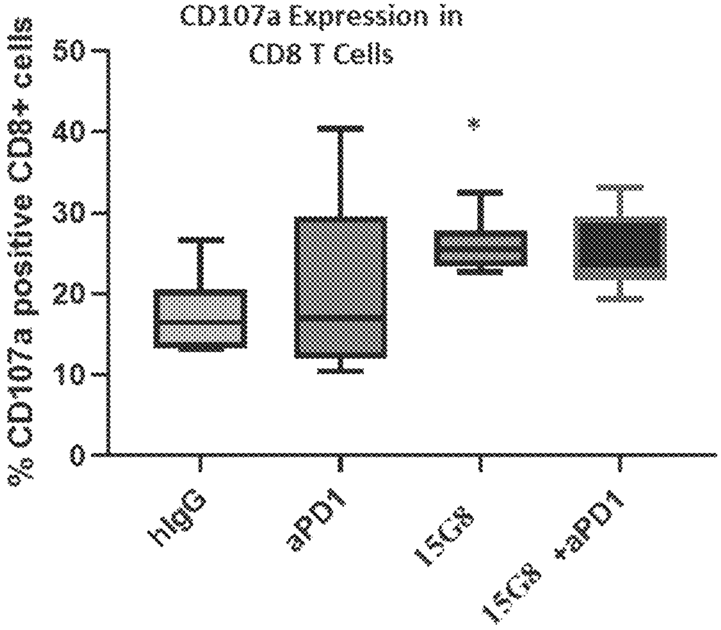
FIGS. 16A-16F. (16A-16F) Box and whisker plots of (16A) CD107A expression in total CD8 T cells, (16B) CD107A expression in $T_{EMRA}$ cells. (16C) CD69 expression in NK cells, (16D) CD69 expression in total CD8 T cells, (16E) CD107 expression in $T_{EMRA}$ cells and (16F) CD69 expression in combination treated NK cells in mice that received PBMC from donors with low or high levels of ILT2 in their $T_{EMRA}$ cells or NK cells, respectively. * is a $P<0.005$.  is a $P<0.0005$. * is a $P<0.0001$.
Figure 16B:
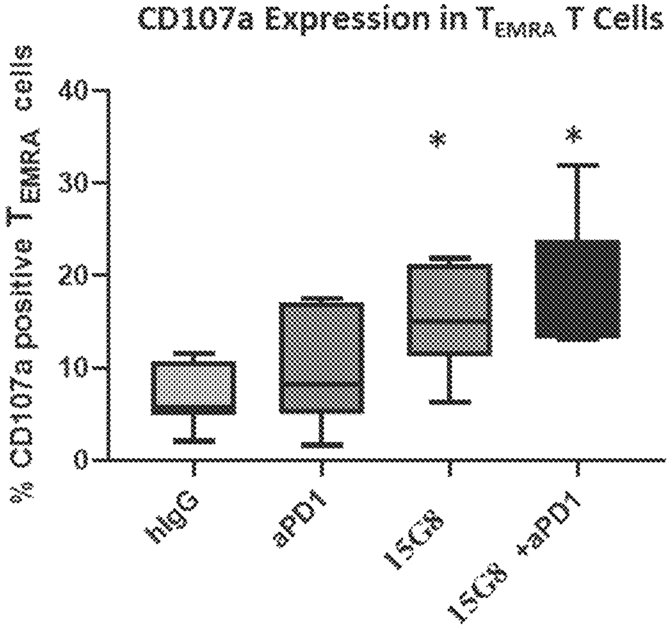
Figure 16C:
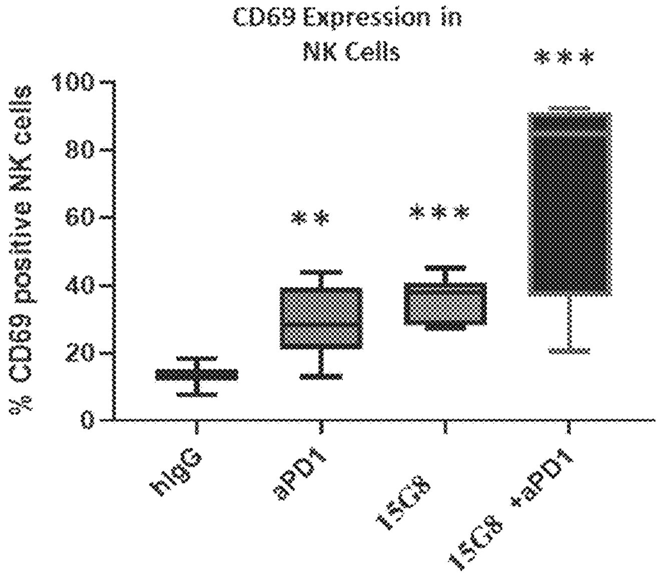
Figure 16D:
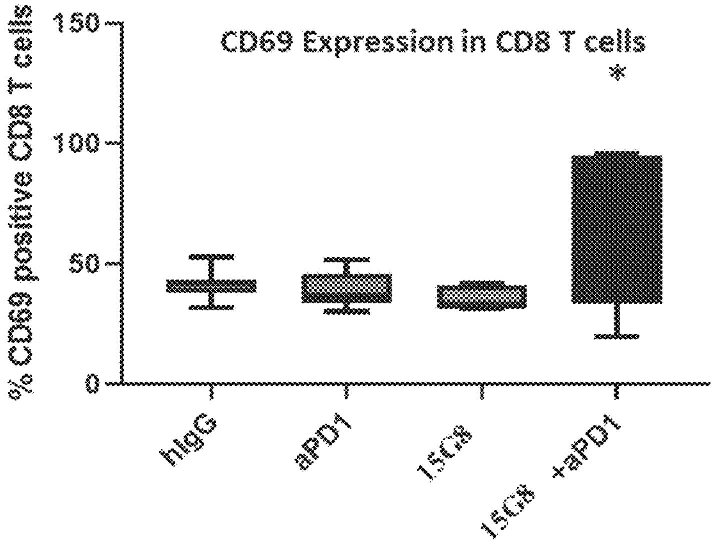
Figure 16E:
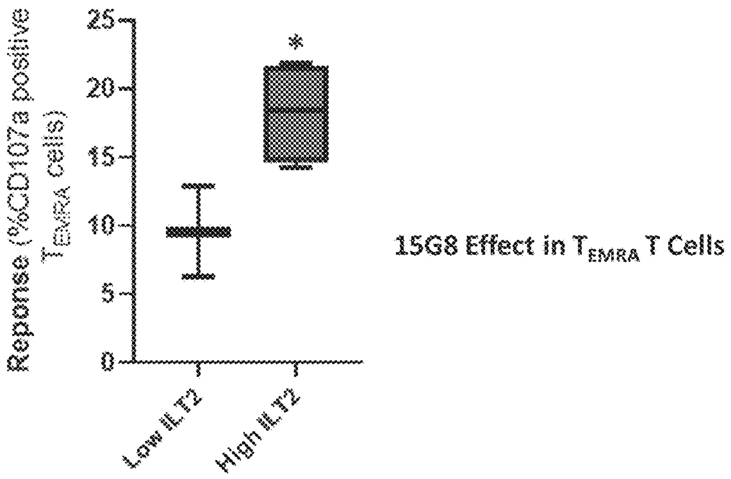
Figure 16F:
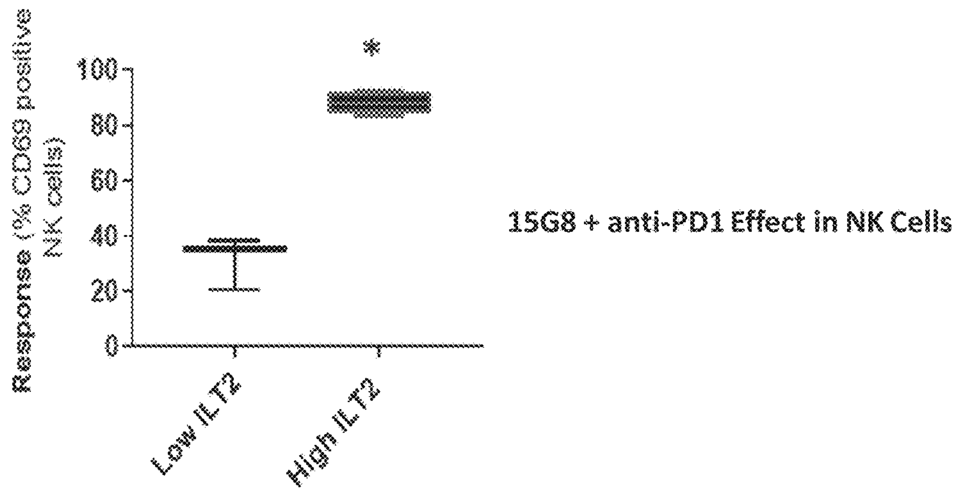

Tumor derived CD8 T cells, $T_{EMRA}$ cells and NK cells were tested for CD107A and CD69 expression. In total CD8 T cells, anti-PD-1 antibody induced a non-significant increase in CD107A expression, w % bile the ILT2 antibody, but not the combination therapy, induced a significant change (FIG. 16A). In $T_{EMRA}$ cells, both the ILT2 antibody and the combination therapy induced a significant increase (FIG. 16B). In NK cells, both anti-PD1 and anti-ILT2 antibodies significantly increased the percentage of CD69 positive cells, but surprisingly the combined therapy had a greatly enhanced effect with the total percentage of CD69 positive cells being more than the combination of either therapy alone (FIG. 16C). Surprisingly, when CD69 expression was examined in CD8 T cells neither anti-PD1 nor anti-ILT2 increase expression, however, the combined treatment induced a highly significant increase in CD69 expression (FIG. 16D). Further, it was determined that the effect of the ILT2 antibody was correlated with ILT2 expression. When the experiments were broken down into mice that received PBMCs with low or high ILT2 expression a significant difference in activation markers was observed. In $T_{EMRA}$ cells the high ILT2 expressing PBMCs included more than doubling of CD107A expression as compared to the low ILT2 expressing PBMCs (FIG. 16E). Similarly, when NK cells were examined, the high ILT2 expressing PBMCs induced nearly 900% of cells to express CD69 when the combination treatment was administered; while the low ILT2 expressing PBMCs induced less than 40% of NK cells to express CD69 (FIG. 16F). Thus, the expression level of ILT2 in the PBMCs is essential for the most potent effects of the antibodies.

Example 11

In Vivo Humanized H&N Model

Figure 17A:
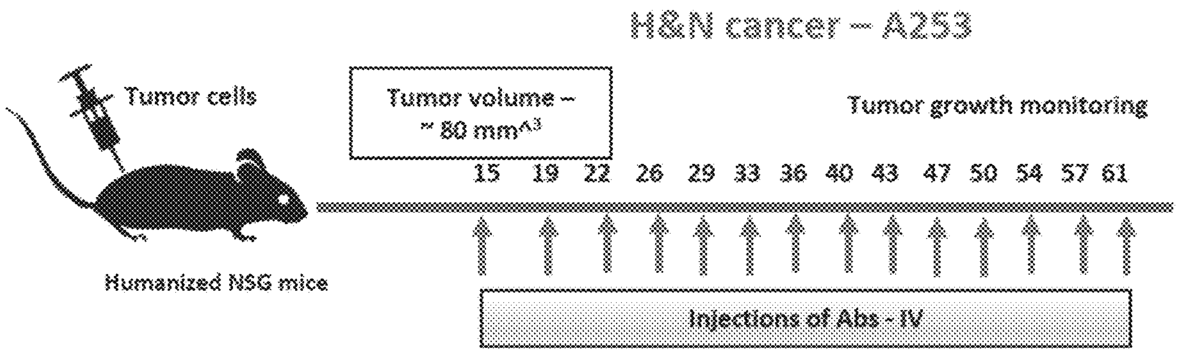
FIGS. 17A-17F. (17A) Illustration of mice treatment schedule of humanized NSG mice inoculated with H&N cancer and treated with anti-ILT2 or control antibodies. (17B) Line graph of tumor weight from IgG and anti-ILT2 treated mice. (17C-17E) Bar graphs of (17C) baseline ILT2 levels in peripheral CD8 T cells in mice that responded (R) or did not respond (NR) to BND-22 treatment. Intra-tumoral post-treatment (17D) CD107A expression, (17E) M1/M2 ratio and (17F) total CD80 positive dendritic cell number in the four mice treated with anti-ILT2 antibody.
Figure 17B:
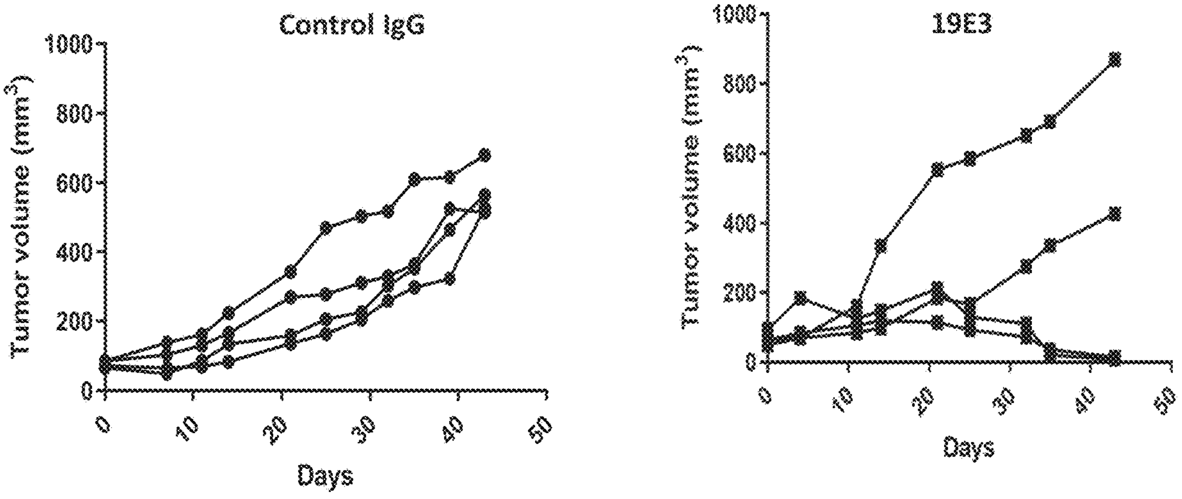
Figure 17C:
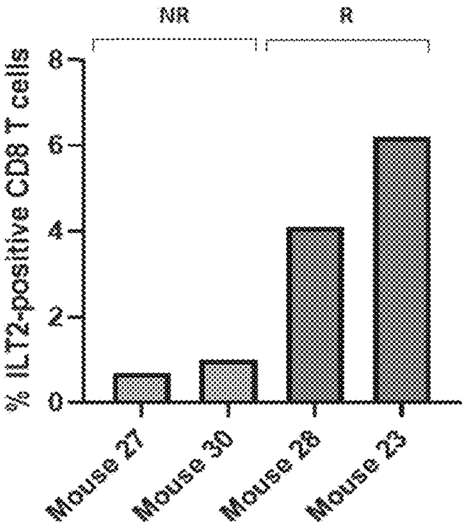
Figure 17D:
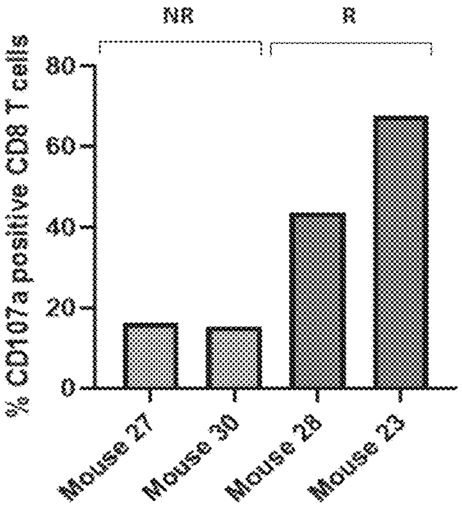
Figure 17E:
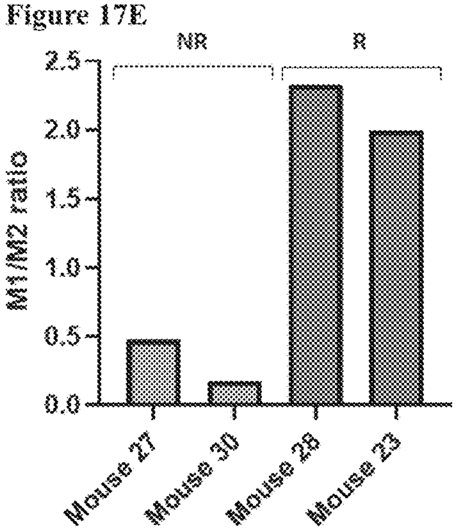
Figure 17F:
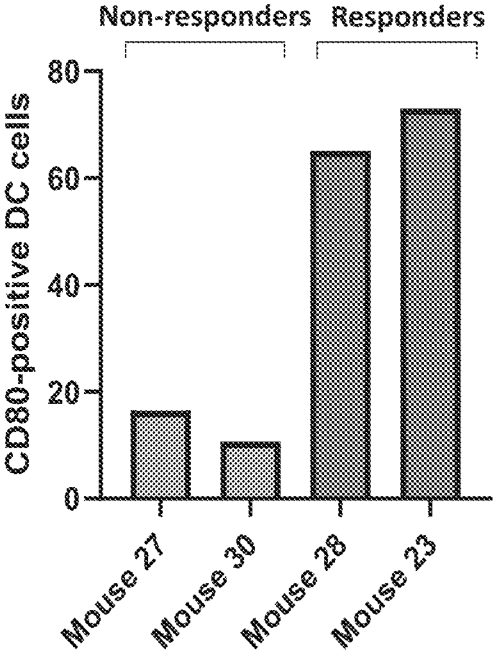

In a second in vivo model, humanized mice (human CD34+ engrafted mice) were inoculated with A253-HLA-G cells. When tumors reached a size of 80 cubic millimeters mice were treated with control IgG or ILT2 antibody (15G8, 10 mg/kg for both). The treatment was repeated twice a week (FIG. 17A) until day 43 and the tumors were measured by a caliper at various time points to determine tumor size. The ILT2 antibodies completely retarded tumor growth in 2 of the 4 of the mice (mice #23 and 28), with the tumor being eradicated by day 43 (FIG. 17B). In order to determine if the different responses to the treatment were due to different levels of expression of ILT2 in the immune cells of the mice, CD8 T cells from peripheral blood were assayed for ILT2 expression at baseline. Indeed, both mice that had a complete response had T cells with high expression of ILT2, the other two mice had significantly lower expression levels (FIG. 17C). Further, by examining the TME post treatment, three other pharmacodynamic markers of response which differentiate responders from non-responders, CD107A expression in T cells (FIG. 17D), M1/M2 macrophage ratio (FIG. 17E), and total CD80 positive dendritic cells (FIG. 17F) were demonstrated. These results point to the fact that anti-ILT2 generates a shift in the myeloid and lymphoid compartments of the tumor microenvironment and can also increase the capability of dendritic cells to present antigens and recruit more T cells to the tumor.

Example 12

Epitope Mapping of the 15G8 Humanized Antibody

The 15G8 antibody was sent for epitope mapping to determine the location on ILT2 to which it binds. Mapping was performed by the MAbSilico company. The structure of ILT2 used was modelled using the structures: 6AEE (four Ig-like domains, some loops missing), 1VDG (unpublished, domains 1 and 2), 1G0X (domains 1 and 2) and 4LL9 (domains 3 and 4). The 6AEE and 1G0X structures were taken from Wang. Q., et al., (2019). "Structures of the four Ig-like domain LILRB2 and the four-domain LILRB1 and HLA-G1 complex." *Cell. Mol. Immunol.*, and the 4LL9 structure was taken from Chapman, T. L., et al., (2000). "Crystal structure and ligand binding properties of the D1D2 region of the inhibitory receptor LIR-1 (ILT2)". Immunity. 13(5), 727-736. Region D1 was defined as residues 24-121 of ILT2. Region D2 was defined as residues 122-222 of ILT2. Region D3 was defined as residues 223-321 of ILT2. Region D4 was defined as residues 322-409 of ILT2. 3D model of the antibody was built using Modeller.

Figure 18B:
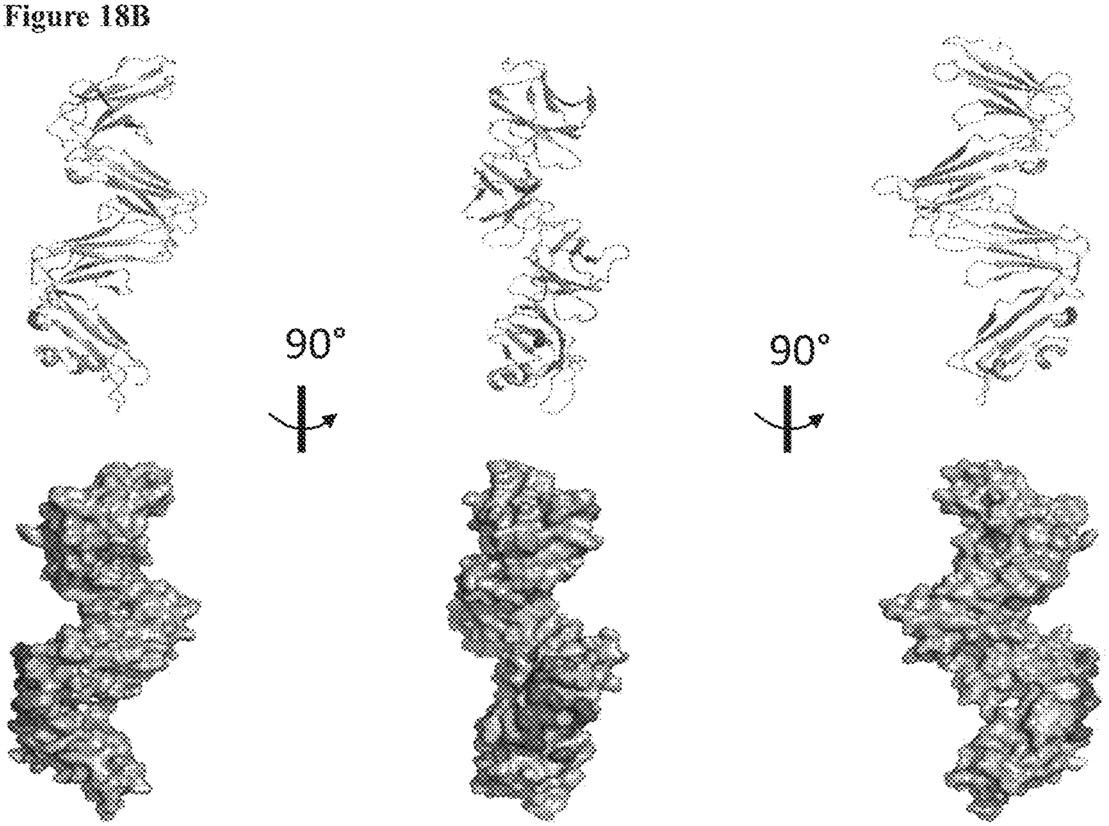
Figure 18C:
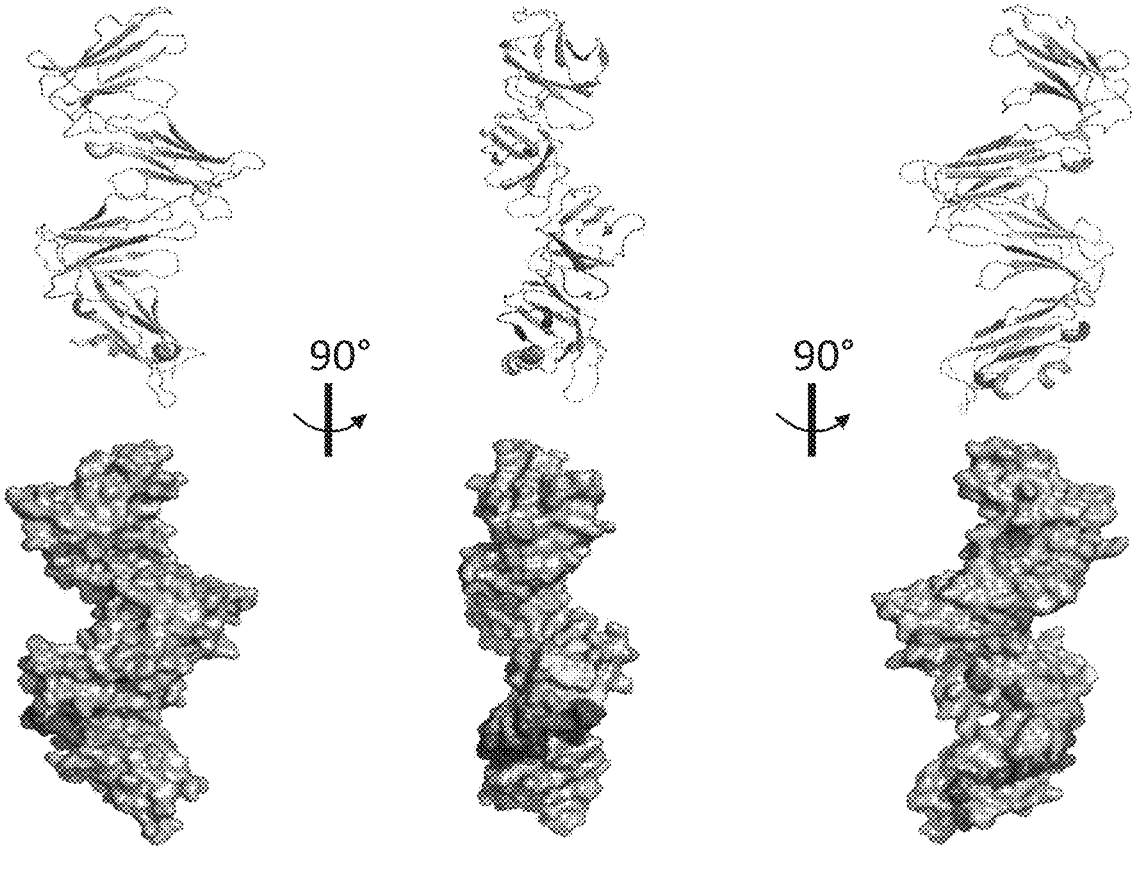

Based on the top 30 ranking docking poses, the residues of the target were scored for their probability to belong to the epitope. The residues that probably belong to the epitope are shown on the sequence in FIG. 18A and on the structure of the target in FIG. 18B. From these residues, four main interaction regions are defined on the target (FIG. 18C). All four of these interaction regions are found in the interdomain section of ILT2, that is the hinge section between D1 and D2. Validation mutations were chosen within these regions and are summarized in Table 3. These mutations are generated within full-length ILT2 or a truncated D1+D2 protein and binding of the 15G8 antibody is tested. Loss of or decreased binding to a mutant indicates that the region is an authentic epitope of the 15G8 antibody.

TABLE 3

| Test mutations | |
|---|---|
| Name | Mutations |
| 15G8_region 1 | K56A Q58A S63A E67A |
| 15G8_region 2 | D177A N179A E183A |
| 15G8_region 3 | Y98A I99A K100A T102A |
| 15G8_region 4 | Q124A V125A |

Figure 18D:
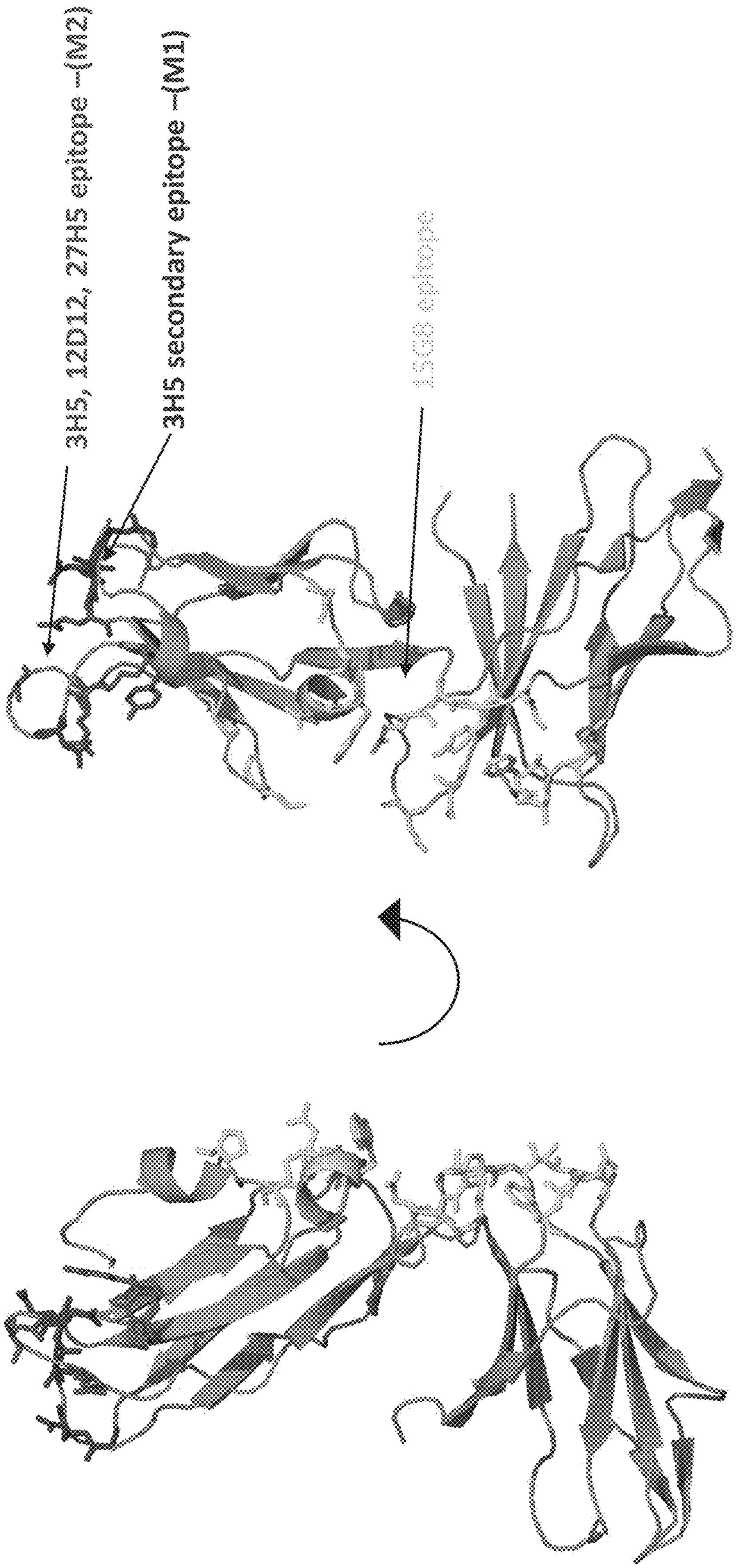

The binding epitopes of most ILT2 antibodies are not known, however, International Patent Publication WO2020/136145 does disclose epitope information for a variety of antibodies. Two general binding regions were found, one within the D1 region and one within the D4 region. In particular, three antibodies designated 3H5, 12D12 and 27H5 were characterized by loss of binding to a mutant with substitutions at E34, R36, Y76, A82 and R84 in D1. One of those antibodies, 3H5, showed diminished binding to a mutation with substitutions at G29, Q30, T32, Q33 and D80 of D1. These residues are exclusively in the D1 region, and are all outside of the 4 regions (all within the interdomain) defined as the binding epitope of the 15G8 antibody (note that in FIG. 18A the sequence starts one amino acid later, so that E34 of WO2020/136145 for example, is E33 in 18A). Thus, antibody 15G8 binds to a different 3-dimensional epitope than that of the antibodies of the WO2020/136145 Publication (FIG. 18D).

Figure 18E:
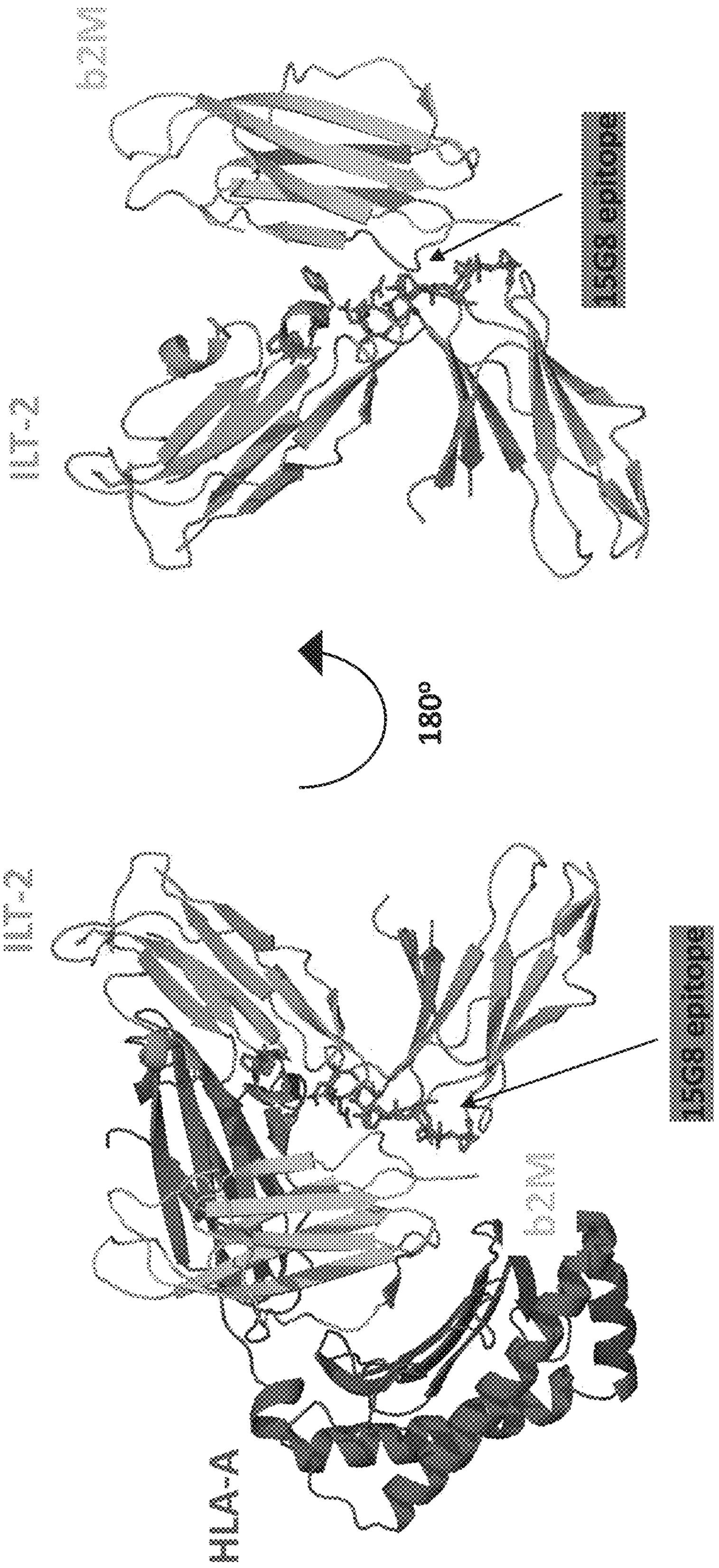
Figure 18F:
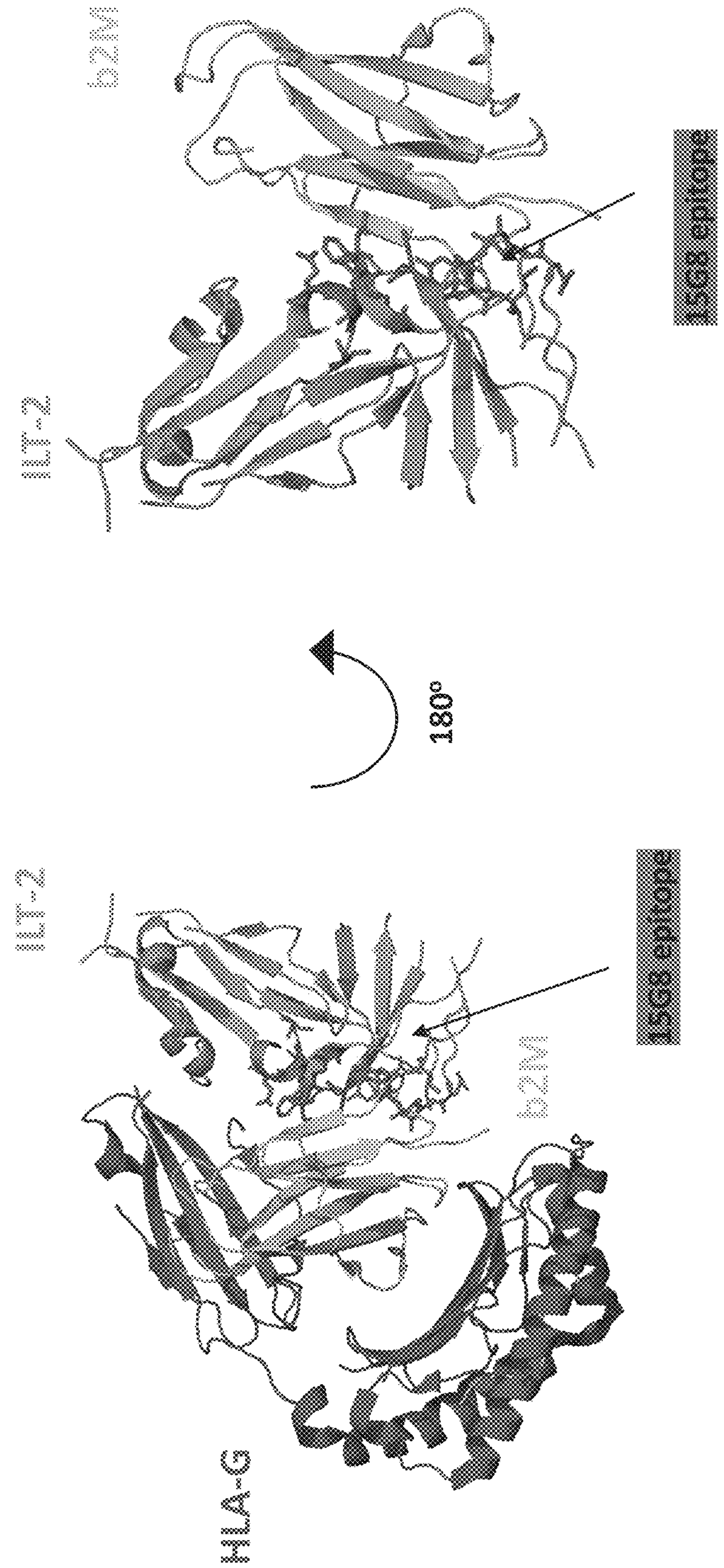

Interestingly, the region defined as the 15G8 epitope, that is the interdomain between D1 and D2, has been identified as the main interaction region of ILT2 that binds with beta-2-microglobulin (B2M) when it is in complex with HLA (see Kuroki et al., "Structural and functional basis for LILRB immune checkpoint receptor recognition of HLA-G isoforms", J. Immuno., 2019, December 15; 203(12):3386-3394.) (FIG. 18E-F). Indeed, residues G97, A98, Y99, I100, Q125 and V126 were specifically identified by Kuroki et al., (Supplementary Figure S2 in Kuroki) as interacting with B2M. These residues fall within interaction regions 3 and 4 for 15G8 and are all considered very highly probably or highly probable residues of the epitope. This strongly suggests that 15G8 inhibits the binding of ILT2 to HLA in a B2M-dependent manner, and indeed blocks ILT2 binding directly to B2M. In contrast, the 3H5, 12D12 and 27H5 antibodies bind to the N-terminal D1 region of ILT2 that interacts with the 3 domain of HLA-G (see Supplementary Figure S2 in Kuroki). This is highly significant as Kuroki et al. found that the main interaction site for ILT2 is the B2M site and binding to the 3 domain is additional and flexible. This may explain 15G8's unique ability to effect T cell, NK cell and macrophage/dendritic cell function: it is blocking the main interaction site of ILT2 and not a secondary site.

Figure 13C:
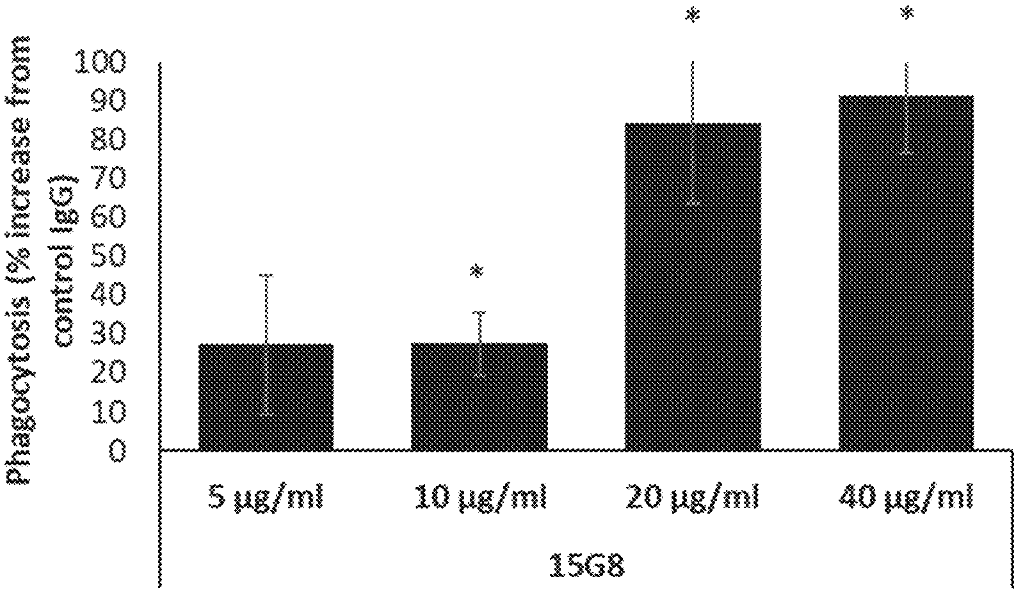
Figure 19A:
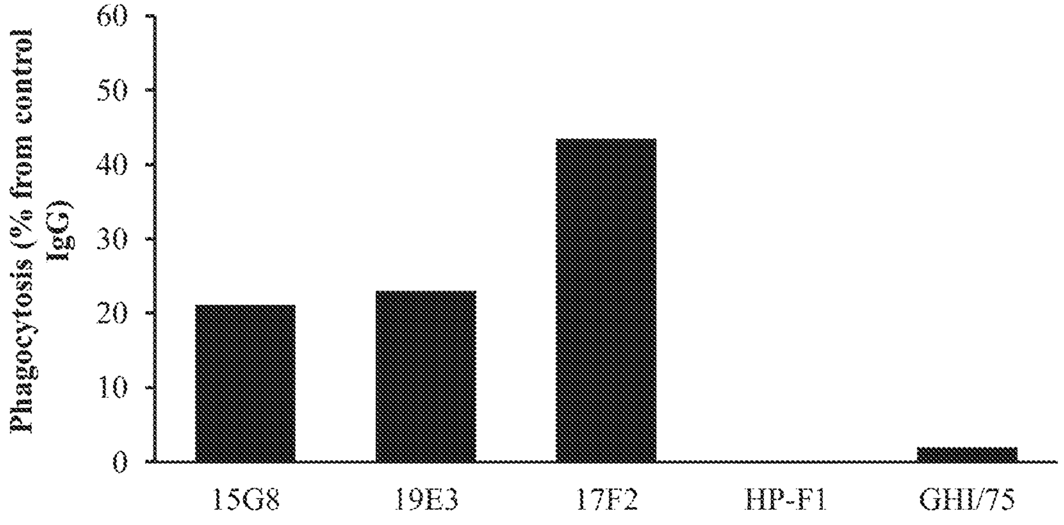
FIGS. 19A-19C. (19A-19B) Bar graphs of % increased phagocytosis as compared to IgG control of (19A) A375-HLA-G and (19B) SKMEL28-HLA-G cancer cells cocultured with macrophages in the presence of various anti-ILT2 antibodies. (19C) A line graph of a competition ILT2 binding ELISA using biotinylated 15G8 antibody in the presence of competing unbiotinylated GHI/75. HP-F1 and 15G8 antibodies.
Figure 19B:
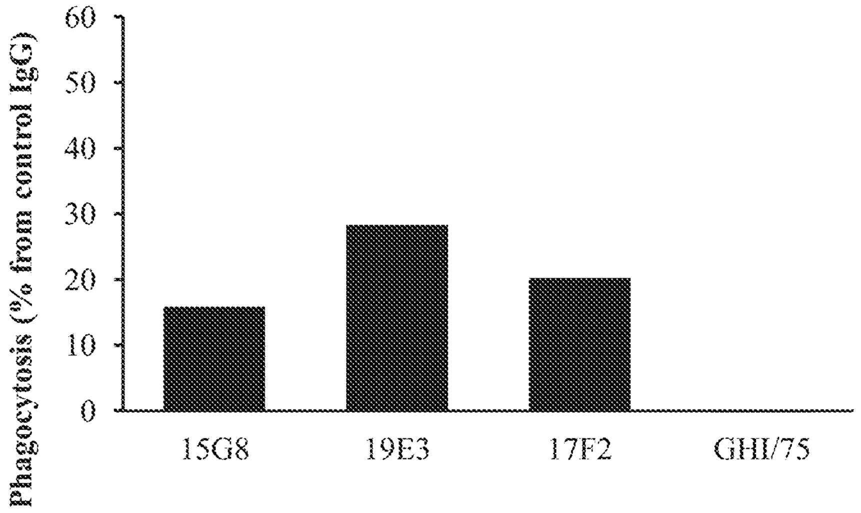

The only ILT2 antibody identified to have any effect on phagocytosis is GHI/75, which was shown to enhance anti-CD47 blockade mediated cancer cell phagocytosis, but was not shown to have an effect on its own (see Barkal et al., "Engagement of MHC class I by the inhibitory receptor LILRB1 suppresses macrophages and is a target of cancer immunotherapy", Nat. Immunol. January; 19(1):76-84). The combined GHI/75 and anti-CD47 effect was found not to be B2M dependent as deletion of B2M had no effect on the increased phagocytosis. Thus, it may be that the effect of 15G8 alone on phagocytosis (FIG. 13A-13C) is B2M dependent, which would explain the unique capabilities of this antibody. The superiority of the antibodies of the invention in this regard was directly tested. A375 or SKMEL28 cancer cells expressing exogenous HLA-G were cocultured with macrophages in the presence of IgG control, the antibodies of the invention, or GHI/75. HP-F1 antibody was also tested in A375 cells. The cancer cell lines stained with PKH67-FITC were incubated with the macrophages which were stained with eFluor 670-APC in the presence of the indicated antibodies. Phagocytosis levels were determined by the percent of macrophages which were double stained, indicating the engulfment of the target cells. The % increase in phagocytosis compared to IgG control was calculated. All three antibodies of the invention increased phagocytosis as compared to control in both cell types (FIG. 19A-19B), with some variability between the antibodies and between the cell types. As expected, neither GHI/75 nor HP-F1 had any effect on phagocytosis. This confirms that the antibodies of the invention are the first anti-ILT2 antibodies that can enhance phagocytosis as a monotherapy.

Figure 19C:
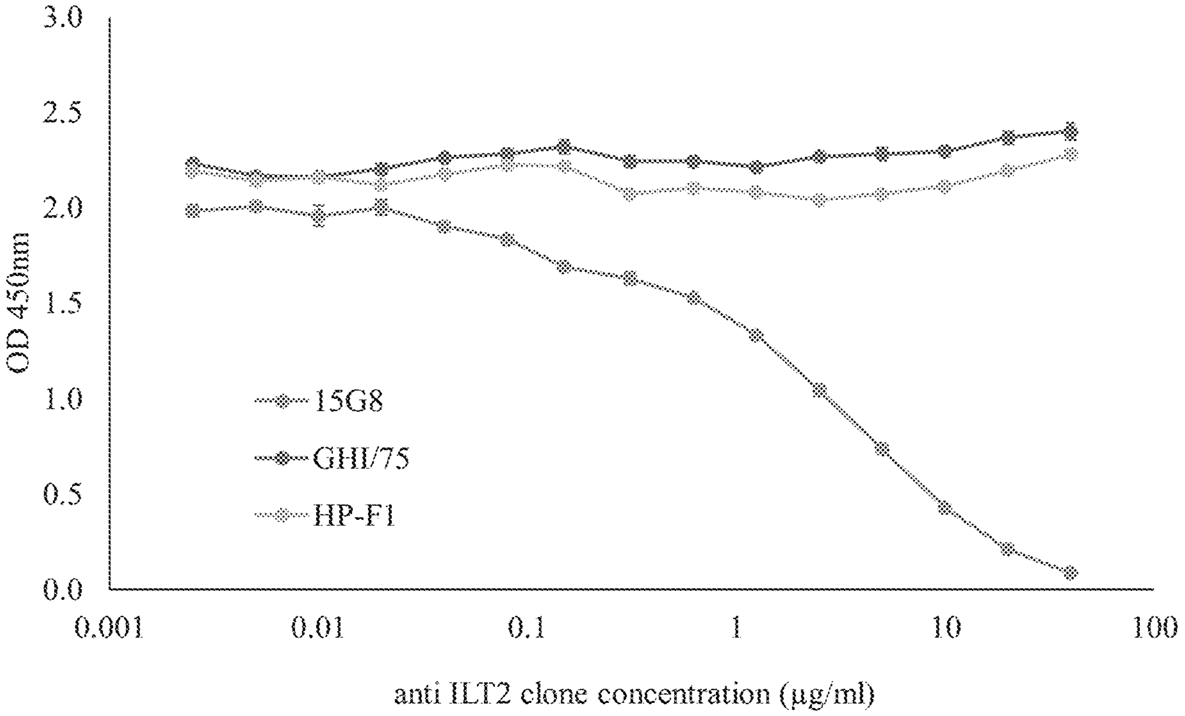

This raises the question of the epitope of GHI/75 and other commercial antibodies. Though the epitopes of these antibodies are not published a competition ELISA assay was performed to see if 15G8 and GH1/75 and HP-F1 could bind ILT2 at the same time. Biotinylated 15G8 antibody was used at a constant concentration (1 μg/ml) in an ILT2 binding ELISA. GHI/75 and HP-F1 were added in increasing concentrations and competition was assessed. Regardless of the amount of these two antibodies added, neither one competed with 15G8 for binding to ILT2 (FIG. 19). In contrast, when naked (unbiotinylated) 15G8 was added, the binding decreased in a dose dependent manner as expected. This indicates that GHI/75 and HP-F1 bind to different epitopes than 15G8. This makes 15G8 the first anti-ILT2 antibody ever identified to bind this epitope, to specifically block interaction with B2M and to be able to simultaneously activate/recruit T cells, NK cells and macrophages/dendritic cells against cancer.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of inducing or enhancing an anti-tumor T-cell response, increasing T-cell proliferation, reducing cancer-induced suppressor myeloid activity, increasing natural killer cell cytotoxicity, increasing macrophage phagocytosis, increasing generation of M1 inflammatory macrophages, decreasing generation of M2 suppressor macrophages, increasing dendritic cell number in a tumor microenvironment, increasing dendritic cell activation, treating an HLA-G expressing cancer, or treating a MHC-I expressing cancer in a human subject in need thereof, comprising administering to the subject a monoclonal anti-immunoglobulin-like transcript 2 (ILT2) antibody or an antigen-binding fragment thereof, wherein the anti-ILT2 antibody comprises three heavy chain CDRs (HCDRs) and three light chain CDRs (LCDRs), wherein the HCDR1-3 and LCDR1-3 comprise:

a) SEQ ID NOs: 13-18, respectively, wherein X in SEQ ID NO: 15 is selected from A, C, and S;
b) SEQ ID NOs: 1-6, respectively; or
c) SEQ ID NOs: 7-12, respectively.

2. A method for treating an HLA-G or MHC-I expressing cancer in a human subject in need thereof, comprising administering to the subject a monoclonal anti-immunoglobulin-like transcript 2 (ILT2) antibody or an antigen-binding fragment thereof, wherein the anti-ILT2 antibody comprises three heavy chain CDRs (HCDRs) and three light chain CDRs (LCDRs), wherein the HCDR1-3 and LCDR1-3 comprise:

a) SEQ ID NOs: 13-18, respectively, wherein X in SEQ ID NO: 15 is selected from A, C, and S;
b) SEQ ID NOs: 1-6, respectively; or
c) SEQ ID NOs: 7-12, respectively.

3. The method of claim 2, wherein the anti-ILT2 antibody comprises a heavy chain and a light chain comprising the amino acid sequences of a) SEQ ID NOs: 23 and 24, respectively, wherein X in SEQ ID NO: 23 is selected from A, C and S;
b) SEQ ID NOs: 23 and 45, respectively, wherein X in SEQ ID NO: 23 is selected from A, C and S;
c) SEQ ID NOs: 28 and 24, respectively;
d) SEQ ID NOs: 29 and 24, respectively;
e) SEQ ID NOs: 30 and 45, respectively;
f) SEQ ID NOs: 19 and 20, respectively; or
g) SEQ ID NOs: 21 and 22, respectively.

4. The method of claim 2, wherein the anti-ILT2 antibody comprises a heavy chain that comprises SEQ ID NO: 28 and a light chain that comprises SEQ ID NO: 24.

5. The method of claim 4, wherein the anti-ILT2 antibody is of human IgG4 isotype subclass.

6. The method of claim 2, wherein said treatment further comprises confirming that expression of ILT2 or soluble HLA-G in a sample from the subject is greater than expression of said molecule in a sample from a healthy control subject.

7. The method of claim 6, wherein said confirming comprises measuring expression of said ILT2 or soluble HLA-G before administering the anti-ILT2 antibody or antigen-binding portion to the subject.

8. The method of claim 2, wherein said treatment comprises confirming expression of ILT2 in an immune cell of said subject, wherein said immune cell is selected from a peripheral blood immune cell, an intratumor immune cell, a CD8 positive T cell, a macrophage, an NK cell, and a TEMRA cell.

9. The method of claim 2, further comprising administering to the subject an anti-PD-L1- or anti-PD-1-based therapy.

10. The method of claim 2, further comprising administering to the subject an opsonizing agent.

11. The method of claim 10, wherein the opsonizing agent is an EGFR inhibitor.

12. A method for treating cancer by increasing efficacy of an anti-PD-L1- or anti-PD-1-based therapy against a cancer cell expressing HLA-G, MHC-I, or both in a subject in need thereof, comprising administering to the subject a monoclonal anti-immunoglobulin-like transcript 2 (ILT2) antibody or an antigen-binding fragment thereof, wherein the anti-ILT2 antibody comprises three heavy chain CDRs (HCDRs) and three light chain CDRs (LCDRs), wherein the HCDR1-3 and LCDR1-3 comprise:

a) SEQ ID NOs: 13-18, respectively, wherein X in SEQ ID NO: 15 is selected from A, C, and S;

b) SEQ ID NOs: 1-6, respectively; or c) SEQ ID NOs: 7-12, respectively.

13. The method of claim 12, wherein the anti-ILT2 antibody comprises a heavy chain and a light chain comprising the amino acid sequences of a) SEQ ID NOs: 23 and 24, respectively, wherein X in SEQ ID NO: 23 is selected from A, C and S;

b) SEQ ID NOs: 23 and 45, respectively, wherein X in SEQ ID NO: 23 is selected from A, C and S;

c) SEQ ID NOs: 28 and 24, respectively;

d) SEQ ID NOs: 29 and 24, respectively;

e) SEQ ID NOs: 30 and 45, respectively;

f) SEQ ID NOs: 19 and 20, respectively; or g) SEQ ID NOs: 21 and 22, respectively.

14. The method of claim 12, wherein the anti-ILT2 antibody comprises a heavy chain that comprises SEQ ID NO: 28 and a light chain that comprises SEQ ID NO: 24.

15. The method of claim 14, wherein the anti-ILT2 antibody is of human IgG4 isotype subclass.

16. The method of claim 12, wherein said anti-PD-L1- or anti-PD-1-based therapy is an anti-PD-1 blocking antibody.

17. The method of claim 12, wherein said cancer is refractory to anti-PD-L1- or anti-PD-1-based therapy.

18. The method of claim 12, further comprising administering to the subject an anti-PD-L1- or anti-PD-1-based therapy.

19. The method of claim 12, further comprising administering to the subject an opsonizing agent.

20. The method of claim 19, wherein the opsonizing agent is an EGFR inhibitor.

* * * * *

SEQUENCE LISTING

```
<160> NUMBER OF SEQ ID NOS: 47

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

Asp His Thr Ile His
1               5


<210> SEQ ID NO 2
<211> LENGTH: 17
<212> TYPE: PRT
<213> ORGANISM: Artificial
<220> FEATURE:
<223> OTHER INFORMATION: Synthetic

<400> SEQUENCE: 2

Tyr Ile Tyr Pro Arg Asp Gly Ser Thr Lys Tyr Asn Glu Lys Phe Lys
1               5                   10                  15

Gly


<210> SEQ ID NO 3
```

<211> LENGTH: 7
<212> TYPE: PRT
<213> ORGANISM: Artificial
<220> FEATURE:
<223> OTHER INFORMATION: Synthetic

<400> SEQUENCE: 3

Thr Trp Asp Tyr Phe Asp Tyr
1               5

<210> SEQ ID NO 4
<211> LENGTH: 15
<212> TYPE: PRT
<213> ORGANISM: Artificial
<220> FEATURE:
<223> OTHER INFORMATION: Synthetic

<400> SEQUENCE: 4

Arg Ala Ser Glu Ser Val Asp Ser Tyr Gly Asn Ser Phe Met His
1               5                   10                  15

<210> SEQ ID NO 5
<211> LENGTH: 7
<212> TYPE: PRT
<213> ORGANISM: Artificial
<220> FEATURE:
<223> OTHER INFORMATION: Synthetic

<400> SEQUENCE: 5

Arg Ala Ser Asn Leu Glu Ser
1               5

<210> SEQ ID NO 6
<211> LENGTH: 9
<212> TYPE: PRT
<213> ORGANISM: Artificial
<220> FEATURE:
<223> OTHER INFORMATION: Synthetic

<400> SEQUENCE: 6

Gln Gln Ser Asn Glu Asp Pro Tyr Thr
1               5

<210> SEQ ID NO 7
<211> LENGTH: 10
<212> TYPE: PRT
<213> ORGANISM: Artificial
<220> FEATURE:
<223> OTHER INFORMATION: Synthetic

<400> SEQUENCE: 7

Gly Tyr Thr Phe Thr Ser Tyr Gly Ile Ser
1               5                   10

<210> SEQ ID NO 8
<211> LENGTH: 17
<212> TYPE: PRT
<213> ORGANISM: Artificial
<220> FEATURE:
<223> OTHER INFORMATION: Synthetic

<400> SEQUENCE: 8

Glu Ile Tyr Pro Gly Ser Gly Asn Ser Tyr Tyr Asn Glu Lys Phe Lys
1               5                   10                  15

Gly

<210> SEQ ID NO 9
<211> LENGTH: 8
<212> TYPE: PRT
<213> ORGANISM: Artificial
<220> FEATURE:
<223> OTHER INFORMATION: Synthetic

<400> SEQUENCE: 9

Ser Asn Asp Gly Tyr Pro Asp Tyr
1 5

<210> SEQ ID NO 10
<211> LENGTH: 11
<212> TYPE: PRT
<213> ORGANISM: Artificial
<220> FEATURE:
<223> OTHER INFORMATION: Synthetic

<400> SEQUENCE: 10

Lys Ala Ser Asp His Ile Asn Asn Trp Leu Ala
1 5 10

<210> SEQ ID NO 11
<211> LENGTH: 7
<212> TYPE: PRT
<213> ORGANISM: Artificial
<220> FEATURE:
<223> OTHER INFORMATION: Synthetic

<400> SEQUENCE: 11

Gly Ala Thr Ser Leu Glu Thr
1 5

<210> SEQ ID NO 12
<211> LENGTH: 9
<212> TYPE: PRT
<213> ORGANISM: Artificial
<220> FEATURE:
<223> OTHER INFORMATION: Synthetic

<400> SEQUENCE: 12

Gln Gln Tyr Trp Ser Thr Pro Trp Thr
1 5

<210> SEQ ID NO 13
<211> LENGTH: 6
<212> TYPE: PRT
<213> ORGANISM: Artificial
<220> FEATURE:
<223> OTHER INFORMATION: Synthetic

<400> SEQUENCE: 13

Ser Gly Tyr Tyr Trp Asn
1 5

<210> SEQ ID NO 14
<211> LENGTH: 16
<212> TYPE: PRT
<213> ORGANISM: Artificial
<220> FEATURE:
<223> OTHER INFORMATION: Synthetic

<400> SEQUENCE: 14

Tyr Ile Ser Tyr Asp Gly Ser Asn Asn Tyr Asn Pro Ser Leu Lys Asn
1 5 10 15

<210> SEQ ID NO 15

<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (10)..(10)
<223> OTHER INFORMATION: X is selected from A, C and S.

<400> SEQUENCE: 15

```
Gly Tyr Ser Tyr Tyr Tyr Ala Met Asp Xaa
1               5                   10
```

<210> SEQ ID NO 16
<211> LENGTH: 11
<212> TYPE: PRT
<213> ORGANISM: Artificial
<220> FEATURE:
<223> OTHER INFORMATION: Synthetic

<400> SEQUENCE: 16

```
Arg Thr Ser Gln Asp Ile Ser Asn Tyr Leu Asn
1               5                   10
```

<210> SEQ ID NO 17
<211> LENGTH: 7
<212> TYPE: PRT
<213> ORGANISM: Artificial
<220> FEATURE:
<223> OTHER INFORMATION: Synthetic

<400> SEQUENCE: 17

```
Tyr Thr Ser Arg Leu His Ser
1               5
```

<210> SEQ ID NO 18
<211> LENGTH: 8
<212> TYPE: PRT
<213> ORGANISM: Artificial
<220> FEATURE:
<223> OTHER INFORMATION: Synthetic

<400> SEQUENCE: 18

```
Gln Gln Gly Asn Thr Leu Pro Thr
1               5
```

<210> SEQ ID NO 19
<211> LENGTH: 116
<212> TYPE: PRT
<213> ORGANISM: Artificial
<220> FEATURE:
<223> OTHER INFORMATION: Synthetic

<400> SEQUENCE: 19

```
Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
        35                  40                  45

Gly Tyr Ile Tyr Pro Arg Asp Gly Ser Thr Lys Tyr Asn Glu Lys Phe
    50                  55                  60

Lys Gly Lys Ala Thr Leu Thr Ala Asp Lys Ser Ser Ser Thr Ala Tyr
65                  70                  75                  80
```

```
Met Gln Leu Asn Ser Leu Thr Ser Glu Asp Ser Ala Val Tyr Phe Cys
                85                  90                  95

Ala Arg Thr Trp Asp Tyr Phe Asp Tyr Trp Gly Gln Gly Thr Thr Leu
            100                 105                 110

Thr Val Ser Ser
        115


<210> SEQ ID NO 20
<211> LENGTH: 111
<212> TYPE: PRT
<213> ORGANISM: Artificial
<220> FEATURE:
<223> OTHER INFORMATION: Synthetic

<400> SEQUENCE: 20

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110


<210> SEQ ID NO 21
<211> LENGTH: 117
<212> TYPE: PRT
<213> ORGANISM: Artificial
<220> FEATURE:
<223> OTHER INFORMATION: Synthetic

<400> SEQUENCE: 21

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Val
        35                  40                  45

Gly Glu Ile Tyr Pro Gly Ser Gly Asn Ser Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Ser Asn Asp Gly Tyr Pro Asp Tyr Trp Gly Gln Gly Thr Thr
            100                 105                 110

Leu Thr Val Ser Ser
        115


<210> SEQ ID NO 22
<211> LENGTH: 107
<212> TYPE: PRT
<213> ORGANISM: Artificial
```

<220> FEATURE:
<223> OTHER INFORMATION: Synthetic

<400> SEQUENCE: 22

Asp Ile Gln Met Thr Gln Ser Ser Ser Tyr Leu Ser Val Ser Leu Gly
1 5 10 15

Gly Arg Val Thr Ile Thr Cys Lys Ala Ser Asp His Ile Asn Asn Trp
20 25 30

Leu Ala Trp Tyr Gln Gln Lys Pro Gly Asn Ala Pro Arg Leu Leu Ile
35 40 45

Ser Gly Ala Thr Ser Leu Glu Thr Gly Val Pro Ser Arg Phe Ser Gly
50 55 60

Ser Gly Ser Gly Lys Asp Tyr Thr Leu Ser Ile Thr Ser Leu Gln Thr
65 70 75 80

Glu Asp Val Ala Thr Tyr Tyr Cys Gln Gln Tyr Trp Ser Thr Pro Trp
85 90 95

Thr Phe Gly Gly Gly Thr Lys Leu Glu Ile Lys
100 105

<210> SEQ ID NO 23
<211> LENGTH: 119
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (108)..(108)
<223> OTHER INFORMATION: X is selected from A, C and S.

<400> SEQUENCE: 23

Asp Val Gln Leu Gln Gly Ser Gly Pro Gly Leu Val Lys Pro Ser Glu
1 5 10 15

Thr Leu Ser Leu Thr Cys Ser Val Thr Gly Tyr Ser Ile Thr Ser Gly
20 25 30

Tyr Tyr Trp Asn Trp Ile Arg Gln Phe Pro Gly Lys Lys Leu Glu Trp
35 40 45

Met Gly Tyr Ile Ser Tyr Asp Gly Ser Asn Asn Tyr Asn Pro Ser Leu
50 55 60

Lys Asn Arg Ile Thr Ile Ser Arg Asp Thr Ser Lys Asn Gln Phe Ser
65 70 75 80

Leu Lys Leu Asn Ser Val Thr Ala Ala Asp Thr Ala Thr Tyr Tyr Cys
85 90 95

Ala His Gly Tyr Ser Tyr Tyr Tyr Ala Met Asp Xaa Trp Gly Gln Gly
100 105 110

Thr Ser Val Thr Val Ser Ser
115

<210> SEQ ID NO 24
<211> LENGTH: 106
<212> TYPE: PRT
<213> ORGANISM: Artificial
<220> FEATURE:
<223> OTHER INFORMATION: Synthetic

<400> SEQUENCE: 24

Asp Ile Gln Met Thr Gln Ser Pro Ser Ser Leu Ser Ala Ser Val Gly
1 5 10 15

Asp Arg Val Thr Ile Thr Cys Arg Thr Ser Gln Asp Ile Ser Asn Tyr
20 25 30

Leu Asn Trp Tyr Gln Gln Lys Pro Gly Lys Ala Val Lys Leu Leu Ile
35 40 45

Ser Tyr Thr Ser Arg Leu His Ser Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln Gln Gly Asn Thr Leu Pro Thr
85 90 95

Phe Gly Gln Gly Thr Lys Leu Glu Ile Lys
100 105

<210> SEQ ID NO 25
<211> LENGTH: 10
<212> TYPE: PRT
<213> ORGANISM: Artificial
<220> FEATURE:
<223> OTHER INFORMATION: Synthetic

<400> SEQUENCE: 25

Gly Tyr Ser Tyr Tyr Tyr Ala Met Asp Ala
1 5 10

<210> SEQ ID NO 26
<211> LENGTH: 10
<212> TYPE: PRT
<213> ORGANISM: Artificial
<220> FEATURE:
<223> OTHER INFORMATION: Synthetic

<400> SEQUENCE: 26

Gly Tyr Ser Tyr Tyr Tyr Ala Met Asp Ser
1 5 10

<210> SEQ ID NO 27
<211> LENGTH: 10
<212> TYPE: PRT
<213> ORGANISM: Artificial
<220> FEATURE:
<223> OTHER INFORMATION: Synthetic

<400> SEQUENCE: 27

Gly Tyr Ser Tyr Tyr Tyr Ala Met Asp Cys
1 5 10

<210> SEQ ID NO 28
<211> LENGTH: 119
<212> TYPE: PRT
<213> ORGANISM: Artificial
<220> FEATURE:
<223> OTHER INFORMATION: Synthetic

<400> SEQUENCE: 28

Asp Val Gln Leu Gln Gly Ser Gly Pro Gly Leu Val Lys Pro Ser Glu
1 5 10 15

Thr Leu Ser Leu Thr Cys Ser Val Thr Gly Tyr Ser Ile Thr Ser Gly
20 25 30

Tyr Tyr Trp Asn Trp Ile Arg Gln Phe Pro Gly Lys Lys Leu Glu Trp
35 40 45

Met Gly Tyr Ile Ser Tyr Asp Gly Ser Asn Asn Tyr Asn Pro Ser Leu
50 55 60

Lys Asn Arg Ile Thr Ile Ser Arg Asp Thr Ser Lys Asn Gln Phe Ser
65 70 75 80

Leu Lys Leu Asn Ser Val Thr Ala Ala Asp Thr Ala Thr Tyr Tyr Cys
85 90 95

Ala His Gly Tyr Ser Tyr Tyr Tyr Ala Met Asp Ala Trp Gly Gln Gly
100 105 110

Thr Ser Val Thr Val Ser Ser
115

<210> SEQ ID NO 29
<211> LENGTH: 119
<212> TYPE: PRT
<213> ORGANISM: Artificial
<220> FEATURE:
<223> OTHER INFORMATION: Synthetic

<400> SEQUENCE: 29

Asp Val Gln Leu Gln Gly Ser Gly Pro Gly Leu Val Lys Pro Ser Glu
1 5 10 15

Thr Leu Ser Leu Thr Cys Ser Val Thr Gly Tyr Ser Ile Thr Ser Gly
20 25 30

Tyr Tyr Trp Asn Trp Ile Arg Gln Phe Pro Gly Lys Lys Leu Glu Trp
35 40 45

Met Gly Tyr Ile Ser Tyr Asp Gly Ser Asn Asn Tyr Asn Pro Ser Leu
50 55 60

Lys Asn Arg Ile Thr Ile Ser Arg Asp Thr Ser Lys Asn Gln Phe Ser
65 70 75 80

Leu Lys Leu Asn Ser Val Thr Ala Ala Asp Thr Ala Thr Tyr Tyr Cys
85 90 95

Ala His Gly Tyr Ser Tyr Tyr Tyr Ala Met Asp Ser Trp Gly Gln Gly
100 105 110

Thr Ser Val Thr Val Ser Ser
115

<210> SEQ ID NO 30
<211> LENGTH: 119
<212> TYPE: PRT
<213> ORGANISM: Artificial
<220> FEATURE:
<223> OTHER INFORMATION: Synthetic

<400> SEQUENCE: 30

Asp Val Gln Leu Gln Gly Ser Gly Pro Gly Leu Val Lys Pro Ser Gln
1 5 10 15

Ser Leu Ser Leu Thr Cys Ser Val Thr Gly Tyr Ser Ile Thr Ser Gly
20 25 30

Tyr Tyr Trp Asn Trp Ile Arg Gln Phe Pro Gly Asn Lys Leu Glu Trp
35 40 45

Met Gly Tyr Ile Ser Tyr Asp Gly Ser Asn Asn Tyr Asn Pro Ser Leu
50 55 60

Lys Asn Arg Ile Ser Ile Thr Arg Asp Thr Ser Lys Asn Gln Phe Phe
65 70 75 80

Leu Lys Leu Asn Ser Val Thr Ser Glu Asp Thr Ala Thr Tyr Tyr Cys
85 90 95

Ala His Gly Tyr Ser Tyr Tyr Tyr Ala Met Asp Cys Trp Gly Gln Gly
100 105 110

Thr Ser Val Thr Val Ser Ser
115

-continued

```
<210> SEQ ID NO 31
<211> LENGTH: 650
<212> TYPE: PRT
<213> ORGANISM: Homo sapiens

<400> SEQUENCE: 31

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Ile Leu Gln
    130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
    290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
    370                 375                 380
```

```
Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Gly Pro Ser Ser Pro Thr Thr Gly
            420                 425                 430

Pro Thr Ser Thr Ser Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys His Thr Gln Pro Glu Asp Gly
    530                 535                 540

Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
                565                 570                 575

Pro Pro Ser Pro Leu Ser Gly Glu Phe Leu Asp Thr Lys Asp Arg Gln
            580                 585                 590

Ala Glu Glu Asp Arg Gln Met Asp Thr Glu Ala Ala Ala Ser Glu Ala
        595                 600                 605

Pro Gln Asp Val Thr Tyr Ala Gln Leu His Ser Leu Thr Leu Arg Arg
    610                 615                 620

Glu Ala Thr Glu Pro Pro Pro Ser Gln Glu Gly Pro Ser Pro Ala Val
625                 630                 635                 640

Pro Ser Ile Tyr Ala Thr Leu Ala Ile His
                645                 650
```

<210> SEQ ID NO 32
<211> LENGTH: 351
<212> TYPE: DNA
<213> ORGANISM: Artificial
<220> FEATURE:
<223> OTHER INFORMATION: Synthetic

<400> SEQUENCE: 32

```
caggttcagc tgcagcagtc tggagctgag ctggcgaggc ctggggcttc agtgaagctg      60

tcctgcaagg cttctggcta caccttcaca agctatggta taagctgggt gaagcagaga     120

actggacagg gccttgagtg ggttggagag atttatcctg gaagtggtaa ttcttactac     180

aatgagaagt tcaagggcaa ggccacactg actgcagaca aatcctccag cacagcgtac     240

atggagctcc gcagcctgac atctgaggac tctgcggtct atttctgtgc aagatcgaat     300

gatggttacc ctgactactg gggccaaggc accactctca cagtctcctc a              351
```

<210> SEQ ID NO 33
<211> LENGTH: 357
<212> TYPE: DNA
<213> ORGANISM: Artificial
<220> FEATURE:

-continued

<223> OTHER INFORMATION: Synthetic

<400> SEQUENCE: 33
gatgtacagc ttcaggggtc aggacctggc ctcgtgaaac cttctcagtc tctgtctctc 60
acctgctctg tcactggcta ctccatcacc agtggttatt actggaactg gatccggcag 120
tttccaggaa acaaactgga atggatgggc tacataagct acgatggtag caataactac 180
aacccatctc tcaaaaatcg aatctccatc actcgtgaca catctaagaa ccagtttttc 240
ctgaagttga attctgtgac ttctgaggac acagccacat attactgtgc ccatggttac 300
tcatattact atgctatgga ctgctggggt caaggaacct cagtcaccgt ctcctca 357

<210> SEQ ID NO 34
<211> LENGTH: 357
<212> TYPE: DNA
<213> ORGANISM: Artificial
<220> FEATURE:
<223> OTHER INFORMATION: Synthetic

<400> SEQUENCE: 34
gatgtccagc tgcaaggctc tggccctgga ctggttaagc cttccgagac actgtccctg 60
acctgctctg tgaccggcta ctctatcacc tccggctact actggaactg gatcagacag 120
ttccccggca agaaactgga atggatgggc tacatctcct acgacggctc caacaactac 180
aaccccagcc tgaagaaccg gatcaccatc tctcgggaca cctccaagaa ccagttctcc 240
ctgaagctga actccgtgac cgctgccgat accgctacct actactgtgc tcacggctac 300
tcctactact acgccatgga tgcttggggc cagggcacat ctgtgacagt gtcctct 357

<210> SEQ ID NO 35
<211> LENGTH: 348
<212> TYPE: DNA
<213> ORGANISM: Artificial
<220> FEATURE:
<223> OTHER INFORMATION: Synthetic

<400> SEQUENCE: 35
caggttcagc tgcaacagtc tgacgctgag ttggtgaaac ctggagcttc agtgaagata 60
tcctgcaagg tttctggcta caccttcact gaccatacta ttcactggat gaagcagagg 120
cctgaacagg gcctggaatg gattggatat atttatccta gagatggtag tactaagtac 180
aatgagaagt tcaagggcaa ggccacattg actgcagaca aatcctccag cacagcctac 240
atgcagctca acagcctgac atctgaggac tctgcagtct atttctgtgc aagaacctgg 300
gactactttg actactgggg ccaaggcacc actctcacag tctcctca 348

<210> SEQ ID NO 36
<211> LENGTH: 333
<212> TYPE: DNA
<213> ORGANISM: Artificial
<220> FEATURE:
<223> OTHER INFORMATION: Synthetic

<400> SEQUENCE: 36
gacattgtgc tgacccaatc tccagcttct ttggctgtgt ctctagggca gagggccacc 60
atatcctgca gagccagtga aagtgttgat agttatggca atagttttat gcactggtac 120
cagcagaaac caggacagcc acccaaactc ctcatctatc gtgcatccaa cctagaatct 180
gggatccctg ccaggttcag tggcagtggg tctaggacag acttcaccct caccattaat 240
cctgtggagg ctgatgatgt tgcaacctat tactgtcagc aaagtaatga ggatccgtac 300

-continued acgttcggag gggggaccaa gctggaaata aaa 333

<210> SEQ ID NO 37
<211> LENGTH: 318
<212> TYPE: DNA
<213> ORGANISM: Artificial
<220> FEATURE:
<223> OTHER INFORMATION: Synthetic

<400> SEQUENCE: 37
gatatccaga tgacacagac tacatcctcc ctgtctgcct ctctgggaga cagagtcacc 60
atcagttgca ggacaagtca ggacattagc aattatttaa actggtatca gcagaaacca 120
gatggaactg ttaaactcct gatctcctac acatcaagat tgcactcagg agtcccatca 180
aggttcagtg gcagtgggtc tggaacagat tattctctca ccattagcaa cctggagcaa 240
gaagatattg ccacttactt ttgccaacag ggtaatacgc ttcccacgtt cggctcgggg 300
acaaagttgg aaataaaa 318

<210> SEQ ID NO 38
<211> LENGTH: 318
<212> TYPE: DNA
<213> ORGANISM: Artificial
<220> FEATURE:
<223> OTHER INFORMATION: Synthetic

<400> SEQUENCE: 38
gacatccaga tgacccagtc tccatcctct ctgtctgcct ctgtgggcga cagagtgacc 60
atcacctgtc ggacctctca ggacatctcc aactacctga actggtatca gcagaaaccc 120
ggcaaggccg tgaagctgct gatctcctac acctccagac tgcactctgg cgtgccctcc 180
agattttctg gctctggatc tggcaccgac tacaccctga ccatcagttc tctgcagcct 240
gaggacttcg ccacctacta ctgtcagcag ggcaacaccc tgcctacctt tggccagggc 300
accaagctgg aaatcaag 318

<210> SEQ ID NO 39
<211> LENGTH: 321
<212> TYPE: DNA
<213> ORGANISM: Artificial
<220> FEATURE:
<223> OTHER INFORMATION: Synthetic

<400> SEQUENCE: 39
gacatccaga tgacacaatc ttcatcctac ttgtctgtat ctctaggagg cagagtcacc 60
attacttgca aggcaagtga ccacattaat aattggttag cctggtatca gcagaaacca 120
ggaaatgctc ctaggctctt aatatctggt gcaaccagtt tggaaactgg ggttccttca 180
agattcagtg gcagtggatc tggaaaggat tacactctca gcattaccag tcttcagact 240
gaagatgttg ctacttatta ctgtcaacag tattggagta ctccgtggac gttcggtgga 300
ggcaccaagc tggaaatcaa a 321

<210> SEQ ID NO 40
<211> LENGTH: 393
<212> TYPE: PRT
<213> ORGANISM: Homo sapiens

<400> SEQUENCE: 40

His Leu Pro Lys Pro Thr Leu Trp Ala Glu Pro Gly Ser Val Ile Thr
1 5 10 15

-continued

```
Gln Gly Ser Pro Val Thr Leu Arg Cys Gln Gly Gly Gln Glu Thr Gln
            20                  25                  30

Glu Tyr Arg Leu Tyr Arg Glu Lys Lys Thr Ala Leu Trp Ile Thr Arg
        35                  40                  45

Ile Pro Gln Glu Leu Val Lys Lys Gly Gln Phe Pro Ile Pro Ser Ile
    50                  55                  60

Thr Trp Glu His Ala Gly Arg Tyr Arg Cys Tyr Tyr Gly Ser Asp Thr
65                  70                  75                  80

Ala Gly Arg Ser Glu Ser Ser Asp Pro Leu Glu Leu Val Val Thr Gly
                85                  90                  95

Ala Tyr Ile Lys Pro Thr Leu Ser Ala Gln Pro Ser Pro Val Val Asn
            100                 105                 110

Ser Gly Gly Asn Val Ile Leu Gln Cys Asp Ser Gln Val Ala Phe Asp
        115                 120                 125

Gly Phe Ser Leu Cys Lys Glu Gly Glu Asp Glu His Pro Gln Cys Leu
    130                 135                 140

Asn Ser Gln Pro His Ala Arg Gly Ser Ser Arg Ala Ile Phe Ser Val
145                 150                 155                 160

Gly Pro Val Ser Pro Ser Arg Arg Trp Trp Tyr Arg Cys Tyr Ala Tyr
                165                 170                 175

Asp Ser Asn Ser Pro Tyr Glu Trp Ser Leu Pro Ser Asp Leu Leu Glu
            180                 185                 190

Leu Leu Val Leu Gly Val Ser Lys Lys Pro Ser Leu Ser Val Gln Pro
        195                 200                 205

Gly Pro Ile Val Ala Pro Glu Glu Thr Leu Thr Leu Gln Cys Gly Ser
    210                 215                 220

Asp Ala Gly Tyr Asn Arg Phe Val Leu Tyr Lys Asp Gly Glu Arg Asp
225                 230                 235                 240

Phe Leu Gln Leu Ala Gly Ala Gln Pro Gln Ala Gly Leu Ser Gln Ala
                245                 250                 255

Asn Phe Thr Leu Gly Pro Val Ser Arg Ser Tyr Gly Gly Gln Tyr Arg
            260                 265                 270

Cys Tyr Gly Ala His Asn Leu Ser Ser Glu Trp Ser Ala Pro Ser Asp
        275                 280                 285

Pro Leu Asp Ile Leu Ile Ala Gly Gln Phe Tyr Asp Arg Val Ser Leu
    290                 295                 300

Ser Val Gln Pro Gly Pro Thr Val Ala Ser Gly Glu Asn Val Thr Leu
305                 310                 315                 320

Leu Cys Gln Ser Gln Gly Trp Met Gln Thr Phe Leu Leu Thr Lys Glu
                325                 330                 335

Gly Ala Ala Asp Asp Pro Trp Arg Leu Arg Ser Thr Tyr Gln Ser Gln
            340                 345                 350

Lys Tyr Gln Ala Glu Phe Pro Met Gly Pro Val Thr Ser Ala His Ala
        355                 360                 365

Gly Thr Tyr Arg Cys Tyr Gly Ser Gln Ser Ser Lys Pro Tyr Leu Leu
    370                 375                 380

Thr His Pro Ser Asp Pro Leu Glu Leu
385                 390
```

<210> SEQ ID NO 41
<211> LENGTH: 15
<212> TYPE: PRT
<213> ORGANISM: Homo sapiens

<400> SEQUENCE: 41

Val Lys Lys Gly Gln Phe Pro Ile Pro Ser Ile Thr Trp Glu His
1 5 10 15

<210> SEQ ID NO 42
<211> LENGTH: 15
<212> TYPE: PRT
<213> ORGANISM: Homo sapiens

<400> SEQUENCE: 42

Leu Glu Leu Val Val Thr Gly Ala Tyr Ile Lys Pro Thr Leu Ser
1 5 10 15

<210> SEQ ID NO 43
<211> LENGTH: 15
<212> TYPE: PRT
<213> ORGANISM: Homo sapiens

<400> SEQUENCE: 43

Val Ile Leu Gln Cys Asp Ser Gln Val Ala Phe Asp Gly Phe Ser
1 5 10 15

<210> SEQ ID NO 44
<211> LENGTH: 15
<212> TYPE: PRT
<213> ORGANISM: Homo sapiens

<400> SEQUENCE: 44

Trp Tyr Arg Cys Tyr Ala Tyr Asp Ser Asn Ser Pro Tyr Glu Trp
1 5 10 15

<210> SEQ ID NO 45
<211> LENGTH: 106
<212> TYPE: PRT
<213> ORGANISM: Artificial
<220> FEATURE:
<223> OTHER INFORMATION: Synthetic

<400> SEQUENCE: 45

Asp Ile Gln Met Thr Gln Thr Thr Ser Ser Leu Ser Ala Ser Leu Gly
1 5 10 15

Asp Arg Val Thr Ile Ser Cys Arg Thr Ser Gln Asp Ile Ser Asn Tyr
20 25 30

Leu Asn Trp Tyr Gln Gln Lys Pro Asp Gly Thr Val Lys Leu Leu Ile
35 40 45

Ser Tyr Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Thr
85 90 95

Phe Gly Ser Gly Thr Lys Leu Glu Ile Lys
100 105

<210> SEQ ID NO 46
<211> LENGTH: 98
<212> TYPE: PRT
<213> ORGANISM: Homo sapiens

<400> SEQUENCE: 46

Gly His Leu Pro Lys Pro Thr Leu Trp Ala Glu Pro Gly Ser Val Ile
1 5 10 15

-continued

```
Thr Gln Gly Ser Pro Val Thr Leu Arg Cys Gln Gly Gly Gln Glu Thr
            20                  25                  30

Gln Glu Tyr Arg Leu Tyr Arg Glu Lys Lys Thr Ala Leu Trp Ile Thr
        35                  40                  45

Arg Ile Pro Gln Glu Leu Val Lys Lys Gly Gln Phe Pro Ile Pro Ser
    50                  55                  60

Ile Thr Trp Glu His Ala Gly Arg Tyr Arg Cys Tyr Tyr Gly Ser Asp
65                  70                  75                  80

Thr Ala Gly Arg Ser Glu Ser Ser Asp Pro Leu Glu Leu Val Val Thr
                85                  90                  95

Gly Ala


<210> SEQ ID NO 47
<211> LENGTH: 101
<212> TYPE: PRT
<213> ORGANISM: Homo sapiens

<400> SEQUENCE: 47

Tyr Ile Lys Pro Thr Leu Ser Ala Gln Pro Ser Pro Val Val Asn Ser
1               5                   10                  15

Gly Gly Asn Val Ile Leu Gln Cys Asp Ser Gln Val Ala Phe Asp Gly
            20                  25                  30

Phe Ser Leu Cys Lys Glu Gly Glu Asp Glu His Pro Gln Cys Leu Asn
        35                  40                  45

Ser Gln Pro His Ala Arg Gly Ser Ser Arg Ala Ile Phe Ser Val Gly
    50                  55                  60

Pro Val Ser Pro Ser Arg Arg Trp Trp Tyr Arg Cys Tyr Ala Tyr Asp
65                  70                  75                  80

Ser Asn Ser Pro Tyr Glu Trp Ser Leu Pro Ser Asp Leu Leu Glu Leu
                85                  90                  95

Leu Val Leu Gly Val
            100
```